(12) United States Patent
Li et al.

(10) Patent No.: US 12,145,993 B2
(45) Date of Patent: Nov. 19, 2024

(54) SEQUENCE OF ANTIBODY HEAVY CHAIN CONSTANT REGION FOR ENHANCING AGONISTIC ANTIBODY ACTIVITY

(71) Applicant: SHANGHAI JIAO TONG UNIVERSITY SCHOOL OF MEDICINE, Shanghai (CN)

(72) Inventors: Fubin Li, Shanghai (CN); Xiaobo Liu, Shanghai (CN); Yan Zhang, Shanghai (CN); Yingjie Zhao, Shanghai (CN); Huan Shi, Shanghai (CN); Huihui Zhang, Shanghai (CN)

(73) Assignee: SHANGHAI JIAO TONG UNIVERSITY SCHOOL OF MEDICINE, Shanghai (CN)

( * ) Notice: Subject to any disclaimer, the term of this patent is extended or adjusted under 35 U.S.C. 154(b) by 257 days.

(21) Appl. No.: 16/308,156

(22) PCT Filed: Jun. 8, 2017

(86) PCT No.: PCT/CN2017/087620
§ 371 (c)(1),
(2) Date: Dec. 7, 2018

(87) PCT Pub. No.: WO2017/211321
PCT Pub. Date: Dec. 14, 2017

(65) Prior Publication Data
US 2019/0263918 A1 Aug. 29, 2019

(30) Foreign Application Priority Data
Jun. 8, 2016 (CN) .......................... 201610404956.7

(51) Int. Cl.
| | | |
|---|---|---|
| *C07K 16/28* | (2006.01) | |
| *A61K 39/39* | (2006.01) | |
| *A61K 39/395* | (2006.01) | |
| *A61P 35/00* | (2006.01) | |
| *A61P 37/04* | (2006.01) | |
| *C07K 16/00* | (2006.01) | |
| *C07K 16/46* | (2006.01) | |
| *G01N 33/68* | (2006.01) | |

(52) U.S. Cl.
CPC .......... *C07K 16/2878* (2013.01); *A61K 39/39* (2013.01); *A61K 39/395* (2013.01); *A61P 35/00* (2018.01); *A61P 37/04* (2018.01); *C07K 16/00* (2013.01); *C07K 16/28* (2013.01); *C07K 16/46* (2013.01); *G01N 33/68* (2013.01); *C07K 2317/522* (2013.01); *C07K 2317/53* (2013.01); *C07K 2317/569* (2013.01); *C07K 2317/75* (2013.01); *C07K 2317/92* (2013.01)

(58) Field of Classification Search
CPC .................... C07K 2317/60; C07K 2317/66
USPC ........................................ 424/133.1, 134.1
See application file for complete search history.

(56) References Cited

U.S. PATENT DOCUMENTS

| | | | |
|---|---|---|---|
| 7,288,251 B2 | 10/2007 | Bedian et al. | |
| 2015/0299296 A1* | 10/2015 | Katada | A61P 29/00 530/387.3 |
| 2016/0046693 A1 | 2/2016 | Igawa et al. | |
| 2020/0140562 A1 | 5/2020 | Tsun et al. | |
| 2022/0153849 A1* | 5/2022 | Ackerman | A61P 35/00 |
| 2023/0220042 A1* | 7/2023 | Li | C07K 16/00 424/133.1 |

FOREIGN PATENT DOCUMENTS

| | | |
|---|---|---|
| CN | 101014619 A | 8/2007 |
| CN | 103260640 A | 8/2013 |
| CN | 104244980 A | 12/2014 |
| CN | 104736706 A | 6/2015 |
| CN | 104918957 A | 9/2015 |
| CN | 104955844 A | 9/2015 |
| WO | 2006/019447 A1 | 2/2006 |
| WO | 2012/087746 A1 | 6/2012 |
| WO | 2014/070934 A1 | 5/2014 |
| WO | 2014/121087 A1 | 8/2014 |
| WO | 2015/070972 A1 | 5/2015 |
| WO | 2015/184099 A1 | 12/2015 |
| WO | WO 2022042692 A1 * | 3/2022 |

OTHER PUBLICATIONS

Chen et al. (Theranostics 2021, vol. 11, Issue 4: 1901-1917).*
Czajkowsky et al. (Sci Rep Apr. 27, 2015;5:9526).*
(Continued)

*Primary Examiner* — Lynn A Bristol
(74) *Attorney, Agent, or Firm* — Kilpatrick Townsend & Stockton LLP

(57) ABSTRACT

Provided herein is a heavy chain constant region comprising a CH1 domain, a hinge region, a CH2 domain and a CH3 domain, wherein the sequences of said CH1 domain and hinge region derive from the sequences of CH1 domain and hinge region in human IgG2, the sequences of said CH2 domain and CH3 domain derive from the sequences of CH2 domain and CH3 domain in human IgGs; and wherein, said antibody heavy chain constant region has an affinity to human FcγRIIB equal to or higher than the affinity of human IgG1 to human FcγRIIB, said antibody heavy chain constant region has an I/A ratio equal to or higher than human IgG1 has. Also provided are antibodies or fusion proteins based on a heavy chain constant region according to the above, wherein the antibody heavy chain constant region significantly enhances agonistic activity of the antibodies or fusion proteins and improves efficacy of the antibodies or fusion proteins in treating diseases like tumors and autoimmune diseases.

18 Claims, 12 Drawing Sheets

Specification includes a Sequence Listing.

(56) References Cited

OTHER PUBLICATIONS

International Search Report in PCT Appln. PCT/CN2017/087620 mailed Aug. 2, 2017; 6 pages.

Chu, S.Y. et al.; Inhibition of B Cell Receptor-Mediated Activation of Primary Human B Cells by Coengagement of CD19 and FC γ RIIb with Fc-Engineered Antibodies; *Molecular Immunology*; vol. 45; Aug. 8, 2008; p. 3926-3933.

Dahan, R. et al.; "Therapeutic Activity of Agonistic, ZHuman Anti-CD40 Monoclonal Antibodies Requires Selective Fcg γ R Engagement"; *Cancer Cell*; vol. 29; Jun. 13, 2016; pp. 820-831.

Mimoto, F. et al.; "Engineered Antibody Fc Variant with Selectively Enhanced FC γ RIIb Binding over both Fc γ RIIa (R131) and Fc γ RIIa (H131)"; *Protein Engineering, Design & Selection*; vol. 26, No. 10; Jun. 5, 2013; pp. 589-598.

Mimoto, F. et al.; "Chain A, Crystal Structure of Lib Selective Fc Variant, FC (v12), in Complex with Fcgriib"; *Genpept*; Nov. 26, 2014; PDB: 3WJL_A; 6 pages.

Strohl, W.R.; "Optimization of Fc-mediated Effector Functions of Monoclonal Antibodies"; *Current Opinion in Biotechnology*; vol. 20; Nov. 4, 2009; pp. 685-691.

Xiaojie Yu, et al.; Isotype Switching Converts Anti-CD40 Antagonism to Agonism to Elicit Potent Antitumor Activity; Cancer Cell; vol. 37; Jun. 8, 2020; 37 pgs.

Xiaojie Yu, et al.; Complex Interplay between Epitope Specificity and Isotype Dictates the Biological Activity of Anti-human CD40 Antibodies; Cancer Cell; vol. 33, Apr. 9, 2018; 23 pgs.

Pamela Zhang, et al.; Ligand-Blocking and Membrane-Proximal Domain Targeting Anti-OX40 Antibodies Mediate Potent T Cell-Stimulatory and Anti-Tumor Activity; Cell Reports; vol. 27; Jun. 11, 2019; 21 pgs.

Xiaobo Liu, et al.; Human immunoglobulin G hinge regulates agonistic anti-CD40 immunostimulatory and antitumour activities through biophysical flexibility; Nature Communications; 2019; 10:4206; 36 pgs.

Lee P. Richman, et al.; Anti-human CD40 monoclonal antibody therapy is potent without FcR crosslinking; OncoImmunology 3, e28610; Apr. 2014; 2 pgs.

* cited by examiner

```
                                                                                    Section 1
             (1) 1         10         20         30         40         50         60
     EU Index | 118←-------------------------------------------------CH1------------------
        G1   (1) ASTKGPSVFPLAPSSKSTSGGTAALGCLVKDYFPEPVTVSWNSGALTSGVHTFPAVLQSS
        G2   (1) ASTKGPSVFPLAPCSRSTSESTAALGCLVKDYFPEPVTVSWNSGALTSGVHTFPAVLQSS
        G3   (1) ASTKGPSVFPLAPCSRSTSGGTAALGCLVKDYFPEPVTVSWNSGALTSGVHTFPAVLQSS
        G4   (1) ASTKGPSVFPLAPCSRSTSESTAALGCLVKDYFPEPVTVSWNSGALTSGVHTFPAVLQSS
   Consensus (1) ASTKGPSVFPLAPCSRSTSGSTAALGCLVKDYFPEPVTVSWNSGALTSGVHTFPAVLQSS
                                                                                    Section 2
            (61) 61        70         80         90        100        110        120
     EU Index ----------------------------------------→215 | 216←---------------------
        G1  (61) GLYSLSSVVTVPSSSLGTQTYICNVNHKPSNTKVDKRVE- - - - - - - - - - - - - - - - - -
        G2  (61) GLYSLSSVVTVPSSNFGTQTYTCNVDHKPSNTKVDKTVER- - - - - - - - - - - - - - - - - -
        G3  (61) GLYSLSSVVTVPSSSLGTQTYTCNVNHKPSNTKVDKRVELKTPLGDTTHTCPRCPEPKSC
        G4  (61) GLYSLSSVVTVPSSSLGTKTYTCNVDHKPSNTKVDKRVES- - - - - - - - - - - - - - - - - -
   Consensus (61) GLYSLSSVVTVPSSSLGTQTYTCNVNHKPSNTKVDKRVE Section 3
           (121) 121        130        140        150        160        170        180
     EU Index ---------Hinge--------------------------------------→230 | 231←----------
        G1 (100) - - - - - - - - - - - - - - - - - - - - - - - - PKSCDKTHTCPPCPAPELLGGPSVFLFPPKPKDT
        G2 (101) - - - - - - - - - - - - - - - - - - - - - - - - - - - KCCVECPPCPAPPVAG-PSVFLFPPKPKDT
        G3 (121) DTPPCPRCPEPKSCDTPPPCPRCPEPKSCDTPPPCPRCPAPELLGGPSVFLFPPKPKDT
        G4 (101) - - - - - - - - - - - - - - - - - - - - - - - - - - - KYGPPCPSCPAPEFLGGPSVFLFPPKPKDT
   Consensus (121)                              PKSCK   PPCPPCPAPELLGGPSVFLFPPKPKDT
                                                                                    Section 4
           (181) 181        190        200        210        220        230        240
     EU Index ------------------------------------CH2-----------------------------------
        G1 (134) LMISRTPEVTCVVVDVSHEDPEVKFNWYVDGVEVHNAKTKPREEQYNSTYRVVSVLTVLH
        G2 (130) LMISRTPEVTCVVVDVSHEDPEVQFNWYVDGVEVHNAKTKPREEQFNSTFRVVSVLTVVH
        G3 (181) LMISRTPEVTCVVVDVSHEDPEVQFKWYVDGVEVHNAKTKPREEQYNSTFRVVSVLTVLH
        G4 (131) LMISRTPEVTCVVVDVSQEDPEVQFNWYVDGVEVHNAKTKPREEQFNSTYRVVSVLTVLH
   Consensus (181) LMISRTPEVTCVVVDVSHEDPEVQFNWYVDGVEVHNAKTKPREEQFNSTFRVVSVLTVLH
                                                                                    Section 5
           (241) 241        250        260        270        280        290        300
     EU Index ---------------------------------→340 | 341←-------------------------------
        G1 (194) QDWLNGKEYKCKVSNKALPAPIEKTISKAKGQPREPQVYTLPPSRDELTKNQVSLTCLVK
        G2 (190) QDWLNGKEYKCKVSNKGLPAPIEKTISKTKGQPREPQVYTLPPSREEMTKNQVSLTCLVK
        G3 (241) QDWLNGKEYKCKVSNKALPAPIEKTISKTKGQPREPQVYTLPPSREEMTKNQVSLTCLVK
        G4 (191) QDWLNGKEYKCKVSNKGLPSSIEKTISKAKGQPREPQVYTLPPSQEEMTKNQVSLTCLVK
   Consensus (241) QDWLNGKEYKCKVSNKALPAPIEKTISKTKGQPREPQVYTLPPSREEMTKNQVSLTCLVK
                                                                                    Section 6
           (301) 301        310        320        330        340        350        360
     EU Index ---------------------------------CH3-----------------------------------
        G1 (254) GFYPSDIAVEWESNGQPENNYKTTPPVLDSDGSFFLYSKLTVDKSRWQQGNVFSCSVMHE
        G2 (250) GFYPSDIAVEWESNGQPENNYKTTPPMLDSDGSFFLYSKLTVDKSRWQQGNVFSCSVMHE
        G3 (301) GFYPSDIAVEWESSGQPENNYNTTPPMLDSDGSFFLYSKLTVDKSRWQQGNIFSCSVMHE
        G4 (251) GFYPSDIAVEWESNGQPENNYKTTPPVLDSDGSFFLYSRLTVDKSRWQEGNVFSCSVMHE
   Consensus (301) GFYPSDIAVEWESNGQPENNYKTTPPMLDSDGSFFLYSKLTVDKSRWQQGNVFSCSVMHE
                                                                                    Section 7
           (361) 361             378
     EU Index ---------------------→447|
        G1 (314) ALHNHYTQKSLSLSPGK-
        G2 (310) ALHNHYTQKSLSLSPGK-
        G3 (361) ALHNRFTQKSLSLSPGK-
        G4 (311) ALHNHYTQKSLSLSLGK-
   Consensus (361) ALHNHYTQKSLSLSPGK
```

Figure 2

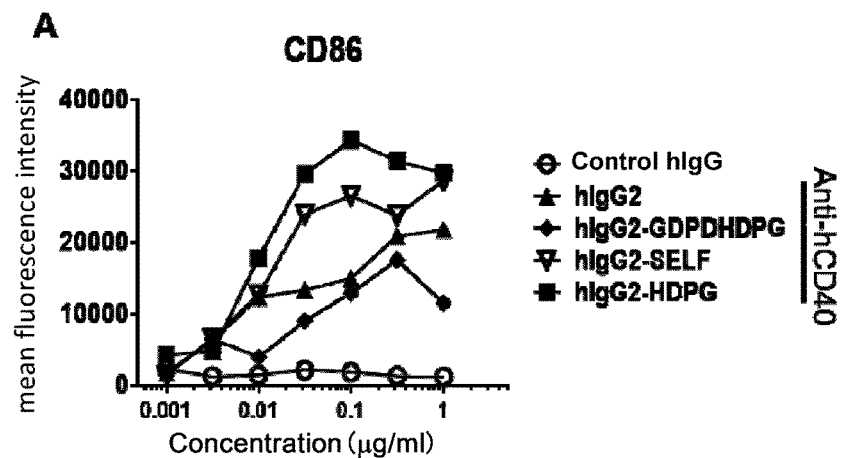
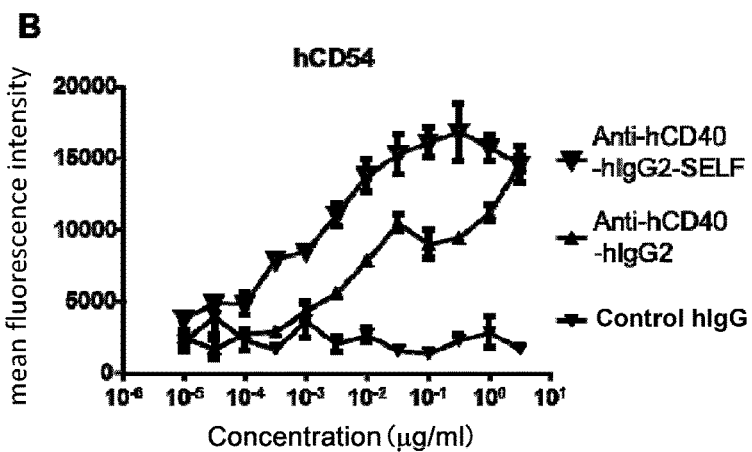
Figure 8
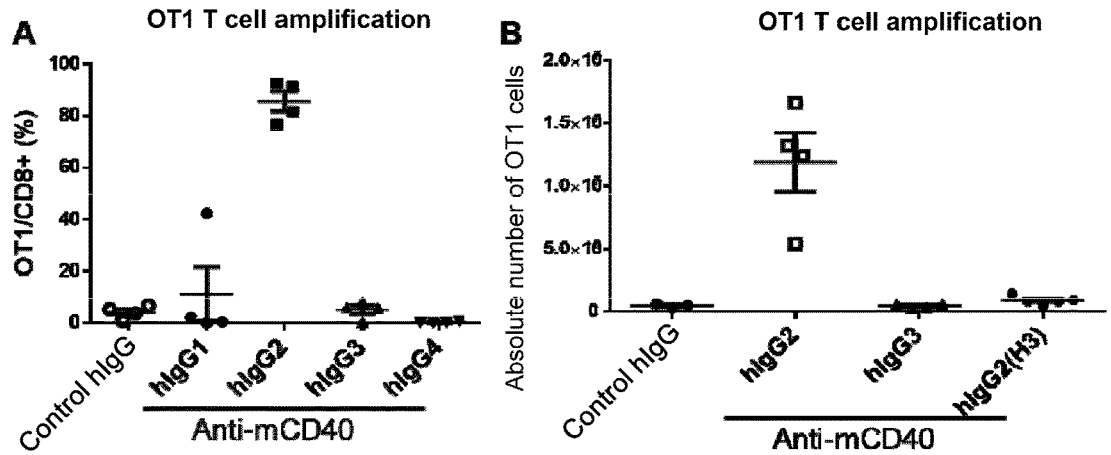
Figure 9

SEQUENCE OF ANTIBODY HEAVY CHAIN CONSTANT REGION FOR ENHANCING AGONISTIC ANTIBODY ACTIVITY

CROSS-REFERENCE TO RELATED APPLICATIONS

This application is a national phase application under 35 U.S.C. 371 claiming priority to PCT/CN2017/087620, filed Jun. 8, 2017, which application claims priority to CN 201610404956.7, filed Jun. 8, 2016, the teachings of which are hereby incorporated by reference in their entireties for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file P2018-2259_sequence_listing.txt, created on Dec. 6, 2018, 186,251 bytes, machine format IBM-PC, MS-Windows operating system, is hereby incorporated by reference in its entirety for all purposes.

FIELD OF THE INVENTION

The present invention belongs to the field of biopharmaceuticals, and specifically relates to a class of heavy chain constant region sequences and molecules, which enhance activity of agonistic antibodies or agonistic molecules (fusion proteins comprising a heavy chain constant region sequence). The present invention also relates to antibodies or fusion proteins constructed on basis of these heavy chain constant regions.

BACKGROUND OF THE INVENTION

In the past thirty years, in the field of biopharmaceuticals, molecular targeted therapies based on antibodies and heavy chain constant regions (including the Fc fragment), such as antibody and heavy chain constant region-based fusion proteins, have achieved great success and continued to be focuses of interests. They provide new methods and possibilities of therapy for various diseases. There have been about 30 heavy chain constant region-based biotherapies (including heavy chain constant region fusion proteins) approved already, while over 300 in clinical trials. These biotherapies can be classified into three classes according to their mechanisms of action: effector molecules that clear the targets (molecules and cells), blocking molecules that block the signaling pathways involving the targets, and agonistic molecules that activate the signaling pathways downstream to the targets.

Antitumor immunotherapy achieved important breakthroughs these years. This is attributable to the use of antibodies that are capable of blocking check-points in immunosuppression and improving the activity of immune cell to kill tumors. Still, a lot of cancer patients are irresponsive to existing therapies. Therefore, on one hand, there is a need to improve existing antitumor immunotherapies, and on the other hand, there is a need for new medicaments useful in antitumor immunotherapies. Particularly notable is the class of antitumor immunotherapeutics that are called "agonistic antibodies". They bind to the target molecules on surface of immune cells that transmit immunostimulatory signals to activate the important immunostimulatory signaling pathway controlled by these molecules, which, in turn, enhances antitumor immune responses and kills tumor cells indirectly. Although agonistic antitumor immunotherapeutic antibodies have been proven highly potential in animal models and have become a widely acknowledged and expected antitumor immunotherapy concept, the development of such antibodies has not been succeeded yet and is still a challenge in the field of antitumor immunotherapy. Further, agonistic antibody stimulation is also favorable as a means to intervene and to modulate critical signaling pathways in other biological events, and has broad application prospects in the field of disease prevention and treatment. For instance, activation of immunosupression signaling pathways may advantageously reduce inflammation and autoimmune symptoms.

SUMMARY OF THE INVENTION

A major objective of the invention is to provide a heavy chain constant region sequence and molecule that enhances activity of an agonistic antibody or an agonistic molecule (a fusion protein comprising a heavy chain constant region sequence) and antibodies or fusion proteins constructed on basis of the heavy chain constant region.

Accordingly, as one embodiment of the invention to solve the above technical problem, provided herein is a heavy chain constant region comprising a CH1 domain, a hinge region, a CH2 domain and a CH3 domain, wherein the sequences of said CH1 domain and hinge region derive from the sequences of the CH1 domain and hinge region in human IgG2, and the sequences of said CH2 domain and CH3 domain are selected from the sequences:

a) derived from the sequences of the CH2 domain and CH3 domain in human IgG1, while said CH2 domain and CH3 domain comprise the mutations of G237D, P238D, P271G and A330R; or b) derived from the sequences of the CH2 domain and CH3 domain in human IgG1, while said CH2 domain and CH3 domain comprise the mutations of G237D, P238D, H268D, P271G and A330R; or c) derived from the sequences of the CH2 domain and CH3 domain in human IgG2, while said CH2 domain and CH3 domain comprise the mutations of S267E and L328F; or d) derived from the sequences of the CH2 domain and CH3 domain in human IgG2, while said CH2 domain and CH3 domain comprise the mutations of H268D and P271G.

Preferably, the heavy chain constant region has the sequence of SEQ ID NO: 11: or the heavy chain constant region has the sequence of SEQ ID NO: 12: or the heavy chain constant region has the sequence of SEQ ID NO: 13: or the heavy chain constant region has the sequence of SEQ ID NO: 14.

In another aspect, provided herein is an heavy chain constant region comprising a CH1 domain, a hinge region, a CH2 domain and a CH3 domain, wherein the sequences of said CH1 domain and hinge region derive from the sequences of the CH1 domain and hinge region in human IgG2, the sequences of said CH2 domain and said CH3 domain derive from the sequences of the CH2 domain sequence and CH3 domain in human IgG; and wherein the affinity of the antibody heavy chain constant region to human is equal to or higher than that of IgG1 to human FcγRIIB, and said antibody heavy chain constant region has an I/A ratio equal to or higher than human IgG1 has.

Preferably, the affinity of the antibody heavy chain constant region to human FcγRIIB is 3.2 times or more higher than that of human IgG1 to human FcγRIIB, and the antibody heavy chain constant region has an I/A ratio equal to or higher than 0.32. Also preferably, the affinity of the antibody heavy chain constant region to human FcγRIIB is equal to or higher than that of human IgG1 to human FcγRIIB, and the antibody heavy chain constant region has an I/A ratio equal to or higher than 1. More preferably, the affinity of the antibody heavy chain constant region to human FcγRIIB 30 times or more higher than that of human IgG1 to human FcγRIIB, and the antibody heavy chain constant region has an I/A ratio equal to or higher than 1. More preferably, the affinity of the antibody heavy chain constant region to human FcγRIIB is 60 times or more higher than that of human IgG1 to human FcγRIIB, and the antibody heavy chain constant region has an I/A ratio equal to or higher than 40. Even more preferably, the affinity of the antibody heavy chain constant region to human FcγRIIB is 90 times or more higher than that of human IgG1 to human FcγRIIB, and the antibody heavy chain constant region has an I/A ratio equal to or higher than 100.

According to an embodiment of the invention, the heavy chain constant region has an increased affinity to the inhibitory Fc receptor, which enables significantly enhanced crosslinking between the agonistic antibody or agonistic molecule (e.g., agonistic fusion protein) and the Fc receptor and thereby increased agonistic activity of the agonistic antibody or agonistic molecule, and it also has a decreased affinity to an activating Fc receptor, which leads to reduced cytotoxicity mediated thereby, including ADCC. The heavy chain constant region of the invention makes it possible to develop agonistic antibodies or agonistic molecules with improved activities.

In another aspect, provided herein is a fusion protein that comprises a heavy chain constant region according to the above and an antigen binding module at the N-terminal or the C-terminal of the heavy chain constant region.

Preferably, the antigen binding module is selected from antigen binding fragments of antibodies, adnectins, nanobodies, miniantibodies, affibodies, affilins, target-binding regions of receptors, cell adhesion molecules, ligands, enzymes, cytokines or chemokines. More preferably, the antigen binding module is a nanobody.

Nanobodies are derives from the heavy chain variable regions of alpaca antibodies. A variable region can be fused with the heavy chain constant region of the invention to form a chimeric antibody molecule having the structure of a whole camel antibody (consisting of two heavy chains). These chimeric antibody molecules may inherit the high affinity and the high specificity from the nanobody as well as the enhanced agonistic activity from the heavy chain variable region of the invention, which promises a good prospect of development.

In another preferred embodiment of the antibody of the invention, the antigen binding module is a ligand. The ligand may be an immune costimulatory molecule. The costimulatory molecule may be one selected from CD80, CD86, ICOSL, OX40L, CD137L, CD40L, CD30L, CD27L, CD244, CD150, CD48, CD84, CD319, Ly118 and CD229. These fusion proteins are useful as anticancer agents.

In another preferred embodiment of the fusion protein according to the invention, the antigen binding module targets an antigen selected from the group consisting of CD40, DR5, OX40, CD137, CD27, CD30, GITR, HVEM, TACI, DR4 and FAS.

The CD40-targeted agonistic molecules (fusion proteins) of the invention are useful as an adjuvant in vaccines. Such an adjuvant may be used in combination with a vaccine (e.g., OVA) to form a vaccine composition for use in prevention and/or treatment of tumors or for used in prevention and/or treatment of infections.

In another preferred embodiment of the fusion protein according to the invention, the antigen binding module targets an antigen selected from the group consisting of PD-1, CTLA-4, VISTA, TIM-3, BTLA and LAG-3. Acting on these targets, the fusion proteins are useful for producing medicaments for reducing inflammation and/or for ameliorating autoimmune diseases, such as asthma.

In another preferred embodiment of the fusion protein according to the invention, the antigen binding module is a ligand. The ligand may be an immuno-inhibitory ligand. The immuno-inhibitory ligand may be one selected from the group consisting of PD-L1, PD-L2, B7-H3, B7-H4, CD47, VISTA, HVEM and GAL9. Acting on these targets, the fusion proteins are useful for producing medicaments for reducing inflammation and/or for ameliorating autoimmune diseases, such as asthma.

In another aspect, provided herein is an antibody comprising a heavy chain constant region of the invention according to the above.

Preferably, the antibody is an agonistic antibody.
Preferably, the antibody is an IgG
Preferably, the antibody is a human antibody or a humanized antibody or a chimeric antibody.

In another preferred embodiment of the antibody according to the invention, the antibody targets an antigen selected from the group consisting of CD40, DR5, OX40, CD137, CD27, CD30, GITR, HVEM, TACI, DR4 and FAS.

Particularly, the target antigen is CD40.

More preferably, the antibody comprises a heavy chain having the sequence of SEQ ID NO: 27 and a light chain having the sequence of SEQ ID NO: 47: or the antibody comprises a heavy chain having the sequence of SEQ ID NO: 43 and a light chain having the sequence of SEQ ID NO: 47.

The agonistic antibodies of the invention targeting CD40 are useful as an adjuvant in vaccines. Such an adjuvant may be used in combination with a vaccine (e.g., OVA) to form a vaccine composition for use in prevention and/or treatment of tumors or for use in prevention and/or treatment of infections In another preferred embodiment of the antibody according to the invention, the antibody targets an antigen which is an immuno-inhibitory receptor molecule. The immuno-inhibitory receptor molecule may be one selected from the group consisting of PD-1, CTLA-4, VISTA, TIM-3, BTLA and LAG-3. Acting on these targets, the antibodies are useful for producing medicaments for reducing inflammation and/ or for ameliorating autoimmune diseases, such as asthma.

Also provided herein is use of the fusion protein or the antibody of the invention for manufacturing medicaments for treating cancers.

Preferably, the medicament is for treating colon cancer or fibrosarcoma.

Also provided herein is a pharmaceutical composition comprising a fusion protein or an antibody according to the invention and a pharmaceutically acceptable carrier. The pharmaceutical composition is useful for producing anticancer medicines. Preferably, the medicine is for treating colon cancer or fibrosarcoma.

Also provided herein is a method for enhancing endogenous immune response in a human subject, comprising administering to the human subject a therapeutically effective dosage of a fusion protein or an antibody according to the invention.

Also provided herein is an immunotherapy method, comprising administering to a human subject a therapeutically effective dosage of a fusion protein or an antibody according to the invention.

Advantages of the invention include the followings: a heavy chain constant region sequence is provided, which, as compared to existing molecules of the same class, significantly enhances the activity of an agonistic antibody or molecule (a fusion protein comprising a chain constant region sequence): the agonistic antibodies or fusion proteins comprising the heavy chain constant region sequence of the invention possess not only improved activity but also broadened range of effective dosage and improved safety, as well as significant market value.

BRIEF DESCRIPTION OF THE DRAWINGS

FIG. 2: Alignment among heavy chain constant regions from different human IgG subclasses (IgG1, IgG2, IgG3 and IgG4) (SEQ ID NOs 11-14).

FIG. 8: The anti-human CD40) antibodies comprising JAC3 (anti-hCD40-hIgG2-SELF) and JAC4 (anti-hCD40-hIgG2-HDPG) exhibited stronger agonistic activity than the hIgG2 antibody. The specified anti-human CD40 antibodies were tested for their activity to activate B-cells in hCD40$^{Tg}$hFCGR$^{Tg}$ spleen cells (A) and PMBCs (B). The assay on activity to activate B-cells reveals that anti-hCD40-hIgG2-SELF and anti-hCD40-hIgG2-HDPG are more supportive than human hIgG2 for activity of agonistic anti-CD40 antibodies. The specified anti-human CD40) antibodies were tested for their activity to activate B-cells in hCD40$^{Tg}$hFCGR$^{Tg}$ spleen cells (A) and PMBCs (B). The cells were incubated with the control or the agonistic anti-human CD40 antibodies at the specified gradient dilutions in culture medium for 48 hours, and then assayed by flow-cytometry for expression of mouse B-cell activation marker CD86 (A) or human B-cell activation marker CD54. Increase in expression of the molecules indicates activity of the corresponding anti-CD40 antibody.

FIG. 9): Compared to hIgG3, the CH1-hinge region from hIgG2 rendered the agonistic anti-CD40 antibodies with stronger in vivo immuno-activating activity. The method was the same as for FIG. 4 and FIG. 7, wherein activity of the specified different anti-murine CD40 antibodies were evaluated in hFCGR$^{Tg}$ mice using the OVA vaccine model. Activity of the anti-CD40 antibodies were detected by OT-I T-cell proliferation. The dosage of antibody was 10 μg/mouse. (A) Among the four hIgG subclasses, hIgG2 exhibited stronger immuno-activating activity, while the rest, i.e., hIgG1, hIgG3 and hIgG4 are almost inactive. (B) Compared to the control group, hIgG2 exhibited significant activity, while when the CH1-hinge region from hIgG2 was replaced by the CH1-hinge region from hIgG3, the obtained variant hIgG2 (H3) became substantially inactive.

DETAILED DESCRIPTION OF THE INVENTION

Unless otherwise stated, the scientific and technical terms used herein shall be understood as having the meanings as commonly understood by one of ordinary skills in the art. Unless otherwise required, as used herein, terms in singular forms include the meaning of plurality, and vice versa. In general, as used herein, nomenclatures and techniques in the cell and tissue culturing/incubation, molecular biology, immunology, protein and nucleic acid chemistry described herein are those already known and commonly used in the art.

Methods and techniques used in the present invention are generally performed as in conventional practices and as described in general and specialized references cited and discussed in this disclosure, unless otherwise indicated. For example, reference can be made to the followings: Molecular Cloning: A Laboratory Manual, Sambrook et al., the $2^{nd}$ Edition, Cold Spring Harbor Laboratory Press, Cold Spring Harbor, N.Y., 1989; Current Protocols in Molecular Biology, Ausubel et al. Greene Publishing Associates, 1992: Antibodies: A Laboratory Manual, Harlow and Lane, Cold Spring Harbor Laboratory Press, Cold Spring Harbor, N.Y., 1990, all being incorporated by reference in their entirety. Enzymatic reactions and purifications are performed by following manufacturers' instructions or as known in the art or as specified in the present disclosure. As used herein, nomenclatures, test methods and techniques in biology, pharmacology, medicine and pharmaceutical chemistry are those already known and commonly used in the art. Chemical synthesis, chemical analysis, pharmaceutical manufacturing, formulation and delivery and patient treatment all follow standard practices.

Unless otherwise stated, the terms have the meanings as defined below:

The terms "antibody" and "monoclonal antibody" ("mAb") refer to a preparation of antibody molecules that are homogeneous in molecular composition (i.e., antibody molecules having substantially the same primary sequence and exhibiting the same binding specificity and affinity to a specific epitope). Antibodies can be produced by hybridoma technique, recombinant methods, transgenic techniques or other techniques known in the art.

The term "antibody" includes inter alias immunoglobulins (Igs). According to their chemistry and biologics, these antibodies are classified as IgM, IgG IgA, IgE and IgD. Human IgGs include the four subclasses being IgG1, IgG2, IgG3 and IgG4 (Vidarsson G Dekkers G and Rispens T (2014) IgG subclasses and allotypes: from structure to effector functions. Front. Immunol. 5:520). In the present disclosure, "hIgG1", "hIgG2". "hIgG3" and "hIgG4" refer to human IgG1, IgG2. IgG3 and IgG4, respectively.

Figure 1:
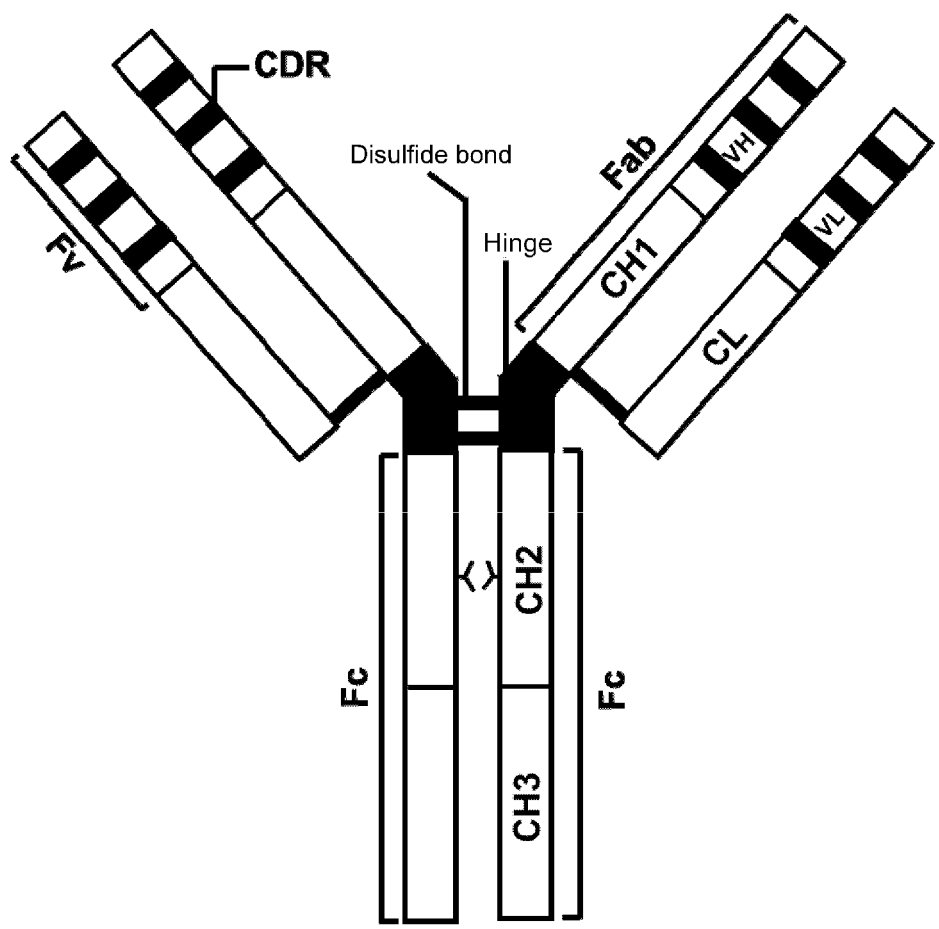
FIG. 1: A schematic diagram of the basic structure of antibodies.

Antibodies specifically bind to corresponding antigens, and each comprises at least two heavy (H) chains and two light (L) chains that bind to one another through disulfide bonds. Each heavy chain comprises a heavy chain variable region (VH) and a heavy chain constant region (CH); and each light chain comprises a light chain variable region (VL) and a light chain constant region (CL). In the context of antibodies, the "heavy chain constant region" may comprise three domains identified as CH1, CH2 and CH3, as well as a hinge region (Hinge) between the CH1 domain and the CH2 domain. FIG. 1 is a schematic diagram of the basic structure of an IgG antibody.

Kabat and his colleagues collected a large number of primary sequences of heavy chain and light chain variable regions. They divided each primary sequence into CDRs and frames based on sequence conservation and compiled them into a list (see SEQUENCES OF IMMUNOLOGICAL INTEREST. 5th Edition. NIH publication. No. 91-3242. E. A. Kabat et al., incorporated in its entirety by reference). IMGT database compiled the EU indexes for the domains of human IgG (see the internet at .imgt.org/IMGTScientific-Chart/Numbering/Hu_IGHGnber.html). In the context of IgG antibodies, the CH1 domain in the heavy chain constant region refers to positions 118-215 numbered according to the Kabat EU index: the CH2 domain in the heavy chain constant region refers positions 231-340 numbered according to the Kabat EU index: the CH3 domain in the heavy chain constant region refers positions 341-447 numbered according to the Kabat EU index; and the hinge region (Hinge) in the heavy chain constant region spans across position 216 (E216 in IgG1) to position 230 (P230 in IgG1) numbered according to the Kabat EU index. FIG. 2 shows the sequence alignment among the heavy chain variable regions of human IgG1. IgG2. IgG3 and IgG4.

Each light chain comprises a "light chain variable region" (VL) and a "light chain constant region". The light chain constant region is composed of a CL domain. VH and VL can each be subdivided into hypervariable regions called "complementary determining regions (CDRs)" and the interspersed relatively conserved regions called "frame regions (FRs)". VH and VL are each composed of three CDRs and four FRs as arranged in the following order from the amino end to the carboxyl end: FR1, CDR1, FR2, CDR2, FR3, CDR3, FR4. The heavy chain and the light chain variable regions provide the domains that interact with antigens.

"Fc region" (crystallizable fragment region) or "Fc domain" or "Fc" refers to the C-terminal portion of the heavy chain, which mediates the binding between the immunoglobulin and host tissues or factors, including the binding to Fc receptors on various immune cells (e.g., effector cells) or to the first component of the classic complement system (C1q). For the allotypes of IgG IgA and IgD antibodies, the Fc region is composed of two identical protein fragments from CH2 and CH3 domains of the two heavy chains; and in IgM and IgE, the Fc region comprises in each polypeptide chain three heavy chain constant domains (CHs 2-4). Though boundaries of Fc regions of heavy chains of immunoglobulins are variable. Fc regions in heavy chains of human IgGs are normally defined as the segment spanning position C226 or P230 to the carboxyl end of the heavy chains, as numbered according to the EU index, the same as in the Kabat system. As used herein, the Fc region may be a naturally occurring or native Fc sequence or an Fc variant.

"Fc receptor" or "FcR" is the receptor binding to the Fc region of an immunoglobulin. FcRs binding to IgG antibodies include the FcγR family, including their allelic variants and alternative splicing variants. Members of the human Fcγ receptor family include FcγRI (CD64). FcγRIIA (CD32a), FcγRIIB (CD32b), FcγRIIIA (CD16a), FcγRIIIB (CDT6b). Therein, FcγRIIB is the only inhibitory Fcγ receptor, and the rest are all activating Fcγ receptors. Most natural effector cells co-express one or more activating FcγRs and the inhibitory FcγRIIB, while natural killer (NK) cells selectively express an activating Fcγ receptor (FcγRIII in mice, FcγRIIIA in humans), while not the inhibitory FcγRIIB in mice and humans. These Fcγ receptors have different molecular structures and therefore different affinity to subclasses of IgG antibodies. Among these Fcγ receptors, FcγRI is a high-affinity receptor, while FcγRIIA, FcγRIIB and FcγRIIIA are low-affinity receptors. Genetic polymorphism is seen in these different Fcγ receptors, which also influences binding affinity. Most dominant genetic polymorphisms include the R131/H131 in FcγRIIA and the V158/F158 in FcγRIIIA. Some of these polymorphisms are found diseases-associated. And, responsiveness to certain therapeutic antibodies depends on presence of certain polymorphism in Fcγ receptors.

As used herein, a "sequence" should be understood as encompassing sequences that are substantially identical to a specified one according to the invention. The term "substantially identical sequences" refers sequences sharing a sequence identity of at least 70, 75 or 80%, preferably at least 90 or 95%, more preferably at least 97, 98 or 99% in the optimal alignment using, for example, GAP or BESTFIT and the default gap value. Preferably, the differential residues are conservative amino acid substitution. The term "conservative amino acid substitution" refers to substitution between amino acid residues having similar chemistry (e.g., charge or hydrophilicity) in the side-chain R group. Generally, conservative amino acid substitution does not substantially change a protein's functional properties. When difference(s) between two or more amino acid sequences reside(s) in conservative substitution(s), the sequence identity percentage or similarity value can be up-adjusted to correct for the conservativeness of substitution. See, for example, Pearson, Methods Mol.Biol.243: 307-31(1994). Examples of amino acids having side-chains with similar chemistry include: 1) aliphatic side chains, including glycine, alanine, valine, leucine and isoleucine; 2) aliphatic-hydroxy side chains, including serine and threonine; 3) amide-containing side chains, including asparagine and glutamine; 4) aromatic side chains, including phenylalanine, tyrosine and tryptophan; 5) basic side chains, including lysine, arginine and histidine; 6) acidic side chains, including aspartic acid and glutamic acid; and 7) sulfur-containing side chain, including cysteine and methionine. Preferred conservative amino acid substitutions include valine-leucine-isoleucine, phenylalanine-tyrosine, lysine-arginine, alanine-valine, glutamate-aspartate, and asparagine-glutamine.

Amino acids of the antibody and a fragment or domain thereof according to the invention are numbered according to the EU numbering system for IgGs (see the internet at .imgt.org/IMGTScientificChart/Numbering/Hu_IGHGnber-.html).

Antibodies usually specifically bind to the corresponding antigens with a high affinity, as indicated by, for example, a dissociation constant (KD) of $10^{-5}$-$10^{-11}$M or less. A KD above about $10^{-4}$M$^{-1}$ is usually understood as indicating a nonspecific binding. In this disclosure, an antibody "specifically binding to" an antigen means that the antibody binds to the antigen or a substantially identical antigen with a high affinity as measured by a KD of $10^{-7}$M or less, preferably $10^{-8}$M or less, more preferably $5 \times 10^{-9}$M or less and most preferably $10^{-8}$-$10^{-10}$M or less, and does not bind to any irrelevant antigen with a significant affinity. An antigen is "substantially identical" to a specified antigen, if they share a high sequence identity, such as a sequence identity of at least 80%, at least 90%, preferably at least 95%, more preferably at least 97%, or even more preferably at least 99%.

As used herein, the terms "ratio of the affinity to the inhibitory Fcγ receptor to the affinity to the activating Fcγ receptor" and "I/A ratio" both refer to the ratio of a protein molecule's affinity to the inhibitory Fc receptor to its affinity to the activating Fc receptor. In this disclosure, the I/A ratio is calculated by the equation: I/A ratio=[the lower of KD (hFcγRIIA) and KD (hFcγRIIIA)]/KD (hFcγRIIB), wherein "KD (hFcγRIIA)" refers to the molecule's equilibrium dissociation constant for hFcγRIIA receptor (as represented by the variant hFcγRIIA-R131), "KD (hFcγRIIIA)" refers to the molecule's equilibrium dissociation constant for hFcγRIIIA receptor (as represented by the variant hFcγRIIIA-F158), "KD (hFcγRIIB)" refers to the molecule's equilibrium dissociation constant for hFcγRIIB receptor, "hFcγRIIA" refers to human FcγRIIA receptor, "hFcγRIIIA" refers to human FcγRIIIA receptor, and "hFcγRIIB" refers to human FcγRIIB receptor. The term "affinity" refers to the capability of two molecules binding to each other, as usually measured by a KD value.

The term "KD" refers to the equilibrium dissociation constant of interaction between two molecules (e.g., a specific antibody vs. an antigen or a specific ligand vs. a receptor). An "antigen binding module" is a protein specifically binding to an antigen with high affinity, and the examples include, but are not limited to antigen binding fragments of antibodies, adnectins, nanobodies, miniantibodies, affibodies, affilins, target-binding regions of receptors, cell adhesion molecules, ligands, enzymes, cytokines and chemokines. Antigens targeted by the antigen binding modules include, but are not limited to the TNF receptor superfamily and immuno-inhibitory receptor molecules.

The term "antigen binding portion of an antibody" refers the amino acid residues in an antibody that are responsible for antigen binding. The antigen binding portion includes the amino acid residues in the "complementary determining regions" or "CDRs". "Frame" or "FR" regions refer to the parts in the variable region that are other than the hypervariable region residues as defined herein. Accordingly, the variable domain in either the light chain or the heavy chain includes, from the N-terminal to the C-terminal, FR1, CDR1, FR2, CDR2, FR3, CDR3 and FR4 regions. Particularly, CDR3 of the heavy chain contributes the most to antigen binding and defines the property of an antibody. CDRs and FRs can be determined according to the standard definitions and/or the residues from "hypervariable loops" in Kabat et al., SEQ ID NO:uences of Proteins of Immunological Interest, the 5$^{th}$ Edition, Public Health Service, National Institutes of Health, Bethesda, MD(1991).

The "antibodies" of the invention include naturally occurring and non-naturally occurring antibodies, monoclonal and polyclonal antibodies, chimeric and humanized antibodies, human and non-human antibodies and wholly synthetic antibodies.

"Human" antibodies refer to such antibodies wherein the variable regions comprise FRs and CDRs from human immunoglobulins. And, the antibody may also comprise a constant region from a human immunoglobulin, if present. A human antibody according to the invention may include amino acid residues not encoded by human immunoglobulin sequences, such as mutations introduced by random or site-directed mutagenesis in vitro or somatic mutation in vivo. However, as used herein, the term "human antibody" has no intention to include such antibodies that comprise non-human mammalian (e.g., mouse) CDR sequences grafted between human frame sequences. The term "human" antibody and "wholly human" antibody are used as synonymous to each other.

A "humanized" antibody refers to an antibody wherein some, majority or all of the amino acids outside the non-human CDR domains are replaced by corresponding amino acids from a human immunoglobulin. In an example of a humanized antibody, some, majority or all of the amino acids outside the non-human antibody CDR domains are replaced by corresponding amino acids from a human immunoglobulin, and some, majority or all of the amino acids in one or more of the CDRs remain unchanged. Minor addition, deletion, insertion, substitution or modification of amino acid(s) is tolerable, as long as it does not destroy the antibody's capability of binding to the corresponding antigen. A "humanized" antibody retains the antigen binding specificity of the original antibody.

A "chimeric antibody" refers to an antibody wherein the variable region(s) come(s) from a species and the constant region(s) from another, for example, an antibody in which the variable region(s) may come from a mouse antibody and the constant region(s) from a human antibody.

An "agonistic antibody" is an antibody that binds to and activates a receptor. Examples of such agonism include, but are not limited to: 1) anti-DR5 agonistic antibody binding to DR5 and inducing apoptosis of cells expressing DR5 receptor; 2) anti-CD40 agonistic antibody binding to target molecule on surface of immune cells to transmit immunostimulatory signals and activating the important immunostimulatory signaling pathway controlled thereby, which, in turn, enhances antitumor immune responses to indirectly kill tumor cells.

Examples of agonistic antibodies in clinical studies include the followings in Table 1.

TABLE 1

Agonistic antibodies in clinical studies

| TNF Receptor Family | Product (Developer) | Antibody Type | Indications |
|---|---|---|---|
| OX40 | MEDI6469 (Providence Health & Services) | murine originated antibody | cancers (solid tumor, prostate cancer) |
| CD27 | CDX-1127(Celldex Therapeutics) | human antibody | various cancers |
| CD40 | Dacetuzumab/ SGN-40(Genentech) | humanized antibody | cancers (CLL, non-Hodgkin's lymphoma, multiple myeloma) |
|  | HCD122(Novartis) |  | multiple myeloma |
|  | ASKP1240(Astellas Pharma/ Kyowa Hakko Kirin Company) |  |  |
|  | Chi Lob 7/4(Cancer Research UK) | chimeric antibody | cancers (non-Hodgkin's lymphoma) |
|  | CP-870893(Pfizer) | human antibody | cancers (melanoma, pancreatic cancer) |
|  | ADC-1013(Alligator Bioscience) | wholly human antibody | tumors; solid tumor |
|  | RO7009789(Roche) |  | Late stage/metastatic solid tumor |
|  | SEA-CD40(Seattle Genetics) |  | cancers |
|  | APX005M(Apexigen) |  | cancers |
| CD30 | SGN-30(Seattle Genetics) | chimeric antibody | cancers (non-Hodgkin's lymphoma) |
|  | XmAb2513(Xencor) | humanized antibody | cancers (non-Hodgkin's lymphoma) |
|  | MDX-1401 (Bristol-Myers Squibb) | human antibody | cancers (non-Hodgkin's lymphoma) |
| 4-1BB | BMS-663513( Bristol-Myers Squibb) | human antibody | Cancer (melanoma, solid tumour) |
|  | PF-05082566(Pfizer/Kyowa Hakko Kirin Company) | human antibody | cancers (non-Hodgkin's lymphoma) |
| DR4 | Mapatumumab/HGS-ETR1(Human Genome Sciences Inc/GSK) | human antibody | various cancers |
| DR5 | Conatumumab/AMG 655(Amgen) | human antibody | various cancers |
|  | Drozitumab/Apomab/PRO95780 (Genentech) | human antibody | various cancers |
|  | Lexatumumab/HGS -ETR2 (National Cancer Institute) | human antibody | cancers |
| OPG | Tigatuzumab/CS-1008/TRA-8 (Ludwig Institute for Cancer Research/Daiichi Sankyo Inc) | humanized antibody | various cancers |
| Fn14 | Enavatuzumab/PDL192(Abbott) | humanized antibody | cancers (solid tumor) |
| GITR | TRX518(GITR) | humanized antibody | cancers (melanoma, pancreatic cancer) |
|  | MEDI1873(MedImmune) |  | Late stage solid tumor |

These agonistic antibodies may have their heavy chain constant region replaced with a heavy chain constant region according to the invention to obtain a higher agonistic activity. Alternatively, an agonistic antibody according to the invention may incorporate an antigen binding fragment of one in the list to form an enhanced agonistic antibody specific for a particular member of the TNF receptor superfamily.

"Immune costimulatory factors" are ligand molecules that provide secondary stimulating signals to activate immune cells. For T-cells, besides the first signal provided by MHC/antigen peptide-T-cells receptor (TCR), their activation further involves the costimulatory factors, including B7/CD28, ICOSL/ICOS, OX40L/OX40, 4-1BBL/4-1BB, etc., to provide costimulatory signals. Activation of B-cells also needs costimulatory factors such as CD40L/CD40 to provide costimulatory signals, in addition to antigen/B-cell receptor (BCR). The ligand molecules in these signaling pathways are immune costimulatory factors. In the context of the present invention, examples of preferred immune costimulatory factors include, but are not limited to B7 (CD80, CD86), ICOSL, OX40L/CD134, 4-1BBL/CD137L, CD40L/CD154, CD30L/CD153, CD27L/CD70 or SLAM family members (CD244, CD150, CD48, CD84, CD319, Ly108, CD229, SLAMF8), etc.

As used herein, "tumor necrosis factor receptor superfamily" and "TNF receptor superfamily" both refer to receptor polypeptides that bind to cytokines of the TNF family. Generally, these receptors are type I transmembrane receptors comprising one or more cysteine-rich repeats in their extracellular domain. Examples of cytokines of TNF family include tumor necrosis factor-α (TNF-α), tumor necrosis factor-β (TNF-β or lymphotoxin), CD30a ligand, CD27a ligand, CD40a ligand, OX-40a ligand, 4-1BB ligand, Apo-1 ligand (also known as Fas ligand or CD95 ligand), Apo-2 ligand (also known as TRAIL), Apo-3 ligand (also known as TWEAK), osteoprotegerin (OPG), APRIL, RANK ligand (also known as TRANCE) and TALL-1 (also known as BlyS, BAFF or THANK). Examples of receptors of the TNF receptor superfamily include type 1 tumor necrosis factor receptor (TNFR1), type 2 tumor necrosis factor receptor (TNFR2), p75 nerve growth factor receptor (NGFR), B-cell surface antigen CD40, T-cell antigen OX-40, Apo-1 receptor (also known as Fas or CD95), Apo-3 receptor (also known as DR3, sw1-1, TRAMP and LARD), receptors called "transmembrane activator and CAML-interactor" or "TACI", BCMA protein, DR4, DR5 (also known as Apo-2; TRAIL-R2, TR6, Tango-63, hAPO8, TRICK2 or KILLER), DR6, DcR1 (also known as TRID, LIT or TRAIL-R3), DcR2 (also known as TRAIL-R4 or TRUNDD), OPCQ DcR3 (also known as TR6 or M68), CAR1, HVEM (also known as ATAR or TR2), GITR, ZTNFR-5, NTR-1, TNFL1, CD30, lymphotoxin β receptor (LTBr), 4-1BB receptor and TR9 (EP988,371 A1). In the context of the present invention, preferred members of TNF receptor superfamily include, but are not limited to CD40, DR5, OX40, CD137, CD27, CD30, GITR, HVEM, TACI, DR4 and FAS, etc.

"Immuno-inhibitory receptors" are such a class of transmembrane glycoproteins that inhibit or block the transmission of activating signals in immune cells. In the context of the invention, examples of immuno-inhibitory receptor include, but are not limited to PD-1, CTLA-4, VISTA, TIM-3, BTLA and LAG-3 etc.

"Immuno-inhibitory ligands" are ligands of immuno-inhibitory receptors, which bind to immuno-inhibitory receptors and activate the downstream inhibitory signals. In the context of the invention, examples of immuno-inhibitory ligand molecules include, but are not limited to PD-L1, PD-L2, B7-H3, B7-H4, VISTA, HVEM and GAL9.

"Immune responses" refers to the biological responses induced against exogenous agents in vertebrates, which protect the subject against damages from these agents or the diseases caused thereby. Immune responses are mediated by actions of immune cells (e.g., T-lymphocytes, B-lymphocytes, natural killer cells (NK), macrophages, eosinophils, mast cells, dendritic cells and neutrophils) and soluble molecules (including antibodies, cytokines and complements) produced by any one of these cells or liver, which lead to selectively targeting, binding, injuring, destroying and/or eliminating of intruding pathogens, cells or tissues infected by pathogens, cancer cells or other abnormal cells, or, in the case of autoimmune diseases or pathological inflammations, normal human cells or tissues.

"Immunotherapy" refers to treatment of a subject having a disease, at risk of a disease or in relapse of a disease by means of inducing, enhancing, inhibiting or modifying corresponding immune responses.

"Enhancing an endogenous immune response" means to enhance efficacy or strength of a native immune response in a subject. Such enhancement of efficacy and potential may be realized via, for example, overcoming the suppression action on endogenous host immunity or stimulating the enhancing action on endogenous host immunity.

"A therapeutically effective amount" or "a therapeutically effective dosage" of a pharmaceutical or a therapeutic agent (such as the fusion proteins or antibodies of the invention) refers to such an amount of said agent that, when used alone or in combination with one or more other therapeutic agent(s), promotes regression of a disease as demonstrated by reduced severity of symptoms, increased frequency and duration of symptom-free period or prevention of disorders or disabilities caused by the disease. "A therapeutically effective amount/dosage" encompasses "a prophylactically effective amount" or "a prophylactically effective dosage". "A prophylactically effective amount" or "a prophylactically effective dosage" of an agent refers to such an amount that, when applied alone or in combination with one or more other therapeutic agent(s) to a subject at risk of a disease or suffering relapse of the disease, precludes occurrence or relapse of the disease. The capability of a therapeutic agent to promote recession or to inhibit progress or relapse of a disease can be determined using various methods known to a skilled on in the art in, for example, clinical trials in human subjects, animal models predictive of effects in human beings or in vitro and ex vivo assays on activity of an agent.

As examples, anticancer agents (pharmaceutical compositions for treating cancers) promote regression of tumor in subjects. In preferred embodiments, a therapeutically effective amount of an agent promotes reduction in cancer cells or even elimination of the cancer. "Promote regression of cancer" means that an agent, when used at a therapeutically effective amount alone or in combination with one or more other anti-neoplastic agent(s), leads to a decrease in tumor growth or size, tumor necrosis, reduced severity of at least one symptom, increased frequency and duration of symptom-free period, prevention of disorders or disabilities caused by the disease, or improvement in symptom in other forms in the patient. Accordingly, for a therapy, "effective" or "effectiveness" comprises both pharmacological effectiveness and physiological safety. Pharmacological effectiveness refers to the capability of an agent to promote regression of cancer in patients. Physiological safety refers to the level of toxicity or other physiologically adverse effects (adverse effects) at the level of cell, organ and/or organism due to administration of the drug.

In the instance of tumor therapy, compared to untreated subjects, a therapeutically effective amount or dosage of an agent preferably inhibits cell growth or tumor growth by at least about 20%, more preferably at least about 40%, even more preferably at least about 60%, further more preferably at least about 80%. In a most preferred example, a therapeutically effective amount or dosage of an agent completely inhibits cell growth or tumor growth, that is, preferably inhibits cell growth or tumor growth by 100%. A compound's capability to inhibit tumor growth can be evaluated in an animal model, such as the MC38 colonic adenocarcinoma model in mouse as described below, which is predictive of antitumor effect in human. Alternatively, as for a composition, said property can be evaluated according to the compound's capability to inhibit cell growth, and such inhibition can be detected in vitro using various methods known to a skilled person in the art. In some other preferred embodiments of the invention, regression of tumor can be observed lasting for a period of at least about 20 days, more preferably at least about 40 days, or even more preferably at least about 60 days.

"Treatment" of or "therapy" for a subject refers to any type of intervention or treatment or administration of an active agent applied on a subject for the purpose of reversing, mitigating, ameliorating, inhibiting, delaying or preventing occurrence, progression, development, deterioration or recurrence of a symptom, a complication, a condition or a biochemical indicia associated with a disease.

In a preferred embodiment of immunotherapy according to the invention, the subject is a human being.

"Cancers" include various diseases characterized by uncontrolled growth of abnormal cells in body. Uncontrolled cell division and growth lead to the formation of malignant tumors or cells. They invade adjacent tissues and can also migrate to distal parts of body through the lymphatic system or blood circulation. In the present invention, "treating cancer" is synonymous to "treating tumor" or "anticancer" or "antitumor".

As said above, the present invention includes use of an antibody or a fusion protein comprising a heavy chain constant region sequence according to the invention for treating proliferative diseases, such as cancers. Cancers are characterized in uncontrolled cell growth that interfere normal functioning of organs and systems in body. Subjects having cancers are those have objectively measurable presence of cancer cells in their body. Subjects at risk of developing cancers are those prone to developing cancers attributable to, for example, family history or genetic predisposition, those exposed to radiation or other agents that are carcinogenic. Cancers that migrate from their primary focuses and implant in vital organs can lead to decline of the affected organs and eventually death. Hematopoietic cancers (such as leukemia) compete with the normal hematopoietic compartments in the subject and cause hematopoietic failure (in forms of anemia, thrombocytopenia and neutropenia), and ultimately lead to death.

The antibodies or fusion proteins comprising a heavy chain constant region sequence according to the invention are useful in treating various cancers or subjects at risk of developing cancers. Examples of such cancers include breast cancer, prostate cancer, lung cancer, ovarian cancer, cervical cancer, skin cancer, melanoma, colon cancer, gastric cancer, liver cancer, esophageal cancer, kidney cancer, pharyngeal cancer, thyroid cancer, pancreatic cancer, testicle cancer, brain cancer, bone cancer and blood cancer (e.g., leukemia, chronic lymphocytic leukemia), etc. In an embodiment of the invention, a vaccine composition according to the invention can be used to treat tumor by stimulating an immune response to inhibit or delay tumor growth or reduce tumor size. Tumor-associated antigens may also be those that are primarily but not exclusively expressed by tumor cells.

In addition, cancers further include, but are not limited to basal cell carcinoma, biliary tract cancer, bladder cancer, bone cancer, cancer in brain and central nervous system (CNS), cervical cancer, choriocarcinoma, colorectal cancer, connective tissue cancer, digestive system cancer, endometrial cancer, esophageal cancer, eye cancer, head and neck cancer, gastric cancer, intraepithelial neoplasm, kidney cancer, laryngeal cancer, liver cancer, lung cancer (small cell, large cell), lymphomas (including Hodgkin Lymphoma and Non-Hodgkin Lymphoma); melanoma; neuroblastoma; oral (e.g. lip, tongue, mouth and pharynx) cancer; ovarian cancer; pancreatic cancer; retinoblastoma; rhabdomyosarcoma; rectal cancer; respiratory cancer; sarcoma; skin cancer; gastric cancer; testicle cancer; thyroid cancer; uterine cancer; urinary system cancer; and other cancers and sarcomas.

"Vaccine" refers to a composition that, when administered alone or in combination with an adjuvant, induces an antigen-specific immune response. This includes protective prophylaxis vaccines and therapeutic vaccines.

Infections that can be treated or prevented with the vaccine compositions of the invention include those of bacteria, viruses, fungi or parasites. In addition, unusual types of infections include scrapie, Bovine Spongiform Encephalopathy (BSE) and prion disease (e.g., kuru disease and Creutzfeldt-Jacob disease) caused by rickettsiae, mycoplasms and pathogens. Examples of bacteria, viruses, fungi or parasites that infect humans are already known. Infections can be acute, subacute, chronic or latent, and it can be local or systemic. Further, infection can be largely intracellular or extracellular during at least one stage of the life cycle of a factor of an infectious organism in the host.

Bacterial infections that can be treated using the vaccine compositions and methods of the invention include Gram-negative and Gram-positive bacteria. Examples of Gram-positive bacteria include, but are not limited to the genus of *Pasteurella*, Staphylococci and Streptococci. Examples of Gram-negative bacteria include, but are not limited to the genus of Escherichiacoli, *Pseudomonas* and *Salmonella*. Specific examples of infectious bacteria include, but are not limited to Heliobacter pyloris, *Borrelia burgdorferi*, *Legionella* pneumophilia, Mycobacteria (e.g., *M. tuberculosis, M. avium*, M. intracellilare, M. kansaii, *M. gordonae*), *Staphylococcus aureus, Neisseria gonorrhoeae, Neisseria meningitidis, Listeria monocytogeners, Streptococcus pyogenes*) (Group A *Streptococcus*), *Streptococcus agalactiae* (Group B *Streptococcus*), *Streptococcus* (grass green group), *Streptococcus faecalis, streptococcus bovis, Streptococcus* (aenorobic spp.), *Streptococcus pneumoniae*, pathogenic *Campylobacter, Enterococcus, Haemophilus influenzae, Bacillus anthracis, Corynebacterium diptheriae, Corynebacterium* sp., Erysipelothrix rhusiopathie, *Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema* pertenue, Leptospira, *Rickettsia* and *Actinomyces israelii*.

Examples of viruses that cause infection in human include, but are not limited to Retroviridae (such as human immunodeficiency virus, e.g., HIV-1(i.e., HTLV-III), HIV-II, LAC or IDLV-II/LAV or HIV-III, and other isolates, such as HIV-LP), Picornaviridae (such as poliovirus, Hepatitis A virus, enteroviruses, human Coxsackie viruses, rhinoviruses, echoviruses), Calciviridae (such as those strains causing gastroenteritis), Togaviridae (such as equine encephalitis viruses, rubella viruses), Flaviviridae (such as dengue viruses, encephalitis viruses, yellow fever viruses), Coronaviridae (such as coronaviruses), Rhabdoviridae (such as vesicular stomata viruses, rabies viruses), Filoviridae (such as Ebola viruses), Paramyxoviridae (such as parainfluenza viruses, mumps viruses, measles virus, respiratory syncytial virus), Orthomyxoviridae (such as influenza viruses), Bungaviridae (such as Hataan viruses, bunga viruses, phleobo viruses and Nairo viruses), Arenaviridae (hemorrhagic fever viruses), Reoviridae (such as reoviruses, orbiviruses, rotaviruses), Bimaviridae, Hepadnaviridae (hepatitis B virus), Parvoviridae (parvoviruses), Papovaviridae (papilloma viruses, polyoma viruses), Adenoviridae (adenoviruses), Herpeviridae (such as herpes simplex virus (HSV) I and II, varicellazoster virus, poxviruses) and Iridoviridae (such as African swine fever virus) and unclassified viruses (such as etiologicagents, Hepatitis D factor, Non-A non-B hepatitis factors (Class 1 intestinal transmission; Class 2 parenteral transmission, such as hepatitis C); Norwalk and related viruses and astroviruses.

Examples of fungi include *Aspergillus, Coccidioides immitis, Cryptococcus neoformans, Candida albicans*) and other *Candida* species, *Blastomyces dermatidis, Histoplasma capsulatum, Chlamydia trachomatis, Nocardia* and *Pneumocystis carinii*.

Parasites include, but are not limited to, blood-borne and/or tissue parasites, such as *Babesia microti*), *Babesia divergans*, Entomoeba *histolytica, Giarda lamblia, Leishmania tropica, Leishmania, Leishmania braziliensis, Leishmania donovdni, Plasmodium falciparum, Plasmodium malariae, Plasmodium ovale, Plasmodium vivax, Toxoplasma gondii, Trypanosoma gambiense, Trypanosoma* rhodesiense (African sleeping sickness), *Trypanosoma cruzi* (Chagus' disease) and *Toxoplasma gondii*, flatworm and roundworms.

"Pharmaceutically acceptable carriers" include any and all physiologically compatible solvents, dispersion media, coatings, antibacterial and antifungal agents, isotonic agents and absorption delaying agents, etc. Preferred are carriers that are suitable for intravenous, intramuscular, subcutaneous, parenteral, spinal or epidermal administration, for example, by injection or infusion.

A pharmaceutical composition/vaccine composition of the invention may be administered in various manners as known in the art. As would be understood, path and/or manner of administration depend on the effect as desired. For administration of a compound according to the invention via certain path, the compound may be coated or co-administered with a material that prevents deactivation. For instance, a compound may be administered to a subject as comprised in a suitable carrier such as liposome or diluent. Pharmaceutically acceptable diluents include saline and aqueous buffers.

Pharmaceutically acceptable carriers include sterile aqueous solutions or dispersions, as well as sterile powders for immediate preparation of sterile injections or dispersions. These media and agents for use with pharmaceutically active substances are well known in the art.

Advantages and features of the present invention will be more apparent from the preferred embodiments as described below in details with reference to the accompanying drawings.

Materials and Methods

Herein below are described some materials and test methods used in the examples. All materials and methods involved herein, whether specified or not, belong to and are available via conventional practices, without need for further details.

1. Antibodies

In the specified examples, the heavy chain variable region sequences and the light chain sequences of the anti-murine CD40 antibodies and DR5 antibodies were as obtained in previous studies (Li F, Ravetch J V. 2011. Inhibitory Fcgamma receptor engagement drives adjuvant and anti-tumor activities of agonistic CD40 antibodies. Science 333: 1030-4; Li F, Ravetch J V. 2012. Apoptotic and antitumor activity of death receptor antibodies require inhibitory Fcgamma receptor engagement. Proc Natl Acad Sci USA 109: 10966-71). The anti-human CD40 heavy chain variable region and light chain sequences were as described in U.S. Pat. No. 7,338,660.

The heavy chain constant region sequences of human IgGs (including human IgG1, IgG2, IgG3 and IgG4 heavy chain constant regions) according to the invention were as obtained in previous studies (Li F, Ravetch J V. 2011. Inhibitory Fcgamma receptor engagement drives adjuvant and anti-tumor activities of agonistic CD40 antibodies. Science 333: 1030-4; Li F, Ravetch J V. 2012. Apoptotic and antitumor activity of death receptor antibodies require inhibitory Fcgamma receptor engagement. Proc Natl Acad Sci USA 109: 10966-71), or otherwise synthesized according to genes. The heavy chain constant region variants of the invention are constructed from said human IgG heavy chain constant region sequences by, for example, site-directed mutagenesis. The antibodies were all expressed in transient transfected HEK 293T cells, and purified from supernatant by Protein G covalently coupled to 90 μm beads of highly cross-linked agarose (Protein G Sepharose® 4 Fast Flow (GE Healthcare)). Mouse and human Control IgG antibodies were purchased from Jackson ImmunoResearch Laboratory.

2. Mice

Fcγ receptor deficient mice, i.e., Fcγ receptor a chain deficient mice (FcgR$^{-/-}$), and mice with humanized Fcγ receptor (FcgR$^{-/-}$hFCGR$^{Tg}$, abbr: hFCGR$^{Tg}$) were as previously reported (Smith P, DiLillo D J, Bournazos S, Li F, Ravetch J V. 2012. Mouse model recapitulating human Fcgamma receptor structural and functional diversity. Proc Natl Acad Sci USA 109: 6181-6). FcγII receptor deficient mice R2$^{-/-}$(FcgR2b$^{-/-}$) and FcγRIIB mice with humanized Fcγ receptor R2$^{-/-}$hR2B$^{Tg}$(FcgR2b$^{-/-}$ hFCGR2B$^{Tg}$) were as previously reported (Li F, Ravetch J V. 2011. Inhibitory Fcgamma receptor engagement drives adjuvant and anti-tumor activities of agonistic CD40 antibodies. Science 333: 1030-4; Li F, Ravetch J V. 2012. Apoptotic and antitumor activity of death receptor antibodies require inhibitory Fcgamma receptor engagement. Proc Natl Acad Sci USA 109: 10966-71). Human CD40-expressing transgenic mice were BAC transgenic mice that express human CD40 (hCD40$^{Tg}$). An hCD40$^+$ mouse and an hFCGR$^{Tg}$ mouse may be crossed to give a mouse with CD40 and Fcγ receptor both humanized (hCD40$^{Tg}$hFCGR$^{Tg}$), or mice expressing hCD40$^+$ and hFCGR$^{Tg}$ other than hFCGR2B$^{Tg}$ (hCD40$^{Tg}$hR2B$^{-/-}$). All the experimental animals were cultured at the Animal Science Experimental Center of Shanghai Jiao Tong University School of Medicine. All experiments were carried out in accordance with laws and regulations and as approved by the Animal Care and Use Committee of Shanghai Jiao Tong University School of Medicine.

3. Enzyme-Linked Immunosorbent Assay (ELISA) for CD40-Binding Capacity of Anti-CD40 Antibodies For assay on anti-human CD40 antibodies, an ELISA plate was coated with recombinant human CD40 protein (Novoprotein Scientific Inc.) overnight at atmospheric temperature, blocked using 1% BSA at room temperature for 2 h, and then washed three times with PBST (0.05% polyoxyethylene (20) sorbitan monolaurate (Tween™ 20) in PBS). To each well was added 100 μL gradient dilutions of the human agonistic CD40 antibody. The plate was incubated at room temperature for 1 h and washed four times with PBST. Then, 100 ng/ml biotinylated secondary antibody against human Igκ light chain was added, incubated at room temperature for 1 h and washed 4 times with PBST. SAV-HRP at an appropriate concentration was added, incubated at room temperature for 1 h. Then, chromogenic substrate was added to react for 5 minutes, and optical absorbance was determined at 650 nm.

For assay on anti-murine CD40 antibodies, the process was the same, expect that the plate was coated with recombinant murine CD40 protein (Novoprotein Scientific Inc.) and HRP-labeled goat anti-human IgG-Fc antibody was used as the secondary antibody.

4, OVA-Specific CD8 Positive T-Cell Amplification Model

Two to four months old mice received adoptive transfer of 2×10$^6$ OT-I spleen cells (CD45.1$^+$) resuspended in 200 μl PBS via tail vein injection, followed by immunization via intraperitoneal injection. The control group received injection of 2 μg DEC-OVA protein and control antibody (Li F, Ravetch J V. 2011. Inhibitory Fcgamma receptor engagement drives adjuvant and anti-tumor activities of agonistic CD40 antibodies. Science 333: 1030-4). The other groups received simultaneous injection of 2 μg DEC-OVA protein and anti-CD40 antibody. Six days later, mouse spleen cells were collected, treated with ACK lysis buffer to remove red blood cells, and resuspended in FACS buffer (PBS supplemented with 0.5% FBS, 2 mM EDTA and 0.1% NaN3) to obtain single-cell suspension of spleen cells. The suspension was assayed for OVA-specific CD8+ T-cell (OT-1) amplification by flow-cytometry staining. The antibodies used include fluorescently labeled antibodies against mouse CD45.1, CD4, CD8 and TCR-Vα2. DAPI staining was used to exclude dead cells in flow-cytometry, and CD45.1$^+$/CD8$^+$/TCR-Vα2$^+$ cells were identified as OT-1/CD8$^+$ T-cells.

5. Stimulation of Mouse Spleen Cells In Vitro

Mouse spleen cells were treated with ACK lysis buffer to lyse red blood cells, then resuspended in spleen cell culture medium (RPMI+10% FBS+1% P/S double antibody). The cells were plated at 2×10$^5$ cells/well, treated with gradient dilutions of agonistic anti-CD40 antibody and incubated at 37° C. for 48 hours. Then, expression of mouse B-cell surface markers of activation (CD80, CD86) was detected by FACS. Expression of the activation markers was measured as mean fluorescence intensity (MFI), which was positively correlated with the activity of agonistic anti-CD40 antibodies in B-cell activation.

6. Simulation of PBMCs In Vitro

PBMCs were isolated from health human subjects by Ficoll. The cells were plated at 2×10$^5$ cells/well, treated with gradient dilutions of agonistic anti-CD40 antibody and incubated at 37° C. for 48 hours. Then, expression of activation markers (CD54, CD80, CD86, HLA-DR) on surface of B-cells in PBMCs was assayed by FACS. Expression of the activation markers was measured as mean fluorescence intensity (MFI), which was positively correlated with the activity of agonistic anti-CD40 antibodies in B-cell activation.

7. ELISA to Profile the Binding Between Antibody and FcγR

The ELISA plate was coated with 100 μL antibody at an appropriate concentration overnight, supernatant being discarded. The plate was blocked with 1% BSA in PBS for 2 hours, followed by washing with PBST (PBS with 0.05% polyoxyethylene (20) sorbitan monolaurate 20 (Tween™ 20)). Then, biotinylated FcγR extracellular domain protein (Sino Biologic Inc., Beijing China) at a concentration as appropriate was added and incubated at room temperature for 1 hour, supernatant being discarded, followed by PBST wash. Streptavidin-HRP (BD Biosciences) was added and incubated at room temperature for 1 hour for detection of biotin protein. After removal of supernatant, developing solution was added to react for 20-40 minutes, and absorbance was determined at 650 nm (A650).

8. Surface Plasmon Resonance

For all surface plasmon resonance (SPR) assays, the buffer system was 10 mM Hepes (pH 7.4), 150 mM NaCl, 3.4 mM EDTA, 0.005% surfactant P20. The experiment was conducted on the Biacore T100 (GE Healthcare) SPR system set to 25° C. At pH 4.5, His-tagged soluble murine FcγR extracellular domain protein (Sino Biologic Inc., Beijing China) was immobilized onto chip CM5 through amine group to the density of 2000 response unites (RUs). Double gradient dilutions of antibody sample at specified concentration was added into the mobile phase at the rate of 30 μL/min. Each cycle consists of 3 minutes of binding followed by 5 minutes of dissociation. At the end of each run, the sensor was regenerated by surface infusion of NaOH at 50 μL/min for 30 seconds. With the Biacore T100 analysis software (Version 1.1, GE Healthcare), after removing the background binding signal from unbound channels, value of the affinity constant KD was calculated using the 1:1 binding dynamic model.

9. MC38 Tumor Model

MO38 is a mouse colon cancer cell line. Two to four months old hFCGR$^{Tg}$ mice were subcutaneously inoculated with 2×10$^6$ MC38 cells. On an interval of three days, tumor size was callipered and tumor volume calculated by (L1$^2$×L2)/2, wherein, L1 was the shortest diameter of the tumor tissue and L2 the longest. Seven days after the inoculation of tumor cells, mice were randomly divided into groups according to tumor size (Day 0), wherein mice of the control group were intraperitoneally injected with 31.6 μg of isotype control IgGs, while the rest 31.6 μg of corresponding antibodies. At Day 3, the treatment of Day 0 was repeated, i.e., the control group was given control IgG while the rest corresponding antibodies. Tumor size was continuously monitored and tumor volume calculated.

10. MO4 Tumor Model

MO4 is a mouse fibrosarcoma cell line. Two to four months old hFCGR$^{Tg}$ mice were subcutaneously inoculated with 2×10$^6$ MO4 cells. Every four days, tumor size was measured with caliper and tumor volume was calculated by (L1$^2$×L2)/2, wherein, L1 was the longest diameter of the tumor tissue and L2 the shortest. Seven days after the inoculation of tumor cells, mice were randomly divided into groups according to tumor size (Day 0), wherein the control group were intraperitoneally injected with 31.6 μg of isotype control IgG and 2 μg of OVA antigen (in form of a fusion protein of antibody DEC205 and OVA) while the rest 31.6 μg of corresponding antibodies and 2 μg of OVA antigen (in the form of a fusion protein of antibody DEC205 and OVA). Tumor size was continuously monitored and tumor volume calculated.

11. Detection of DR5 Binding Capacity for Anti-DR5 Antibodies

To detect the DR5 binding capacity of different anti-DR5 antibodies, MC38 cells were resuspended in ice-cold FACS buffer (PBS+0.5% FBS+2 mM EDTA+0.1%NaN3), to which 3.16-fold gradient dilutions of control and anti-DR5 antibody at concentrations ranging from 2 ng to 20 μg/mL were added, and the reaction was incubated at room temperature for 15 minutes. The system was washed twice with ice-cold FACS buffer, then flow-cytometry stained using FITC-labeled goat anti-human antibody (VECTOR FI-3080) on ice for 25 minutes in dark, which was then washed twice with FACS buffer and analyzed by flow-cytometry. For the antibodies, the DR5 binding capacity was positively correlated to FITC mean fluorescence intensity (MFI). As shown, the anti-DR5 antibodies were comparable to each other on DR5 binding capacity.

12. Pro-Apoptosis Activity Assay on Anti-DR5 Antibodies

To investigate pro-apoptosis activity of anti-DR5 antibodies, the MC38 cells were plated on a flat bottom 96-well plate and incubated overnight. The supernatant was discarded and 100 μL/well fresh medium with or without 10$^6$ murine spleen cells (with red blood cell removed) from FcgR$^{-/-}$, hFCGR$^{Tg}$ mouse (B6 background) were added, and another 100 μL/well fresh medium comprising anti-DR5 antibodies or 1 μg/mL control with or without 1 μg/mL 2B6 antibody and incubated at 37° C. for 4 hours. The 96-well plate was then placed on ice and washed with 200 μL ice-cold PBS after the supernatant being pipetted off. After trypsinization in 100 μL for 3-5 minutes, the reaction was quenched by adding equal volume of complete medium solution. Cells were harvested by centrifugation at 4° C., 400×g, 5 minutes. The obtained cells were subject to flow-cytometry staining using CD45antibody (clone: 30-F11; Biolegend) for surface molecules followed by staining for intracellular activated caspase-3 (antibody clone C92-605; BD Biosciences) and the analyzed by flow-cytometry. MC38 cells were circled according to forward-scattering angle FSC and side-scattering angle SSC as well as CD45 negative. Expression of activated caspase-3 was analyzed. Pro-apoptosis potential was positively correlated to the mean fluorescence intensity (MFI) of the staining of activated caspase-3.

Example 1. Heavy-Chain Constant Region and Agonistic Antibody Comprising Same According to the Invention A series of example heavy chain constant regions were constructed, cloned, expressed and purified as described above, based on which anti-human CD40 or anti-murine CD40 antibodies and anti-murine DR5 antibodies were further constructed.

In brief, in the examples, the heavy chain constant region was divided into two parts for optimization: the CH1-hinge part and the CH2-CH3 part. The CH1-hinge part refers to the segment consisting of the CH1 domain and the hinge region of antibody, and the CH2-CH3 part refers to the segment consisting of the CH2 domain and the CH3 domain of antibody. In specific examples, the CH1-hinge region was non-mutated CH1-hinge region of hIgG1 (SEQ ID NO:1), CH1-hinge region of hIgG2 (SEQ ID NO:2), CH1-hinge region of hIgG3 (SEQ ID NO:3) or CH1-hinge region of hIgG4 (SEQ ID NO:4); the CH2-CH3 domain was non-mutated CH2-CH3 domain of hIgG1 (SEQ ID NO:5), CH2-CH3 domain of hIgG2 (SEQ ID NO:6), CH2-CH3 domain of hIgG3 (SEQ ID NO:7) or CH2-CH3 domain of hIgG4 (SEQ ID NO:8), or was a CH2-CH3 domain comprising amino acid mutation relative to the origin hIgG CH2-CH3 domain, such as the CH2-CH3 domain with the V11 mutation (SEQ ID NO:9) obtained by creating the five mutations of G237D/P238D/H268D/P271G/A330R in the original hIgG1 CH2-CH3 domain and the CH2-CH3 domain with the V9 mutation (SEQ ID NO:10) obtained by creating the four mutations of G237D/P238D/P271G/A330R in the original hIgG1 CH2-CH3 domain.

In examples of heavy chain constant region, the heavy chain constant region sequence was composed from the corresponding CH1-hinge region sequence and CH2-CH3 domain sequence. Example heavy chain constant regions according to the invention are provided in Table 2.

It should be noted that the example heavy chain constant regions in Table 2 were all constructed from human IgGs, and accordingly, hIgG1, hIgG2, hIgG3 and hIgG4 respectively refer to human IgG1, IgG2, IgG3 and IgG4. In Table 2, some sequences comprise mutations in the parenthesis, wherein, the position of amino acid mutation is numbered according to the EU numbering for IgGs.

Description of the heavy chain constant regions in Table 2 is exemplified below. The heavy chain constant region named "GT" comprises the CH1-hinge region from hIgG1 and the CH2-CH3 domain from hIgG1, and accordingly, the sequence of GT is composed of the sequence of the non-mutated CH1-hinge region of hIgG1 and the sequence of the non-mutated CH2-CH3 domain of hIgG1. The heavy chain constant region named "V11 (H2)" (also called "JAC1" herein) comprises the CH1-hinge region from hIgG2 and the CH2-CH3 domain from hIgG1 comprising the mutation of G237D/P238D/H268D/P271G/A330R, and accordingly, the sequence of V11 (H2) (SEQ ID NO: 11) is composed of sequence of the non-mutated CH1-hinge region of hIgG2 and sequence of the hIgG1 CH2-CH3 domain comprising the mutation of G237D/P238D/H268D/P271G/A330R. More heavy chain constant region sequences can be obtained from the sequences in Table 2 and the appended Sequence Listing.

TABLE 2

Example heavy chain constant regions according to the invention

| Name of the heavy chain constant region | Origin of CH1-hinge region | Origin of CH2-CH3 domain (mutation in CH2-CH3 domain) | SEQ ID NO. |
|---|---|---|---|
| G1 | hIgG1 | hIgG1 | |
| G2 | hIgG2 | hIgG2 | |
| G3 | hIgG3 | hIgG3 | |
| G4 | hIgG4 | hIgG4 | |
| V11(H1) | hIgG1 | hIgG1(G237D/P238D/H268D/P271G/A330R) | |
| V9(H1) | hIgG1 | hIgG1(G237D/P238D/P271G/A330R) | |
| V11(H2), i.e. JAC1 | hIgG2 | hIgG1(G237D/P238D/H268D/P271G/A330R) | SEQ ID NO: 11 |
| V9(H2), i.e. JAC2 | hIgG2 | hIgG1(G237D/P238D/P271G/A330R) | SEQ ID NO: 12 |
| V11(H3) | hIgG3 | hIgG1(G237D/P238D/H268D/P271G/A330R) | |
| G3(H2) | hIgG2 | hIgG3 | |
| G2(H3) | hIgG3 | hIgG2 | |
| G1(H2) | hIgG2 | hIgG1 | |
| G1-NA | hIgG1 | hIgG1(N297A) | |
| G2-NA | hIgG2 | hIgG2(N297A) | |
| G2-SELF, i.e. JAC3 | hIgG2 | hIgG2(S267E/L328F) | SEQ ID NO: 13 |
| G2-SE | hIgG2 | hIgG2(S267E) | |
| G2-LF | hIgG2 | hIgG2(L328F) | |
| G2-HDPG, i.e. JAC4 | hIgG2 | hIgG2(H268D/P271G) | SEQ ID NO: 14 |
| G2-PG | hIgG2 | hIgG2(P271G) | |
| G2-HD | hIgG2 | hIgG2(H268D) | |
| G2-GDPDHDPG | hIgG2 | hIgG2(G237D/P238D/H268D/P271G) | |
| G1-SELF | hIgG1 | hIgG1(S267E/L328F) | |
| G1-SDIE | hIgG1 | hIgG1(S239D/I332E) | |
| G1-SE | hIgG1 | hIgG1(S267E) | |
| G1-SDSE | hIgG1 | hIgG1(S239D/S267E) | |
| G1-S236DSE | hIgG1 | hIgG1(S236D/S267E) | |
| G1-GASDALIE | hIgG1 | hIgG1(G236A/S239D/A330L/I332E) | |
| G2-GASDALIE | hIgG2 | hIgG1(G236A/S239D/A330L/I332E) | |
| G2-SDIE | hIgG2 | hIgG1(S239D/I332E) | |

In the described examples, all the obtained antibodies were human antibodies or chimeric antibodies (constant regions being all human originated, anti-human CD40 CDRs being human originated, anti-murine CD40 and anti-murine DR5 CDRs being murine originated), wherein, the human anti-human CD40 or human anti-murine CD40 antibodies and the human anti-murine DR5 antibodies were all based on the heavy chain constant regions of the invention, and were thus identified mainly according to their distinct heavy chain constant regions. Details of example antibodies are provided in Table 3. In the examples, antibodies against the same antigen had the same light chain sequence and the same heavy chain variable region sequence, while their heavy chain constant regions were different. For example, in the examples, human anti-human CD40 antibodies (Anti-hCD40-hIgG) had the same light chain sequence (SEQ ID NO:47) and the same heavy chain variable region sequence. In fact, the light chain sequence and the heavy chain variable region sequence of the anti-human CD40 antibody (Anti-hCD40-hIgG) were identical to the light chain sequence and the heavy chain variable region sequence of the agonistic antibody CP-870893. CP-870893 was first developed by Pfizer as a wholly human IgG2 agonistic antibody specific for hCD40 target for use in immunotherapy of solid tumors and vaccine enhancement. In the examples, the human anti-murine CD40 antibodies (Anti-mCD40-hIgG) had the same light chain sequence (SEQ ID NO:48) and the same heavy chain variable region sequence. In the examples, the human anti-murine DR5 antibodies (Anti-mDR5-hIgG) had the same light chain sequence (SEQ ID NO:49) and the same heavy chain variable region sequence.

It should be noted that some example antibodies can be deemed as fusion proteins composed from separate antibody segments, which retain the structure and configuration of antibody while having functional moieties from different IgG subclasses optionally with amino acid mutation.

In another example, an antigen binding module that specifically binds to an antigen may be fused with a heavy chain constant region according to the invention to give a fusion protein with enhanced activity. For example, a nanobody specifically binding CD40 may be fused with JAC1 to give a fusion protein with enhanced activity.

In further examples, besides a human antibody, the antibody of the invention may also be a chimeric antibody, a humanized antibody etc.

TABLE 3

Details of example antibodies according to the invention

| Name of antibody | antigen | light chain sequence ID | heavy chain sequence ID | Name of heavy chain constant region |
|---|---|---|---|---|
| Anti-mCD40-hIgG1 | murine CD40 | SEQ ID NO: 48 | SEQ ID NO: 15 | G1 |
| Anti-hCD40-hIgG1 | human CD40 | SEQ ID NO: 47 | SEQ ID NO: 16 | G1 |
| Anti-mCD40-hIgG2 | murine CD40 | SEQ ID NO: 48 | SEQ ID NO: 17 | G2 |
| Anti-hCD40-hIgG2 | human CD40 | SEQ ID NO: 47 | SEQ ID NO: 18 | G2 |
| Anti-mCD40-hIgG3 | murine CD40 | SEQ ID NO: 48 | SEQ ID NO: 19 | G3 |
| Anti-hCD40-hIgG3 | human CD40 | SEQ ID NO: 47 | SEQ ID NO: 20 | G3 |
| Anti-mCD40-hIgG4 | murine CD40 | SEQ ID NO: 48 | SEQ ID NO: 21 | G4 |
| Anti-hCD40-hIgG4 | human CD40 | SEQ ID NO: 47 | SEQ ID NO: 22 | G4 |
| Anti-hCD40-hIgG1(V9) | human CD40 | SEQ ID NO: 47 | SEQ ID NO: 23 | V9(H1) |
| Anti-mCD40-hIgG1(V11) | murine CD40 | SEQ ID NO: 48 | SEQ ID NO: 24 | V11(H1) |
| Anti-hCD40-hIgG1(V11) | human CD40 | SEQ ID NO: 47 | SEQ ID NO: 25 | V11(H1) |
| Anti-mCD40-hIgG2(V11) | murine CD40 | SEQ ID NO: 48 | SEQ ID NO: 26 | V11(H2), i.e. JAC1 |
| Anti-hCD40-hIgG2(V11) | human CD40 | SEQ ID NO: 47 | SEQ ID NO: 27 | V11(H2), i.e. JAC1 |
| Anti-mCD40-hIgG3(V11) | murine CD40 | SEQ ID NO: 48 | SEQ ID NO: 28 | V11(H3) |
| Anti-hCD40-hIgG3(V11) | human CD40 | SEQ ID NO: 47 | SEQ ID NO: 29 | V11(H3) |
| Anti-mCD40-hIgG2(H3) | murine CD40 | SEQ ID NO: 48 | SEQ ID NO: 30 | G2(H3) |
| Anti-hCD40-hIgG2(H3) | human CD40 | SEQ ID NO: 47 | SEQ ID NO: 31 | G2(H3) |
| Anti-mCD40-hIgG3(H2) | murine CD40 | SEQ ID NO: 48 | SEQ ID NO: 32 | G3(H2) |
| Anti-hCD40-hIgG3(H2) | human CD40 | SEQ ID NO: 47 | SEQ ID NO: 33 | G3(H2) |
| Anti-mCD40-hIgG1-NA | murine CD40 | SEQ ID NO: 48 | SEQ ID NO: 34 | G1-NA |
| Anti-hCD40-hIgG1-NA | human CD40 | SEQ ID NO: 47 | SEQ ID NO: 35 | G1-NA |
| Anti-mCD40-hIgG2-NA | murine CD40 | SEQ ID NO: 48 | SEQ ID NO: 36 | G2-NA |
| Anti-hCD40-hIgG2-NA | human CD40 | SEQ ID NO: 47 | SEQ ID NO: 37 | G2-NA |
| Anti-hCD40-hIgG2-SE | human CD40 | SEQ ID NO: 47 | SEQ ID NO: 38 | G2-SE |
| Anti-hCD40-hIgG2-LF | human CD40 | SEQ ID NO: 47 | SEQ ID NO: 39 | G2-LF |
| Anti-hCD40-hIgG2-SELF | human CD40 | SEQ ID NO: 47 | SEQ ID NO: 40 | G2-SELF, i.e. JAC3 |
| Anti-hCD40-hIgG2-HD | human CD40 | SEQ ID NO: 47 | SEQ ID NO: 41 | G2-HD |
| Anti-hCD40-hIgG2-PG | human CD40 | SEQ ID NO: 47 | SEQ ID NO: 42 | G2-PG |
| Anti-hCD40-hIgG2-HDPG | human CD40 | SEQ ID NO: 47 | SEQ ID NO: 43 | G2-HDPG, i.e. JAC4 |
| Anti-mDR5-hIgG2 | murine DR5 | SEQ ID NO: 49 | SEQ ID NO: 44 | G2 |
| Anti-mDR5-hIgG1(V11) | murine DR5 | SEQ ID NO: 49 | SEQ ID NO: 45 | V11(H1) |
| Anti-mDR5-IgG2(V11) | murine DR5 | SEQ ID NO: 49 | SEQ ID NO: 46 | V11(H2), i.e. JAC1 |
| Anti-mCD40-hIgG1-SDIE | murine CD40 | SEQ ID NO: 48 | SEQ ID NO: 50 | G1-SDIE |
| Anti-mCD40-hIgG2-SDIE | murine CD40 | SEQ ID NO: 48 | SEQ ID NO: 51 | G1-SDIE |
| Anti-mCD40-hIgG2-GASDALIE | murine CD40 | SEQ ID NO: 48 | SEQ ID NO: 52 | G1-GASDALIE |
| Anti-mCD40-hIgG1 (H2) | murine CD40 | SEQ ID NO: 48 | SEQ ID NO: 53 | G1(H2) |
| Anti-mDR5-hIgG1-GASDALIE | murine DR5 | SEQ ID NO: 49 | SEQ ID NO: 54 | G1-GASDALIE |

Accordingly, it should be understood that the heavy chain constant region sequences in the examples may also be incorporated into agonistic antibodies or fusion proteins other than those exemplified here.

In an example, the heavy chain variable region and the light chain of an antibody specifically binding to an antigen may be fused with a heavy chain constant region according to the invention to give a distinct antibody with enhanced efficacy. For example, the heavy chain variable region and the light chain of any of the agonistic antibodies listed in Table 1 can be combined with JAC1 to give an antibody with enhanced activity against the corresponding TNFR.

Figure 3:
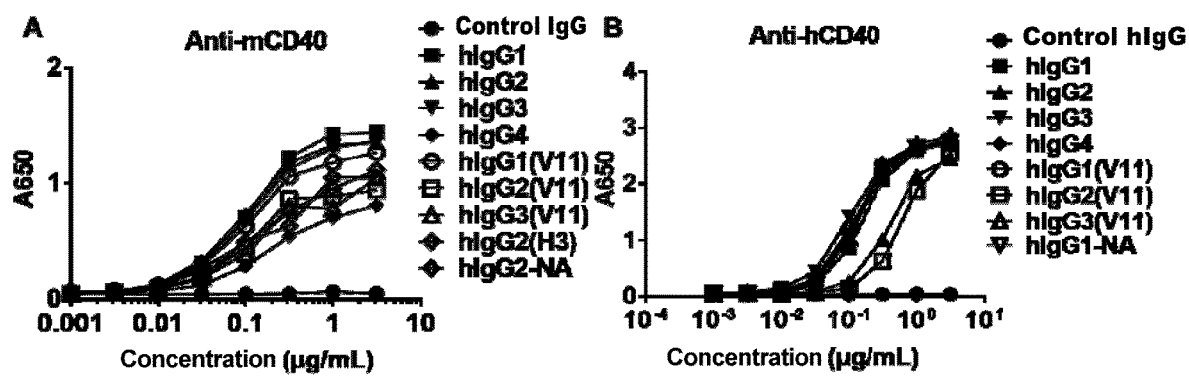
FIG. 3: Antigen binding activity assays. As exhibited, the example agonistic anti-murine CD40 and anti-human CD40 antibodies according to the invention specifically bind to mouse and human CD40 antigens, respectively. The binding between the anti-CD40 antibodies and the CD40 antigens was detected by ELISA. Exhibited are the ELISA signals (A650) generated by the antibodies at gradient dilutions binding to the coating mouse CD40 (A) or human CD40 (B) as detected using human IgG

The example anti-CD40 antibodies according to the invention were tested for CD40 binding capacity by enzyme-linked immunosorbent assay (ELISA) as described above. As shown in FIG. 3, the anti-murine CD40 antibodies (FIG. 3A) and the anti-human CD40 antibodies (FIG. 3B) were all tested for CD40 binding capacity. As shown, the anti-CD40 antibodies as constructed all retained CD40 binding capacity. Notably, as shown by the ELISA, Anti-hCD40-hIgG2 and Anti-hCD40-hIgG2 (V11) exhibited lower binding to hCD40, compared to other variants. However, in view that the low-binding Anti-hCD40-hIgG2 (V11) had prominent performance both in vivo and in vitro, it was concluded that variants of anti-human CD40 antibody (Anti-hCD40-hIgG) have no significant difference in terms of binding capacity for human CD40.

Example 2. Activity of Human IgG Agonistic Antibody Depends on Interaction Between Fc and Fcγ Receptor To investigate whether activity of a human IgG agonistic antibody is regulated by interaction between Fc of the antibody and Fcγ receptor, agonistic anti-murine CD40 antibodies of the four IgG subclasses (hIgG1, hIgG2, hIgG3 and hIgG4), i.e., Anti-mCD40-hIgG1, Anti-mCD40-hIgG2, Anti-mCD40-hIgG3 and Anti-mCD40-hIgG4, were used as model antibodies (FIG. 2A) to first investigate whether their immuno-activating ability is influenced by expression of the Fcγ receptor.

Since agonistic CD40 promotes activation of antigen presenting cells and induces antigen-specific CD8 positive T-cell activation and proliferation, for the agonistic human anti-murine CD40 antibodies (Anti-mCD40-hIgGs), their immuno-activating capability were evaluated through the assay on ability to promote OVA model antigen specific CD8 positive T-cell activation and amplification in OVA immunized mice (Science. 2011 Aug 19; 333(6045):1030-4). In this assay, the mice were first given adoptive transfer of OVA-specific CD8 positive T-cells (OT-I T-cells), and one day later, immunized with antigen DEC-OVA (a fusion protein of OVA and anti-DEC205 antibody, which is an effective means of delivering OVA antigen) and the corresponding anti-CD40 antibody. Six days after immunization, OT-I T-cell proliferation was evaluated.

Figure 4:
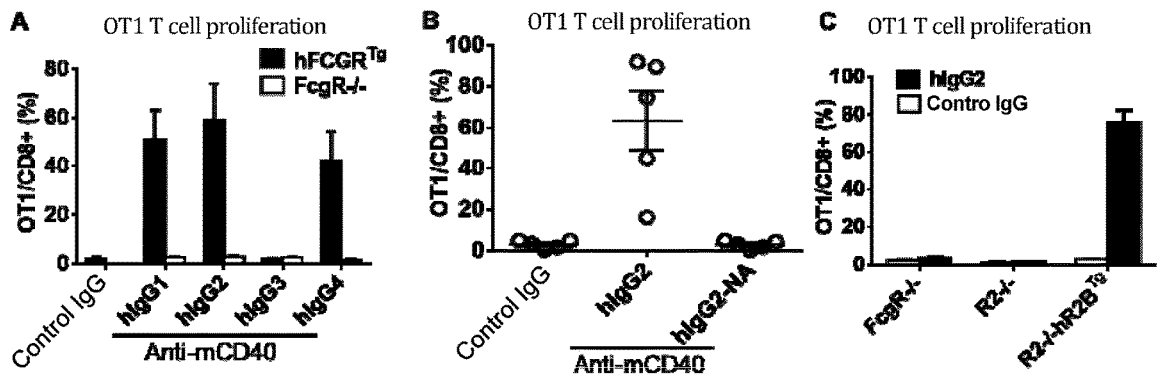
FIG. 4: Activity of different IgG subclasses on the OVA-specific CD8 positive T-cell proliferation model. As exhibited, in vivo activity of agonistic anti-murine CD40 antibodies is specifically dependent on the inhibitory Fcγ receptor. FcγRIIB. The mice were first given adoptive transfer of OVA-specific CD8 positive T-cells (OT-I T-cells, and 1 day later, vaccinated with the model antigen OVA (in the form of DEC-OVA, a fusion protein of OVA and anti-DEC205 antibody, an effective means for delivery OVA antigens) or the control (Ctl IgG) or the anti-CD40 antibodies comprising the specified antibody constant regions. Six days later, proliferation of OT-I T-cells in spleen was detected by flow-cytometry. As indicated by the OT-I T-cell proliferation, the agonistic anti-murine CD40) antibodies enhanced activation and proliferation of OVA model antigen specific CD8 positive T-cells in mice vaccinated with OVA. The anti-murine CD40 antibodies were administered at the dosage of 30 μg/mouse. (A): Activity of the agonistic anti-CD40 antibodies requires involvement of and interaction with Fcγ receptors: (B): The human IgG2 antibody, which does not bind to Fcγ receptors (G2-NA), did not exhibit any immune stimulation activity: (C): The agonistic anti-CD40 antibodies did not exhibit any activity in mice not expressing the inhibitory Fcγ receptor (R2-/-), while in mice expressing humanized inhibitory Fcγ receptor (R2-/-hR2BTg), the inhibitory Fcγ receptor drove the immuno-activation by itself.

As shown in FIG. 4, at the higher dosage (30 µg/mouse), Anti-mCD40-hIgG1, Anti-mCD40-hIgG2 and Anti-mCD40-hIgG4 antibodies were active in mice with humanized Fcγ receptor (hFCGR$^{Tg}$), while under the same condition, Anti-mCD40-hIgG1, Anti-mCD40-hIgG2 and Anti-mCD40-hIgG4 were not observed with apparent activity in Fcγ receptor-deficient mice (FcgR$^{-/-}$) (FIG. 3A). This suggests that activity of agonistic human IgG anti-murine CD40 antibodies requires expression of Fcγ receptor.

To investigate whether the Fcγ receptor binding capacity is necessary for agonistic human IgG anti-murine CD40 antibodies, site-directed mutation (N297A) at the glycosylation site N297 was introduced in the human IgG2 anti-murine CD40 antibody (Anti-mCD40-hIgG2) to give Anti-mCD40-hIgG2-NA. Fc of Anti-mCD40-hIgG2-NA did not to bind to Fcγ receptors (FIG. 6), and Anti-mCD40-hIgG2-NA completely failed to induce OT-I T-cells activation and proliferation in the OVA vaccine model (FIG. 3B). This suggests that the immuno-activating capability of human Anti-mCD40-hIgG2 antibodies depends on the Fcγ receptor binding capacity of Fc of the corresponding antibody.

Example 3. Human Inhibitory Fcγ Receptor (hFcγRIIB) Specifically Interacts with Antibody Fc to Promote Activity of Agonistic Human Anti-CD40 Antibodies To investigate the specific member in the Fcγ receptor family involved in the Fc-Fcγ receptor interaction that entitles the activity of human IgG agonistic antibody, we further studied the contribution from the human inhibitory Fcγ receptor, hFcγRIIB. For mice with humanized inhibitory Fcγ receptor (Fcgr2b$^{-/-}$hFCGR2B$^{Tg}$) and control mice (Fcgr2b$^{-/-}$), Anti-mCD40-hIgG2 antibody was not active in Fcgr2b$^{-/-}$ mice (FIG. 4C), while equivalently active in mice with humanized inhibitory Fcγ receptor (Fcgr2b$^{-/-}$ hFCGR2B$^{Tg}$) (about 80% OT-I CD8$^{+}$, FIG. 4C) and in humanized mice expression wholly human Fcγ receptor (hFCGR$^{Tg}$) (about 60-80% OT-I CD8$^{+}$, FIG. 4A). This suggests that the human inhibitory Fcγ receptor is sufficient to support the activity of Anti-mCD40-hIgG2.

Figure 5:
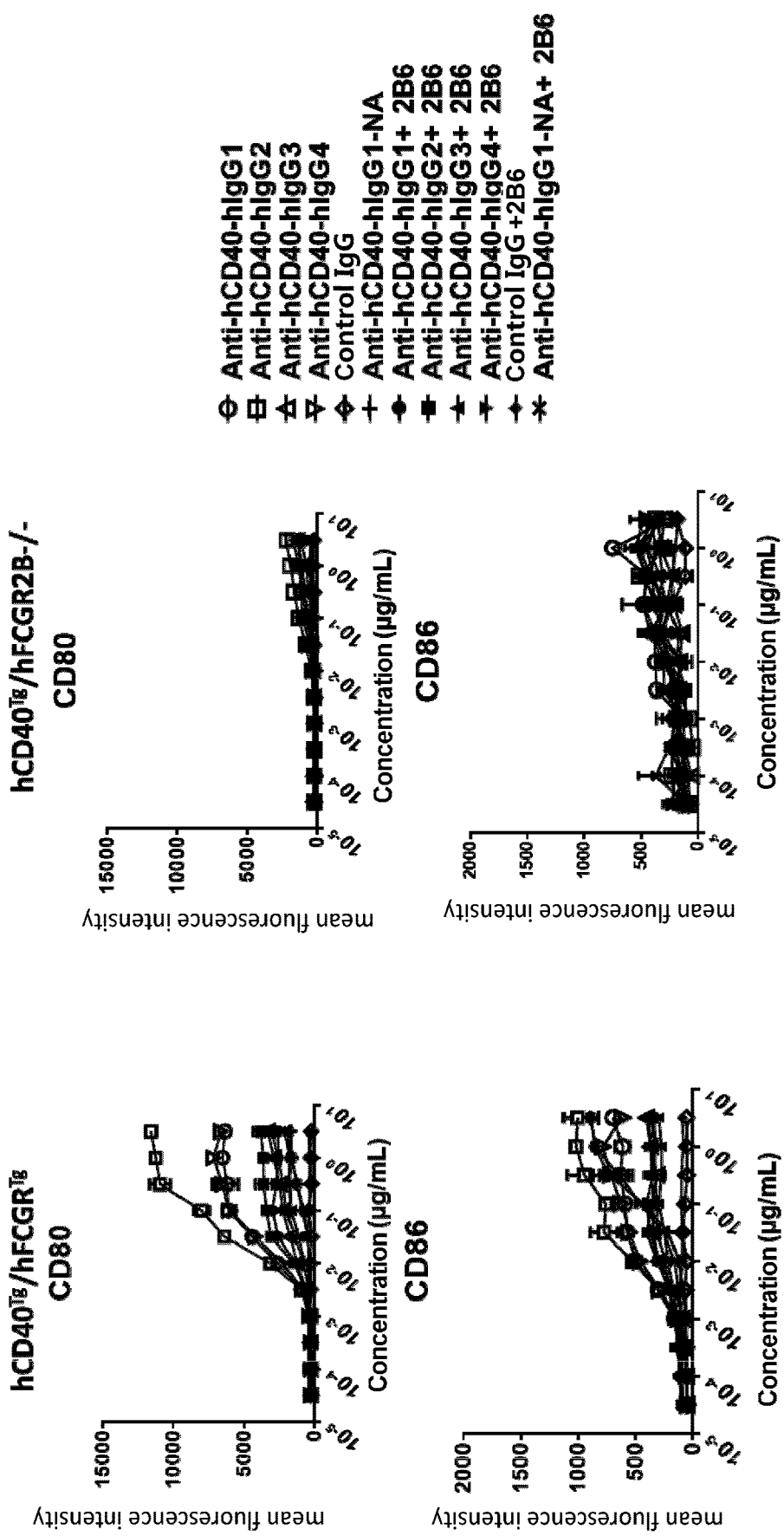
FIG. 5: Mouse spleen cell stimulation in vitro reveals that activity of human agonistic anti-CD40 antibodies is dependent on inhibitory Fcγ receptors in vitro. B-cell activation assay reveals that activity of agonistic anti-human CD40 antibodies is driven by activity of the human inhibitory Fcγ receptor in vivo. Spleen cells were isolated from mice with the specified genotypes (hCD40$^{Tg}$/hFCGR$^{Tg}$: expressing both human CD40 and FcγRs: hCD40$^{Tg}$/hR2B-/-: expressing human CD40 and human Fcγ receptors except for FcγRIIB), incubated in the presence of the control antibodies or the anti-human CD40 antibodies as specified for 48 hours, then assayed by flow-cytometry for expression of B-cell activation makers CD80 and CD86, wherein increase in expression of CD80 and CD86 indicates activity of the corresponding anti-CD40 antibody. 2B6 is a blocking antibody specific for the human inhibitory Fcγ receptor. FcγRIIB.

Meanwhile, when Anti-hCD40-hIgG1, Anti-hCD40-hIgG2, Anti-hCD40-hIgG3, Anti-hCD40-hIgG4 stimulated mouse B-cell and promoted expression of the markers of activation (CD80, CD86) in vitro, different Fcγ receptor environments (hCD40$^{Tg}$hFCGR$^{Tg}$, hCD40$^{Tg}$hR2B$^{-/-}$) significantly impacted activity of the antibodies (FIG. 5). Human Anti-hCD40-hIgG1, Anti-hCD40-hIgG2 and Anti-hCD40-hIgG4 are fairly active in hCD40$^{Tg}$/hFCGR$^{Tg}$, while very weak or even totally inactive in the environment of hCD40$^{Tg}$ hR2B$^{-/-}$. At the same time, antibody 2B6, which is specific for human inhibitory Fcγ receptor (hFcgRIIB), significantly inhibited activity of Anti-hCD40-hIgG antibodies, which suggests that the human inhibitory Fcγ receptor plays a critical roll of positive regulation on activity of human IgG (hIgG1, hIgG2, hIgG4) anti-human CD40 antibodies. This is consistent with the conclusion in study on human IgG (hIgG1, hIgG2, hIgG4) anti-murine CD40 antibodies, which confirms it as a universal observation that the interaction between the human inhibitory Fcγ receptor and Fc of IgG antibodies positively regulates activity of human IgG (hIgG1, hIgG2, hIgG4) anti-CD40 antibodies.

It has been reported elsewhere that an agonistic antibody's agonistic activity relies on its binding to the inhibitory Fcγ receptor. Not just a verification of this finding, the present disclosure further demonstrates that grafting with identical heavy chain constant regions makes agonistic antibodies specific for different antigens tend to have substantially the same Fcγ binding pattern and agonistic activity. For example, as demonstrated in these examples, Anti-mCD40-hIgG2 and Anti-hCD40-hIgG2 have the same heavy chain constant region, while Anti-mCD40-hIgG2 is specific for mCD40 and Anti-hCD40-hIgG2 for hCD40. As seen in the ELISA, the OVA model and the PMBC stimulation assays, Anti-mCD40-hIgG2 and Anti-hCD40-hIgG2 consistently exhibit substantially identical Fcγ binding pattern and agonistic activity. Accordingly, heavy chain constant region is important for optimization of agonistic activity of agonistic antibodies, and a preferred heavy chain constant region can be widely applied to agonistic antibodies with different specificities to provide substantially identical Fcγ binding pattern and agonistic activity. Thus, we conducted a screen among heavy chain constant regions.

Figure 6:
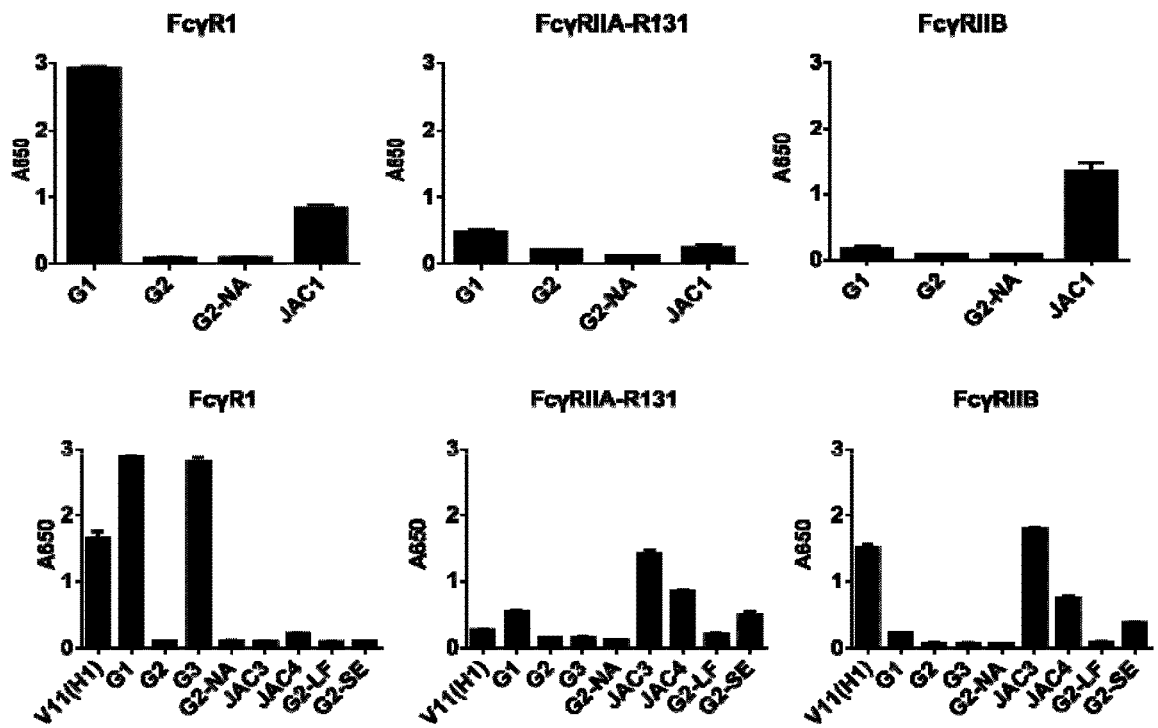
FIG. 6: ELISA of example heavy chain constant regions according to the invention to illustrate different binding profiles of the different heavy chain constant regions (including JAC3 and JAC4) for human Fcγ receptors (FcγRI, FcγRIIA-R131 and FcγRIIB). The ELISA plate was coated with the specified recombinant anti-human CD40 antibodies, binding between the biotinylated human Fcγ receptor molecules and the coating antibodies were detected.

Example 4. Selection of Preferred Human IgG Heavy Chain Constant Region with Superior Binding Capacity and Preference for Human Inhibitory Fcγ Receptor Quite a few studies show that a satisfactorily active agonistic antibody entails not only a high affinity to the FcγRIIB receptor but also a high ratio of affinities for inhibitory Fc receptor: activating Fc receptor (I. A ratio). For the investigation on utilizing the interaction between the human inhibitory Fcγ receptor and IgG antibody Fc that positively regulates activity of human IgG (hIgG1, hIgG2, hIgG4) anti-CD40 antibodies to improve activity of antibodies, we need heavy chain constant region sequences with superior binding capacity and preference for the human inhibitory Fcγ receptor. Though several variants of the human IgG1 heavy chain constant region sequence have be reported with improved binding capacity and preference for the human inhibitory Fcγ receptor, constant region sequences with improved binding capacity and preference for the human inhibitory Fcγ receptor based on heavy chain constant region sequences of other IgG subclasses (hIgG2, 3, 4) remain unknown. Accordingly, screening and analysis are needed. Human IgG heavy chain constant regions' binding capacity for the inhibitory Fcγ receptor was measured by affinity, and the preference for the inhibitory Fcγ receptor was measured by I/A ratio. To select a human IgG (hIgG2, hIgG4) heavy chain constant region with superior binding capacity and preference for the human inhibitory Fcγ receptor, we first compared the candidate heavy chain constant regions or Fc fragments on their binding capacity for human Fcγ receptors (including the inhibitory Fcγ receptor (human FcγRIIB) and the activating Fcγ receptors (including human FcγRI, FcγRIIA, FcγRIIIA, FcγRIIIB)) to pick out those exhibiting higher binding capacity (an affinity equal to or higher than that of human IgG1) and preference (an I/A ratio equal to or higher than that of human IgG1) for the human inhibitory Fcγ receptor. Preferably, the antibody heavy chain constant regions have an affinity to human FcγRIIB 3.2 times or more higher than human IgG1 to human FcγRIIB and an I/A ratio equal to or higher than 0.32; or the antibody heavy chain constant regions have an affinity to human FcγRIIB equal to or higher than human IgG1 to human FcγRIIB and an I/A ratio equal to or higher than 1;

region for their binding capacity for Fcγ receptor, the Fc variants V11 and V9 based on human IgG1 constant region were observed with superior binding capacity and preference for the human inhibitory Fcγ receptor (Table 4). These Fc fragments of heavy chain constant region can be conjugated to another part (e.g., CH1-hinge region) of human IgG heavy chain constant region to obtain candidate human IgG heavy chain constant regions. The whole human IgG heavy chain constant region sequence candidates were further evaluated for their Fcγ receptor binding capacity to see whether these antibodies possess superior binding capacity and preference for the human inhibitory Fcγ receptor. Heavy chain constant regions comprising JAC1 (human IgG2 heavy chain constant region comprising the Fc sequence of V11) and JAC2 (human IgG2 heavy chain constant region comprising the Fc sequence of V9) turned out to be human IgG2 heavy chain constant region sequences with superior binding capacity and preference for the human inhibitory Fcγ receptor (FIG. 6). At the same time, among human IgG2 heavy chain constant region sequence candidates, JAC3 (human IgG2 heavy chain constant region sequence with the mutation of S267E/L328F) and JAC4 (human IgG2 heavy chain constant region sequence with the mutation of H268D/P271G) turned out to be heavy chain constant region sequences with superior binding capacity and preference for the human inhibitory Fcγ receptor (FIG. 6).

TABLE 4

Affinity (KD) of Fc fragments of IgG heavy chain constant region to human Fcγ receptor measured by dissociation constant (KD) detected by surface plasmon resonance assay.

| Fc fragment of antibody | hFcγRI | hFcγRIIA-R 131 | hFcγRIIB | hFcγRIIIA-F 158 | folds of increase in hFcγRIIB binding | I/A ratio* |
|---|---|---|---|---|---|---|
| G1 | $5.2 \times 10^{-9}$ | $1.2 \times 10^{-6}$ | $3.0 \times 10^{-6}$ | $6.7 \times 10^{-6}$ | 1 | 0.40 |
| G2 | not bind | $>10^{-5}$ | $>10^{-5}$ | $>10^{-5}$ | <0.4 | ~1 |
| G1-SE | $2.6 \times 10^{-9}$ | $9.8 \times 10^{-8}$ | $8.3 \times 10^{-8}$ | not bind | 36 | 1.18 |
| G1-SDIE | $2.0 \times 10^{-11}$ | $1.2 \times 10^{-7}$ | $1.7 \times 10^{-7}$ | $3.0 \times 10^{-8}$ | 14 | 0.18 |
| G1-SELF | $3.7 \times 10^{-9}$ | $1.8 \times 10^{-8}$ | $4.3 \times 10^{-8}$ | not bind | 70 | 0.42 |
| V9(H1) | $5.8 \times 10^{-7}$ | $4.1 \times 10^{-6}$ | $9.4 \times 10^{-8}$ | not bind | 32 | 43 |
| V11(H1) | $2.3 \times 10^{-7}$ | $3.8 \times 10^{-6}$ | $1.4 \times 10^{-8}$ | not bind | 94 | 271 |
| G1-GASDALIE | not detected | $6.3 \times 10^{-8}$ | $7.4 \times 10^{-7}$ | $1.0 \times 10^{-7}$ | 1 | 0.09 |

*I/A ratio = [the lower of KD (hFcγRIIA-R131) and KD (hFcγRIIIA-F158)]/KD (hFcγRIIB). In Table 4, the Fc fragments of antibodies are named in accordance with names of the heavy chain constant regions in Table 2; accordingly, it should be understood that the Fc fragment thus named is the one in the heavy chain constant region under the same name in Table 2.

more preferably, the antibody heavy chain constant regions have an affinity to human FcγRIIB 30 times or more higher than human IgG1 to human FcγRIIB and an I/A ratio equal to or higher than 1; more preferably, the antibody heavy chain constant regions have an affinity to human FcγRIIB 60 times or higher than human IgG1 to human FcγRIIB and an I/A ratio equal to or higher than 40; particularly preferred is the antibody heavy chain constant regions having an affinity to human FcγRIIB 90 times or higher than human IgG1 to human FcγRIIB and an I/A ratio equal to or higher than 100.

Candidate heavy chain constant region sequences included naturally occurring human IgG heavy chain constant region sequences, those having one or more site-directed mutations or those having one or more random mutations. Candidate Fc fragments of heavy chain constant region include naturally occurring Fc sequences, those having one or more site-directed mutations or those having one or more random mutations. In the assay on the candidate heavy chain constant regions or Fc fragments of constant According to the method of the invention, more CH1-hinge regions and CH2-CH3 domains can be screened to obtain more human IgG (hIgG2, hIgG4) heavy chain constant regions with superior binding capacity and preference for the human inhibitory Fcγ receptor. Meanwhile, since the preferred heavy chain constant regions according to the invention have higher I/A ratio, which means lower binding to activating Fcγ receptors, agonistic antibodies constructed using these preferred heavy chain constant regions of the invention will be less active in ADCC induction and have less non-specific cytotoxicity.

Figure 7:
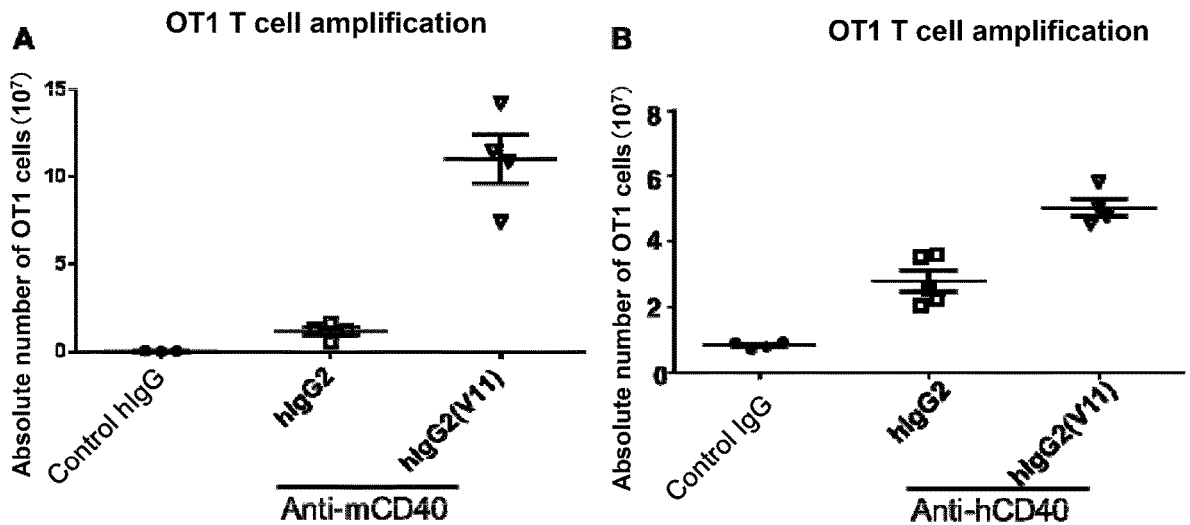
FIG. 7: Activity evaluated on the OVA-specific CD8 positive T-cell proliferation model. Anti-CD40 antibodies comprising the JAC1 sequence were observed with activity superior to the human IgG2 anti-CD40 antibody. The method was the same as for FIG. 4, except that hFCGR$^{Tg}$ mice (A) and hCD40$^{Tg}$/hFCGR$^{Tg}$ mice (B) were used and the dosage of anti-CD40 antibodies was 10 μg/mouse. Numbers of OT-I T-cells are detected, which indicates activity of the anti-CD40 antibodies to induce activation and proliferation of OT-I T-cells.

Example 5. Human IgG Heavy Chain Constant Regions with Superior Binding Capacity and Preference for the Human Inhibitory Fcγ Receptor (hFcγRIIB) Support Stronger Activity of Agonistic Anti-CD40 Antibody To investigate whether the human IgG (hIgG2, hIgG4) heavy chain constant regions with superior binding capacity and preference for the human inhibitory Fcγ receptor (hFcγRIIB) support enhanced agonistic anti-CD40 antibody activity, the anti-murine CD40 antibody and the anti-human CD40 antibody comprising JAC1 heavy chain constant region (i.e., Anti-mCD40-hIgG2(V11) and Anti-hCD40-hIgG2(V11)) were tested in the OVA vaccine model for activity to induce activation and proliferation of OT-I T-cells. As shown, Anti-mCD40-hIgG2(V11) is significantly superior to Anti-mCD40-hIgG2 (FIG. 7A), and Anti-hCD40-hIgG2(V11) is significantly superior to Anti-hCD40-hIgG2 (FIG. 7B), as demonstrated by enhanced capability of immune stimulation. As demonstrated, the absolute number of OT1 cells and the percentage of CD8+ T-cells are significantly increased. Meanwhile, the anti-human CD40 antibodies comprising JAC3 and JAC4 (Anti-hCD40-hIgG2-SELF, Anti-hCD40-hIgG2-HDPG) were tested for activity of B-cell activation. As shown, Anti-hCD40-hIgG2-SELF and Anti-hCD40-hIgG2-HDPG are significantly superior to human IgG2antibody (FIG. 8), as demonstrated by increased expression of the surface activation molecule CD86 by stimulated mouse B-cells and increased expression of the surface activation molecule CD54 by stimulated human B-cells. These results prove that human IgG (hIgG2, hIgG4) heavy chain constant regions having superior binding capacity and preference for the human inhibitory Fcγ receptor (hFcγRIIB) support enhanced agonistic anti-CD40 antibody activity.

Example 6. CH1-Hinge Region Regulates Activity of Agonistic Human IgG Anti-CD40 Antibody In the activity test on agonistic human IgG anti-CD40 antibody at low dosage (10 μg/mouse), among Anti-mCD40-hIgG1, Anti-mCD40-hIgG2, Anti-mCD40-hIgG3 and Anti-mCD40-hIgG4, Anti-mCD40-hIgG2 exhibited the highest activity in Fcγ receptor humanized mice (hFCGR$^{Tg}$) while Anti-mCD40-hIgG3 the lowest (FIG. 9A). To investigate whether the CH1-hinge region of human IgG antibodies regulates activity of the agonistic human IgG anti-CD40 antibodies, the CH1-hinge region of human IgG2 antibody was replaced with the CH1-hinge region of human IgG3. The obtained agonistic human IgG2 anti-murine CD40 antibody (Anti-mCD40-hIgG2(H3)) lost the immuno-stimulatory activity (FIG. 9B). This indicates that CH1-hinge regions are able to regulate activity of agonistic human IgG anti-CD40 antibodies.

Example 7. Human IgG2 Hinge Region Supports Higher Activity of Agonistic Human IgG Anti-CD40 Antibody than Hinge Regions from IgG1 and IgG3

Figure 10:
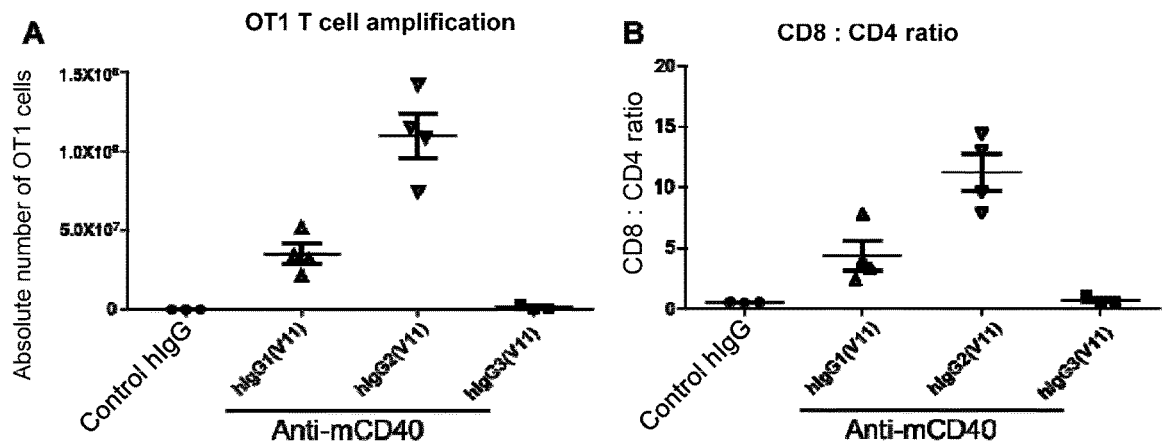
FIG. 10: The CH1-hinge region from human IgG2 is more supportive than the CH1-hinge regions from IgG1 and IgG3 for the immuno-agonistic activity of the anti-CD40 antibodies in the OVA vaccine model. The method was the same as for FIG. 4 and FIG. 7, wherein the specified different anti-murine CD40 antibodies were evaluated for their activity in hFCGR$^{Tg}$ mice using the OVA vaccine model. Proliferation of OT-I T-cells (A) and the CD8:CD4 ratio (B) were detected to indicate activity of the anti-CD40 antibodies. The dosage of antibody was 10 μg/mouse.

To compare the CH1-hinge segments from human IgG1, 2 and 3 on their capability to support activity of agonistic human IgG anti-CD40 antibodies, anti-CD40 antibodies comprising the same Fc and different CH1-hinge regions were prepared. As the activity test showed, their performances were significantly different, wherein, the antibody having the CH1-hinge region from human IgG2 (Anti-mCD40-hIgG2(V11)) was the most active, followed by the antibody having the CH1-hinge region from human IgG1 (Anti-mCD40-hIgG1(V11)), and the antibody having the CH1-hinge region from human IgG3 (Anti-mCD40-hIgG3 (V11)) had the lowest activity (FIG. 10). This indicates that human IgG2 hinge region supports higher activity of agonistic human IgG anti-CD40 antibodies than hinge regions from IgG1 and IgG3.

Figure 11:
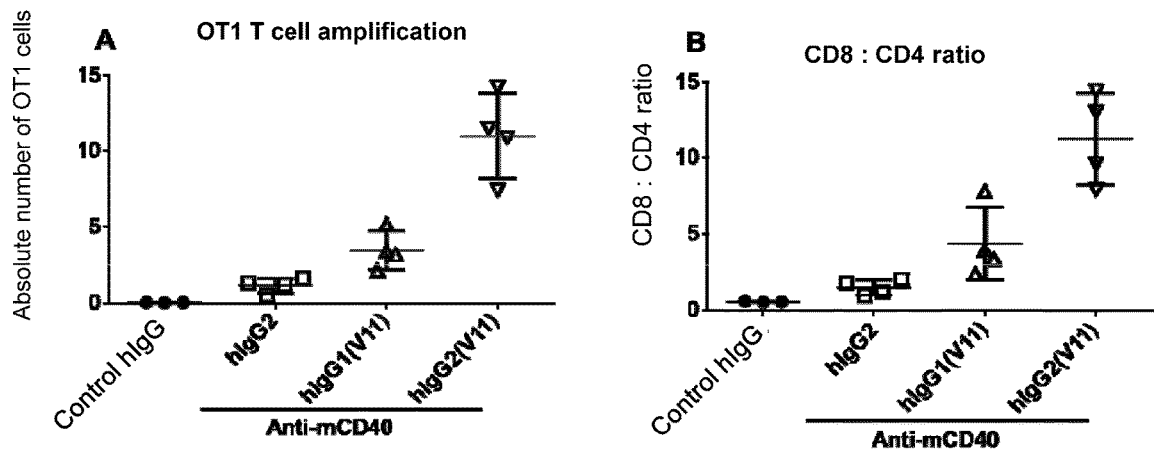
FIG. 11: The anti-murine CD40 antibody comprising JAC1 (Anti-mCD40-hIgG2 (V11)) was observed with activity superior to the human IgG2 antibody (Anti-mCD40-hIgG2) and the anti-murine CD40 antibody comprising V11 (H1) (Anti-mCD40-hIgG1 (V11)) in the OVA vaccine model. The method was the same as for FIG. 4 and FIG. 7, wherein the specified different anti-murine CD40) antibodies were evaluated for their activity in hFCGR$^{Tg}$ mice using the OVA vaccine model. Proliferation of OT-I T-cells (A) and the CD8: CD4 ratio (B) were detected to indicate activity of the anti-CD40 antibodies. The dosage of antibody was 10 μg/mouse.
Figure 12:
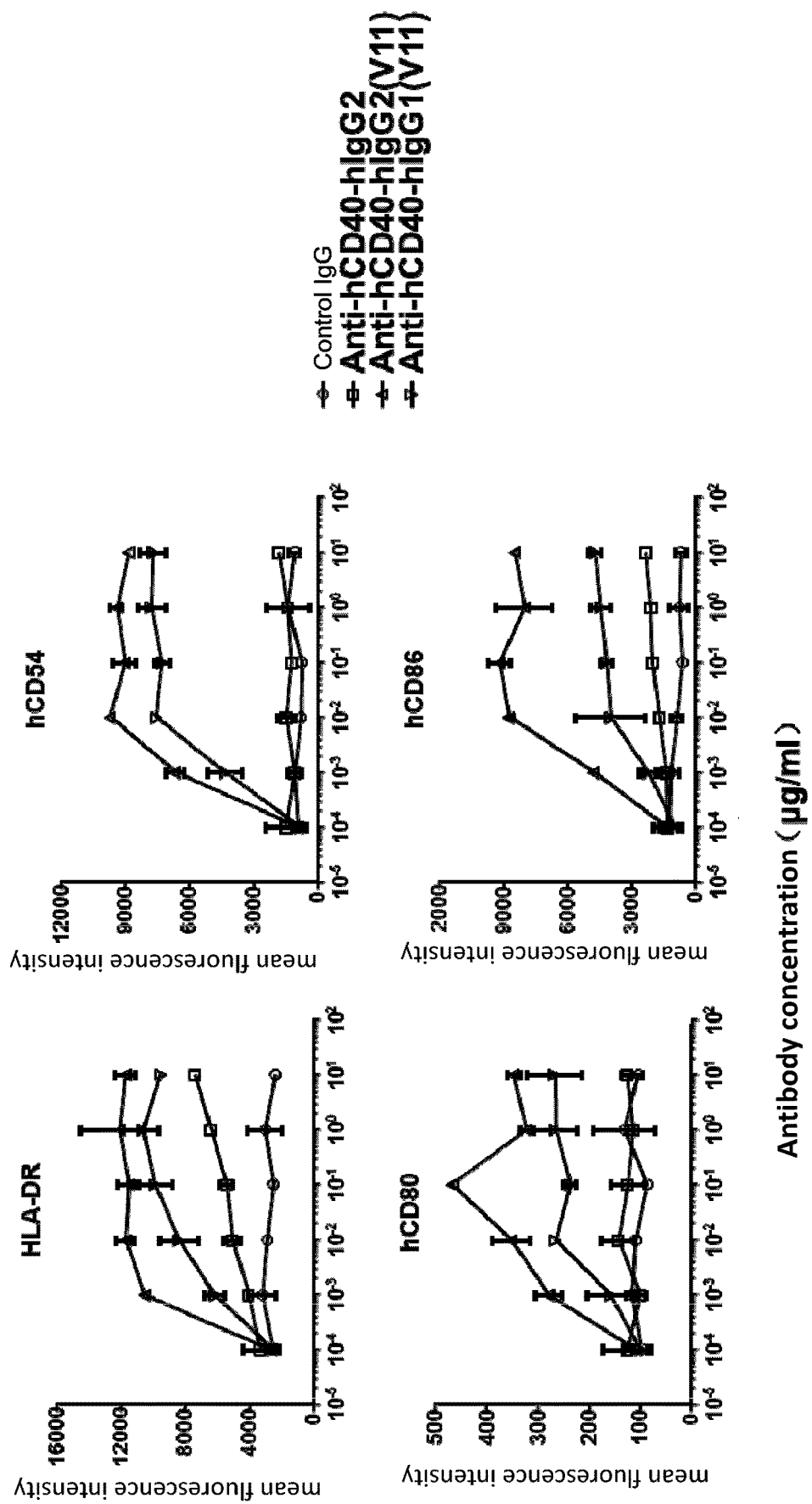
FIG. 12: In PBMC stimulation in vitro assay, the anti-human CD40 antibody comprising JAC1 (Anti-hCD40-hIgG2 (V11)) was observed with activity superior to the human IgG2 antibody (Anti-hCD40-hIgG2) and the anti-human CD40 antibody comprising V11 (H1) (Anti-hCD40-hIgG1 (V11)).

Example 8. Preferred Human IgG2 Hinge Region and Fc Having Superior Binding Capacity and Preference for the Human Inhibitory Fcγ Receptor Synergistically Enhance Activity of Agonistic Human IgG Anti-CD40 Antibody Since both the human Fc fragment and the CH1-hinge segment impact activity of the agonistic human IgG anti-CD40 antibodies, we think it necessary to investigate whether the Fc having superior binding capacity and preference for the human inhibitory Fcγ receptor plus the preferred CH1-hinge region would further increase activity of the agonistic human IgG anti-CD40 antibodies. Activity of the followings were compared: the variant of human IgG1antibody having the highest binding capacity and preference for the human inhibitory Fcγ receptor (Anti-mCD40-hIgG1(V11), i.e., the V11 variant of human IgG1), the human IgG2 antibody having the best CH1-hinge region (Anti-mCD40-hIgG2) and the antibody with the combined Fcγ receptor binding capacity of V11 and the CH1-hinge region from IgG2 (JAC1) (Anti-mCD40-hIgG2 (V11)). As shown, Anti-mCD40-hIgG2 (V11) comprising the combined Fc optimization and CH1-hinge region optimization exhibited the highest activity, as demonstrated by increased absolute number of OT-1 cells and percentage of CD8$^+$ T-cells in the OVA vaccine model (FIG. 11). At the same time, PMBC stimulation test was conducted to compare Anti-hCD40-hIgG1(V11), Anti-hCD40-hIgG2 and Anti-hCD40-hIgG2 (V11) on immuno-stimulatory activity (FIG. 12), wherein, it was also Anti-hCD40-hIgG2 (V11) comprising the combined Fc optimization and CH1-hinge region optimization that exhibited the highest activity.

The increased activity observed with hIgG2 (V11) is more than addition of the activity of hIgG1(V11) alone and the activity of hIgG2 alone. This suggests that preferred human IgG2 CH1-hinge region and Fc having higher binding capacity and preference for the human inhibitory Fcγ receptor synergistically provide enhanced activity in different agonistic human IgG antibodies.

Figure 13:
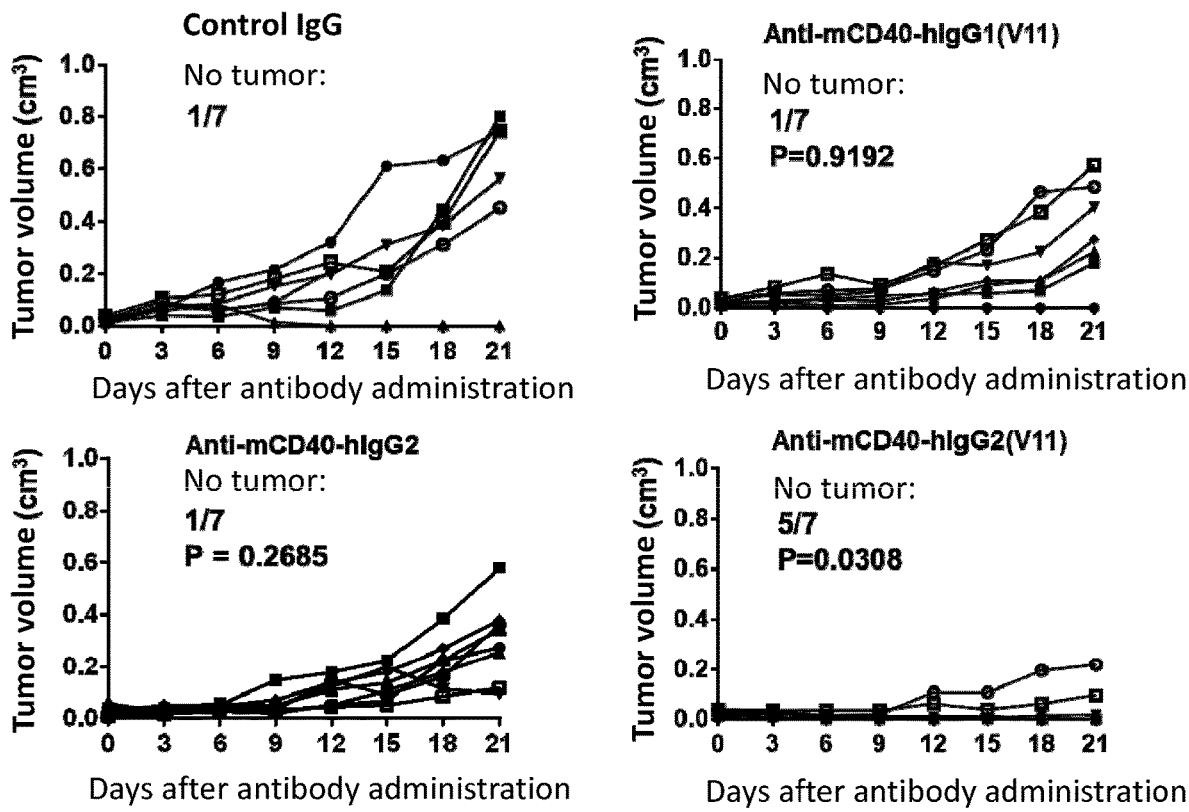
FIG. 13: Curves of MC38 tumor growth indicate that the anti-murine CD40 antibody comprising JAC1 (Anti-mCD40-hIgG2 (V11)) exhibited activity superior to the human IgG2 antibody (Anti-mCD40-hIgG2) and the anti-murine CD40) antibody comprising V11 (H1) (Anti-mCD40-hIgG1 (V11)) in the MC38 tumor model. The hFCGR$^{Tg}$ mice were subcutaneously transplanted with MC38 tumor cells at Day 0. After tumor formation, the animals were treated via intraperitoneal injection of the specified antibodies at Day 7 and Day 10, at the dosage of 31.6 μg/mouse each time. Change in tumor volume was monitored (7 mice/group).
Figure 14:
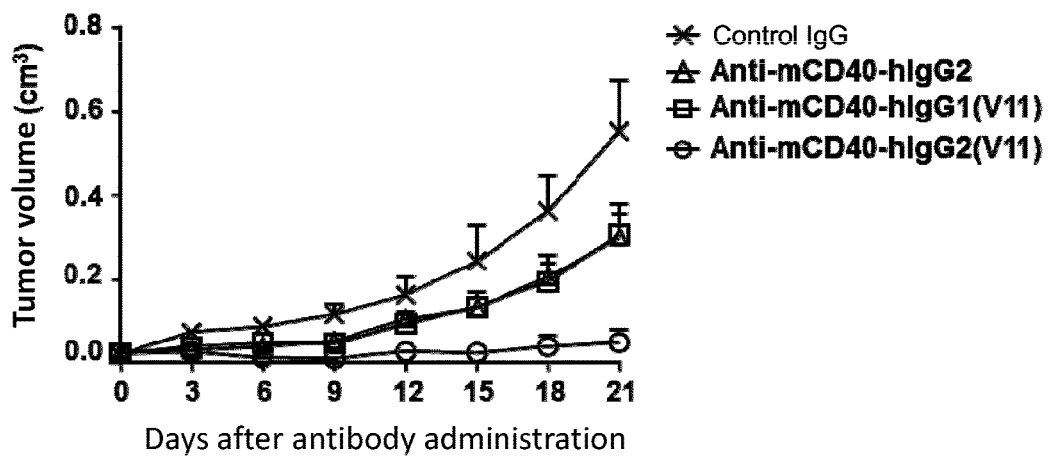
FIG. 14: Another representation of the results in the experiments of FIG. 13.

The three antibodies, i.e., Anti-mCD40-hIgG1(V11), Anti-mCD40-hIgG2 and Anti-mCD40-hIgG2 (V11), were further tested for antitumor activity in the MC38 tumor model (as described in the part of Materials and Methods above). As seen, Anti-mCD40-hIgG2 (V11) significantly outperformed Anti-mCD40-hIgG1(V11) and Anti-mCD40-hIgG2 in antitumor activity (FIG. 13, 14). In the group treated with Anti-mCD40-hIgG2 (V11), 5 out of 7 were observed with complete elimination of tumor in vivo, which indicates an excellent response to the antitumor therapy.

Figure 15:
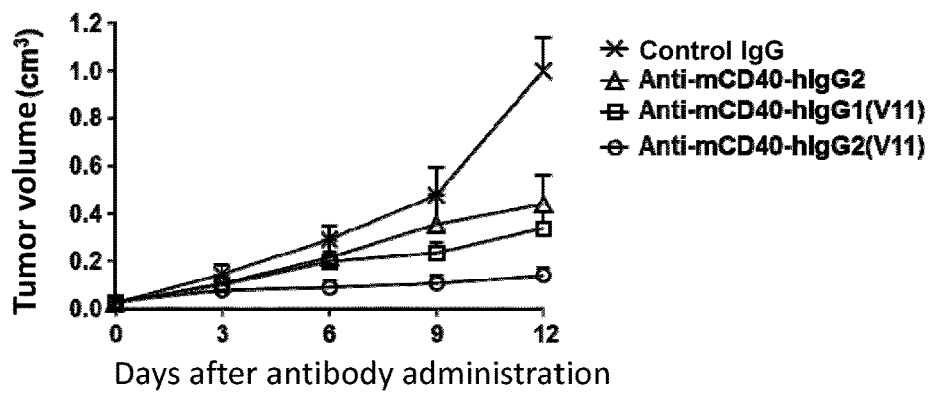
FIG. 15: Curves of MO4 tumor growth indicate that the anti-murine CD40 antibody comprising JAC1 (Anti-mCD40-hIgG2 (V11)) exhibited activity superior to the human IgG2 antibody (Anti-mCD40-hIgG2) and the anti-murine CD40) antibody comprising V11 (H1) (Anti-mCD40-hIgG1 (V11)) in the MO4 mouse fibrosarcoma model. The hFCGR$^{Tg}$ mice were subcutaneously transplanted with MO4 tumor cells at Day 0. After tumor formation, the animals were treated via intraperitoneal injection of the specified antibodies and the model antigen OVA (in the form of a fusion protein of OVA and anti-DEC205 antibody) at Day 7 and Day 10. The dosage was 31.6 μg/mouse for the antibodies and 2 μg/mouse for the model antigen OVA. Change in tumor volume was monitored.

Similarly, the three antibodies, i.e., Anti-mCD40-hIgG1 (V11), Anti-mCD40-hIgG2 and Anti-mCD40-hIgG2 (V11), were further tested for antitumor activity in the MO4 tumor model (as described in the part of Materials and Methods above). As seen, also in this model, Anti-mCD40-hIgG2 (V11) significantly outperforms Anti-mCD40-hIgG1(V11) and Anti-mCD40-hIgG2 antibody in antitumor activity (FIG. 15).

Figure 16:
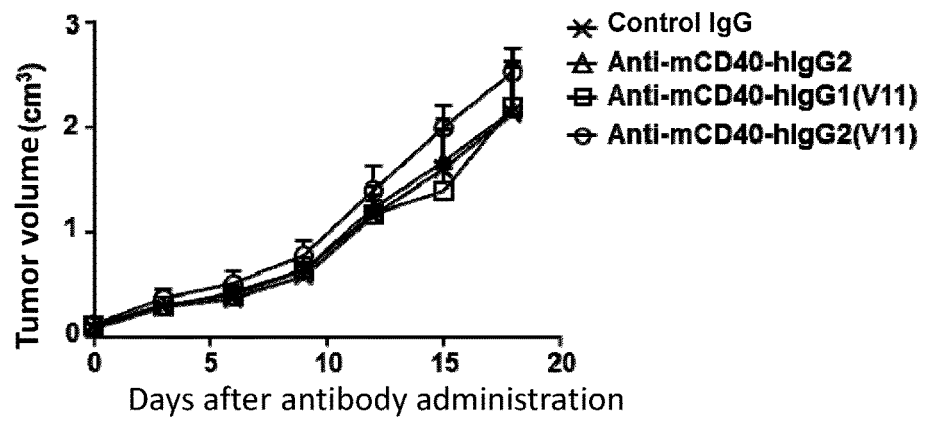
FIG. 16: Curves of MC38 tumor growth indicate that the agonistic anti-murine CD40 antibodies have no antitumor activity in IgG Fc receptor-knocked out mice (FcγR$^{-/-}$).

These antitumor activity results are substantially consistent with the results observed in the OVA vaccine model (FIG. 11). Further, all the three antibodies, i.e., Anti-mCD40-hIgG1(V11), Anti-mCD40-hIgG2 and Anti-mCD40-hIgG2 (V11), exhibited no antitumor activity in MC38 tumor model in Fc receptor-knocked out mice (FcγR−/−) (FIG. 16). This suggests that Fcγ receptor binding is essential to antitumor activity of the agonistic antibodies, and that the heavy chain constant regions of the invention, such as G2(VII), also known as JAC1, can improve not only the adjuvant activity of the human IgG anti-CD40 antibody in vaccine but also antitumor activity of the antibody.

Figure 17:
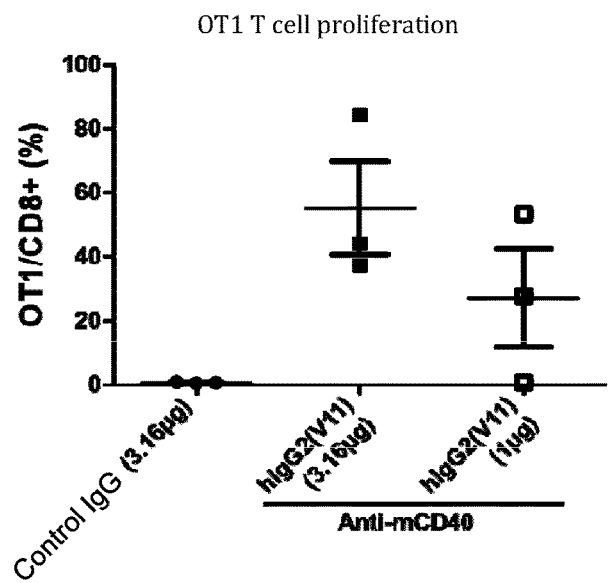
FIG. 17: The anti-murine CD40 antibody comprising JAC1 (Anti-mCD40-hIgG2 (V11)) are active at low dosages in the OVA vaccine model. The method was the same as for FIG. 4 and FIG. 7, wherein the control and the JAC1 anti-murine CD40 antibody were tested for activity at the specified dosages in hFCGR$^{Tg}$ mice using the OVA vaccine model. Proliferation of OT-I T-cells indicates activity of the anti-CD40 antibodies.

Further, as seen in the OVA vaccine model, Anti-mCD40-hIgG2 (V11) exhibited significant activity at the dosage of 3.16 μg/mouse and the dosage of 1 μg/mouse (FIG. 17), while Anti-mCD40-IgG1antibody became no more active at the dosage of 10 μg/mouse (FIG. 9A).

Figure 18:
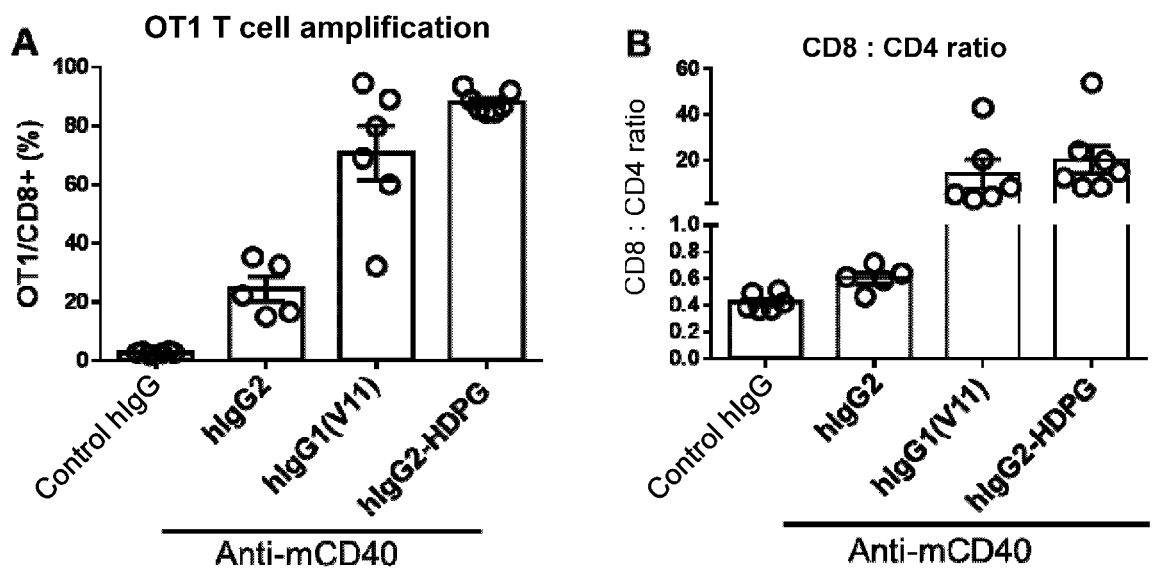
FIG. 18: The anti-murine CD40 antibody comprising JAC4 exhibited stronger agonistic activity in the OVA vaccine model. The method was the same as for FIG. 4 and FIG. 7, wherein the specified different anti-murine CD40 antibodies were tested for activity in hFCGR$^{Tg}$ mice using the OVA vaccine model. Proliferation of OT-I T-cells indicates activity of the anti-CD40 antibodies.

The OVA vaccine model was further used to compare the anti-CD40 antibody comprising the JAC4 sequence (Anti-mCD40-hIgG2-HDPG) and the non-mutated IgG2anti-CD40 antibody (Anti-mCD40-hIgG2) on their immuno-agonistic activity. As shown, Anti-mCD40-hIgG2-HDPG is significantly superior to Anti-mCD40-hIgG2, as demonstrated by the significant increase in the percentage of OT-I cells in CD8$^+$ T-cells and the percentage of CD8+ T-cells (FIG. 18). Meanwhile, Anti-mCD40-hIgG2-HDPG's activity is at least equivalent to Anti-mCD40-hIgG1 (V11), or higher (FIG. 18).

Accordingly, agonistic anti-CD40 antibodies constructed based on the heavy chain constant regions of the invention (e.g., JAC1 or JAC4) have superior immuno-stimulatory activity and antitumor activity, while their minimal effective dosage is only ⅒ that of the IgG1-based agonistic antibodies under development, or even lower. This indicates that they have higher activity, broader effective dosage range and improved safety, which allows development into antitumor therapeutics or vaccine adjuvants to improve the immunological efficacy of vaccines against tumor or infectious diseases.

Figure 19:
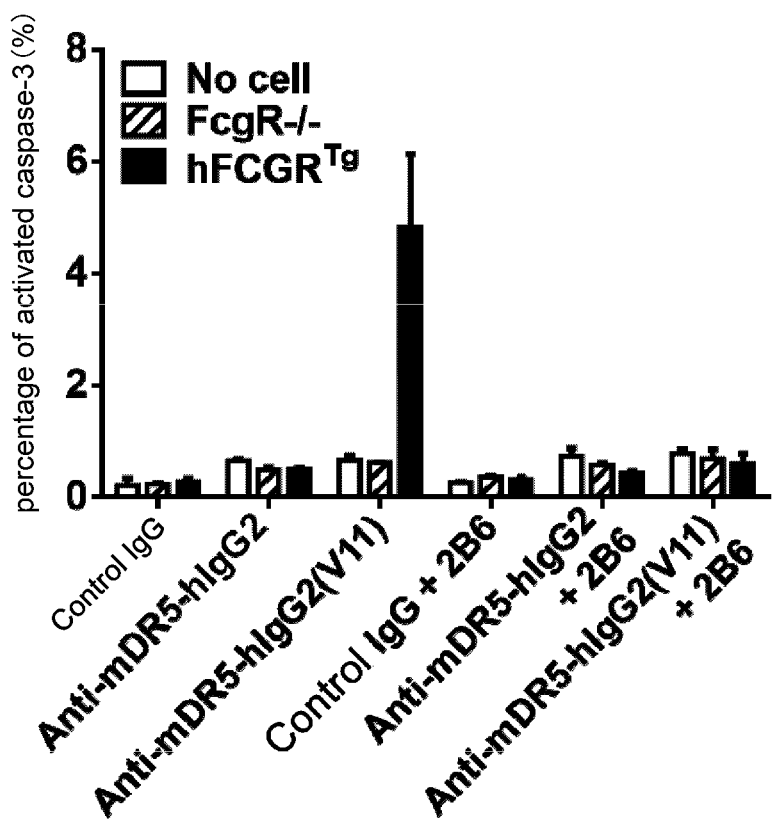
FIG. 19: The anti-human DR5 antibody comprising JAC1 was observed with stronger pro-apoptosis potential. The ability of the antibody in supporting the activity of anti-DR5 antibodies is stronger than human IgG2 and is dependent on the human inhibitory Fcγ receptor. MC38 cells were treated with the control and the different anti-murine DR5 antibodies in the absence and the presence of mouse spleen cells of the specified genotypes (FcgR–/– or hFCGR$^{Tg}$) and in the presence or absence of the antibody 2B6 specifically blocking the human inhibitory Fcγ receptor. Activation of Caspase-3 in the MC38 cells were evaluated (Activated caspase-3 (%), indicating the activity of the anti-DR5 antibodies to activate the apoptosis singling downstream to DR5).

Example 9. Preferred Human IgG2 CH1-Hinge Region and Fc Having Superior Binding Capacity and Preference for the Human Inhibitory Fcγ Receptor Synergistically Provide Enhanced and Additional Activity of Agonistic Human IgG Antibodies To investigate the impact of Fcγ receptor binding on activity of other human agonistic antibodies and whether preferred human IgG2 CH1-hinge region in combination with Fc having superior binding capacity and preference for the human inhibitory Fcγ receptor synergistically enhance activity of other agonistic human IgG antibodies, agonistic anti-DR5 antibodies (Anti-mDR5-IgG) comprising different CH1-hinge regions and Fc fragments were prepared and tested for their activity to induce apoptosis of MC38 cells. As shown, human IgG2 anti-DR5 antibody(Anti-mDR5-IgG2) was inactive, while anti-DR5 antibody(Anti-mDR5-IgG2(V11)), which comprises the JAC1 sequence, was active only in the presence of expression of Fcγ receptor (hFCGR$^{Tg}$) (FIG. 19). And, this activity could be completely blocked by antibody 2B6 specific for the human inhibitory Fcγ receptor. These suggest that activity of the anti-DR5 antibody with the JAC1 sequence (Anti-mDR5-IgG2(V11)) is specifically regulated by the interaction with the human inhibitory Fcγ receptor and that the agonistic anti-DR5 antibodies are subject to the same mechanism of regulation on activity as the anti-CD40 antibodies. Accordingly, the preferred human IgG2 CH1-hinge region in combination with the Fc having superior binding capacity and preference for the human inhibitory Fcγ receptor provides the agonistic human IgG anti-DR5 antibody with enhanced activity.

Figure 20:
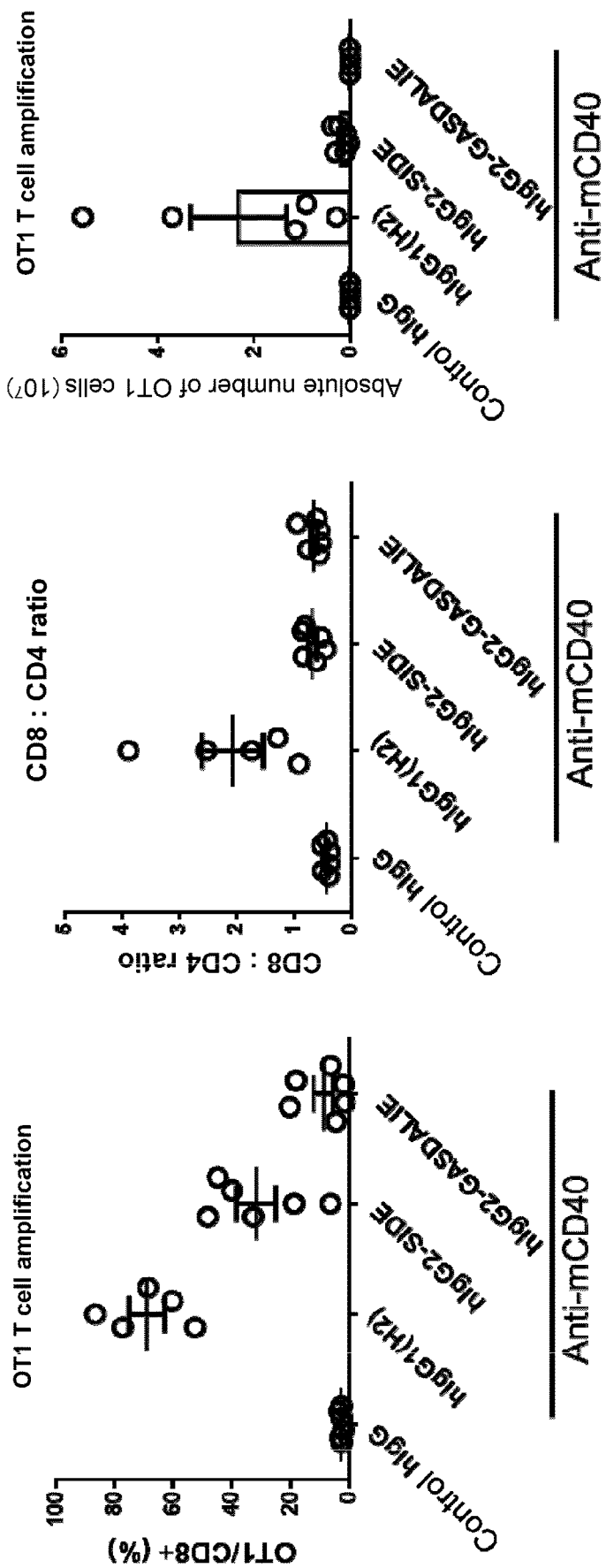
FIG. 20: Increased binding capacity for activating Fcγ receptor (decreased I/A ratio) reduces agonistic anti-CD40 activity. As seen in the figure, the variant anti-mCD40-hIgG1-SDIE and the variant anti-mCD40-hIgG1-GAS-DALIE exhibited higher binding capacity for activating Fcγ receptor and thus a lower I/A ratio. Their immuno-activating activity in vivo were lower than anti-mCD40-G1 (H2) which has a higher I/A ratio, as demonstrated by the significantly decreased percentage of OT1 cells and absolute number of OT1 cells, as well as percentage of CD8+T-cells. This suggests that binding capacity to activating Fcγ receptors significantly impact activity of antibodies.

Example 10. A Preferred Antibody Constant Region not Only Requires a Preferred Human IgG2 CH1-Hinge Region and an Fc with Superior Binding Capacity for the Human Inhibitory Fcγ Receptor but Also Requires the Fc to have Increased Binding Preference for the Human Inhibitory Fcγ Receptor, i.e., a Higher I/A Ratio To investigate the impact of human inhibitory Fcγ receptor binding preference on the agonistic activity of antibody heavy chain constant regions with enhanced binding capacity for the inhibitory Fcγ receptor, we constructed anti-murine CD40 antibodies Anti-mCD40-hIgG2-SDIE, Anti-mCD40-hIgG2-GASDALIE and Anti-mCD40-hIgG1 (H2) respectively based on heavy chain constant regions G2-SDIE, G2-GASDALIE and G1 (H2) and compared their immuno-activating activity in the OVA vaccine model. The three antibodies all possessed preferred CH1-hinge regions of human IgG2. Compared to Anti-mCD40-hIgG1 (H2), Anti-mCD40-hIgG2-SDIE and Anti-mCD40-hIgG2-GASDALIE exhibited superior binding capacity for the human inhibitory Fcγ receptor (Table 4), while also superior binding capacity for the human activating Fcγ receptors (Table 4), thus a lower I/A ratio (Table 4). As shown in the OVA vaccine model, Anti-mCD40-hIgG2-SDIE and Anti-mCD40-hIgG2-GASDALIE did not perform better than Anti-mCD40-hIgG1 (H2), and even worse (FIG. 20). This suggests that, a preferred antibody is not only required to have superior binding capacity for the human inhibitory Fcγ receptor but also binding preference for the human inhibitory Fcγ receptor. Such preference can be expressed by an I/A ratio of 0.32 or above.

The examples of preferred antibody heavy chain constant region according to the present invention not only improve activity of agonistic anti-CD40 and anti-DR5 antibodies, but are also applicable on agonistic antibodies for other members in TNF receptor superfamily, such as OX40, CD137, CD27, CD30, GITR, HVEM, TACI, DR4, FAS etc., and agonistic antibodies of specificity (e.g., CD28, SLAM family members) other than TNF receptor superfamily. Included herein are not only agonistic antibodies for regulatory receptors involved in immuno-activation and induction of apoptosis, but also agonistic antibodies for receptor molecules having other biological activities, such as agonistic antibodies for immuno-inhibitory receptor molecules (immune check-points) (e.g., PD-1, CTLA-4, VISTA, TIM-3, BTLA, LAG-3 etc.). Included herein are not only agonistic antibodies based on human IgG antibodies, but also those based on chimeric antibodies comprising sequences of other species. Included herein are not only agonistic antibodies in the classic IgG form comprising two heavy chains and two light chains, but also IgG agonistic antibodies only comprising the heavy chain(s) and other variant forms of IgG derivatives (e.g., antibodies comprising more than two antigen binding sites, bispecific or multispecific antibodies comprising antigen binding site(s) at C-terminal of the heavy chain). Included herein are not only agonistic antibodies based on antibody sequences, but also fusion proteins comprising an antibody constant region sequence and having target activating activity, such as CD40L-Fc fusion protein, OX40L-Fc fusion protein, 4-1BBL-Fc fusion protein, CD27L-Fc fusion protein, CD30L-Fc fusion protein, CD95L-Fc fusion protein, TRAIL-Fc fusion protein, PD-L1-Fc fusion protein etc, more specifically CD40L-JAC1, CD40L-JAC4, OX40L-JAC1, OX40L-JAC4, PD-L1-JAC1, PD-L1-JAC4 etc. (Table 5)

TABLE 5

Examples of fusion proteins based on heavy chain constant regions according to the invention

| Fusion protein | Antigen-binding module | Heavy-chain constant region |
|---|---|---|
| CD40L-JAC1 | CD40L | JAC1 |
| CD40L-JAC4 | CD40L | JAC4 |
| OX40L- JAC1 | OX40L | JAC1 |
| OX40L- JAC4 | OX40L | JAC4 |
| PD-L1-JAC1 | PDL1 | JAC1 |
| PD-L1-JAC4 | PDL1 | JAC4 |
| Anti-CD40 SCFV-JAC1 | Anti-CD40 SCFV | JAC1 |
| Anti-CD40 nanobody-JAC1 | Anti-CD40 nanobody | JAC1 |
| Anti-CD40 SCFV-JAC4 | Anti-CD40 SCFV | JAC4 |
| Anti-CD40 nanobody-JAC4 | Anti-CD40 nanobody | JAC4 |
| Anti-OX40 SCFV-JAC1 | Anti-CD40 SCFV | JAC1 |
| Anti-OX40 nanobody-JAC1 | Anti-CD40 nanobody | JAC1 |
| Anti-OX40 SCFV-JAC4 | Anti-CD40 SCFV | JAC4 |
| Anti-OX40 nanobody-JAC4 | Anti-CD40 nanobody | JAC4 |
| Anti-PD1-SCFV-JAC1 | Anti-PD1 SCFV | JAC1 |
| Anti-PD1 nanobody-JAC1 | Anti-PD1 nanobody | JAC1 |
| Anti-PD1-SCFV-JAC4 | Anti-PD1 SCFV | JAC4 |
| Anti-PD1 nanobody-JAC4 | Anti-PD1 nanobody | JAC4 |

Though specific embodiments having been described for purpose of illustration, it will be appreciated by a person of skills in the art that the various modifications can be made without departing from the spirit and scope of the invention as outlined by the claims.

The invention claimed is:

1. A fusion protein with enhanced agonistic activity, comprising a heavy chain constant region and an antigen binding module at the N-terminal and/or the C-terminal of said heavy chain constant region, the heavy chain constant region as sequentially linked in the direction of N-terminal to C-terminal, a CH1 domain, a hinge region, a CH2 domain and a CH3 domain, wherein, the sequences of said CH1 domain and hinge region are from the sequences of the CH1 domain and hinge region of a human IgG2 and have the wild type function of human IgG2 CH1 domain and hinge region, and the sequences of said CH2 domain and said CH3 domain are a variant sequence of the CH2 domain and the CH3 domain of a human IgG,
wherein said CH2 domain and said CH3 domain have an affinity to human FcγRIIB higher than the affinity of human IgG1 to human FcγRIIB, and said CH2 domain and said CH3 domain has a higher relative binding preference for human FcγRIIB over activating human FcγRs selected from human FcγRI, FcγRIIA, and FcγRIIIA than human IgG1,
wherein said binding preference for human FcγRIIB over activating human FcγRs is defined by the relative binding affinity to human FcγRIIB over activating human FcγRs selected from human FcγRI, FcγRIIA, and FcγRIIIA, and quantified as an I/A ratio calculated by the equation:
I/A ratio=the lower of the fusion protein's equilibrium dissociation constant for the hFcγRIIA-R131 and the fusion protein's equilibrium dissociation constant for the hFcγRIIIA-F158 divided by the fusion protein's equilibrium dissociation constant for the hFcγRIIB, wherein the fusion protein has an I/A ratio between 0.32 and 271,
wherein the sequences of said CH2 domain and said CH3 domain are selected from the group consisting of:
a) the sequences of a CH2 domain and a CH3 domain of a human IgG1 and comprise the amino acid mutations G237D, P238D, P271G and A330R;
b) the sequences of a CH2 domain and a CH3 domain of a human IgG1 and comprise the amino acid mutations G237D, P238D, H268D, P271G and A330R;
c) the sequences of a CH2 domain and a CH3 domain of a human IgG2 and comprise the amino acid mutations S267E and L328F; and
d) the sequences of a CH2 domain and a CH3 domain of a human IgG2 and comprise the amino acid mutations H268D and P271G,
wherein the positions of the amino acid mutations are numbered according to the EU numbering for IgGs.

2. The fusion protein according to claim 1, wherein said antigen binding module is selected from the group consisting of antigen binding fragments of antibodies, adnectins, heavy chain variable regions of alpaca antibodies, miniantibodies, affibodies, affilins, target-binding regions of receptors, cell adhesion molecules, ligands, enzymes, cytokines and chemokines.

3. The fusion protein according to claim 1, wherein said antigen binding module is a heavy chain variable region of an alpaca antibody.

4. The fusion protein according to claim 1, wherein said antigen binding module is a ligand, and wherein said ligand is an immuno-costimulatory molecule selected from the group consisting of CD80, CD86, ICOSL, OX40L, CD137L, CD40L, CD30L, CD27L, CD244, CD150, CD48, CD84, CD319, Ly118 CD229 and SLAMF8.

5. The fusion protein according to claim 1, wherein said antigen binding module targets an antigen selected from the group consisting of CD40, DR5, OX40, CD137, CD27, CD30, GITR, HVEM, TACI, DR4 and FAS.

6. The fusion protein according to claim 1, wherein said antigen binding module targets CD40.

7. The fusion protein according to claim 1, wherein said antigen binding module targets an antigen selected from the group consisting of PD-1, CTLA-4, VISTA, TIM-3, BTLA and LAG-3.

8. The fusion protein according to claim 1, wherein said antigen binding module is an immuno-inhibitory ligand molecule selected from the group consisting of PD-L1, PD-L2, B7-H3, B7-H4, CD47, VISTA, HVEM and GAL9.

9. An antibody with enhanced agonistic activity comprising a heavy chain constant region, wherein the heavy chain constant region as sequentially linked in the direction of N-terminal to C-terminal, a CH1 domain, a hinge region, a CH2 domain and a CH3 domain, wherein, the sequences of said CH1 domain and hinge region are from the sequences of the CH1 domain and hinge region of a human IgG2 and have the wild type function of human IgG2 CH1 domain and hinge region, and wherein the sequences of said CH2 domain and said CH3 domain are a variant sequence of the CH2 domain and the CH3 domain of a human IgG,
wherein said CH2 domain and said CH3 domain have an affinity to human FcγRIIB higher than the affinity of human IgG1 to human FcγRIIB, and said CH2 domain and said CH3 domain has a higher binding preference for human FcγRIIB over activating human FcγRs selected from human FcγRI, FcγRIIA, and FcγRIIIA than human IgG1, wherein said binding preference for human FcγRIIB over activating human FcγRs is defined by the relative binding affinity to human FcγRIIB over activating human FcγRs selected from human FcγRI, FcγRIIA, and FcγRIIIA, and quantified as an I/A ratio calculated by the equation:

I/A ratio=the lower of the antibody's equilibrium dissociation constant for the hFcγRIIA-R131 and the antibody's equilibrium dissociation constant for the hFcγRIIIA-F158 divided by the antibody's equilibrium dissociation constant for the hFcγRIIB, wherein the antibody has an I/A ratio between 0.32 and 271;

wherein the sequences of said CH2 domain and said CH3 domain are selected from the group consisting of:
a) the sequences of a CH2 domain and a CH3 domain of a human IgG1 and comprise the amino acid mutations G237D, P238D, P271G and A330R; or
b) the sequences of a CH2 domain and a CH3 domain of a human IgG1 and comprise the amino acid mutations G237D, P238D, H268D, P271G and A330R; or
c) the sequences of a CH2 domain and a CH3 domain of a human IgG2 and comprise the amino acid mutations S267E and L328F; and
d) the sequences of a CH2 domain and a CH3 domain of a human IgG2 and comprise the amino acid mutations H268D and P271G, wherein the positions of the amino acid mutations are numbered according to the EU numbering for IgGs.

10. The antibody according to claim 9, wherein said antibody targets an antigen selected from the group consisting of CD40 and DR5.

11. The antibody according to claim 9, wherein said antibody targets CD40.

12. The antibody according to claim 11, wherein the light chain of said antibody has the sequence of SEQ ID NO:47, and the heavy chain of said antibody has the sequence of SEQ ID NO:27 or SEQ ID NO:43.

13. A pharmaceutical composition, comprising
a) a therapeutically effective amount of the fusion protein according to any one of claims 1-8; and
b) a pharmaceutically acceptable carrier.

14. A nucleic acid sequence encoding the fusion protein according to any one of claims 1-8.

15. The fusion protein according to claim 1, wherein the heavy chain constant region comprises the sequence of SEQ ID NO:11 or SEQ ID NO:12 or SEQ ID NO:13 or SEQ ID NO:14.

16. The antibody according to claim 9, wherein the heavy chain constant region comprises the sequence of SEQ ID NO:11 or SEQ ID NO:12 or SEQ ID NO:13 or SEQ ID NO:14.

17. The antibody of claim 9, wherein said antibody targets an antigen selected from the group consisting of CD40, DR5, OX40, CD137, CD27, CD30, GITR, HVEM, TACI, DR4 and FAS.

18. The antibody of claim 9, wherein said antibody targets an immuno-inhibitory receptor molecule selected from the group consisting of PD-1, CTLA-4, VISTA, TIM-3, BTLA and LAG-3.

* * * * *

SEQUENCE LISTING

```
<160> NUMBER OF SEQ ID NOS: 54

<210> SEQ ID NO 1
<211> LENGTH: 114
<212> TYPE: PRT
<213> ORGANISM: Homo sapiens

<400> SEQUENCE: 1

Ala Thr Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala

<210> SEQ ID NO 2
<211> LENGTH: 111
<212> TYPE: PRT
<213> ORGANISM: Homo sapiens

<400> SEQUENCE: 2

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80
```

```
Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala
            100                 105                 110
```

<210> SEQ ID NO 3
<211> LENGTH: 161
<212> TYPE: PRT
<213> ORGANISM: Homo sapiens

<400> SEQUENCE: 3

```
Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala
```

<210> SEQ ID NO 4
<211> LENGTH: 111
<212> TYPE: PRT
<213> ORGANISM: Homo sapiens

<400> SEQUENCE: 4

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala
            100                 105                 110
```

<210> SEQ ID NO 5
<211> LENGTH: 216

<212> TYPE: PRT
<213> ORGANISM: Homo sapiens

<400> SEQUENCE: 5

Pro Glu Leu Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Pro Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Ala
                85                  90                  95

Leu Pro Ala Pro Ile Glu Lys Thr Ile Ser Lys Ala Lys Gly Gln Pro
            100                 105                 110

Arg Glu Pro Gln Val Tyr Thr Leu Pro Pro Ser Arg Asp Glu Leu Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210                 215

<210> SEQ ID NO 6
<211> LENGTH: 215
<212> TYPE: PRT
<213> ORGANISM: Homo sapiens

<400> SEQUENCE: 6

Pro Pro Val Ala Gly Pro Ser Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser His Glu Asp Pro Glu Val Gln Phe Asn Trp Tyr Val Asp
        35                  40                  45

Gly Val Glu Val His Asn Ala Lys Thr Lys Pro Arg Glu Glu Gln Phe
    50                  55                  60

Asn Ser Thr Phe Arg Val Val Ser Val Leu Thr Val Val His Gln Asp
65                  70                  75                  80

Trp Leu Asn Gly Lys Glu Tyr Lys Cys Lys Val Ser Asn Lys Gly Leu
                85                  90                  95

Pro Ala Pro Ile Glu Lys Thr Ile Ser Lys Thr Lys Gly Gln Pro Arg
            100                 105                 110

Glu Pro Gln Val Tyr Thr Leu Pro Pro Ser Arg Glu Glu Met Thr Lys
        115                 120                 125

```
Asn Gln Val Ser Leu Thr Cys Leu Val Lys Gly Phe Tyr Pro Ser Asp
    130                 135                 140
Ile Ala Val Glu Trp Glu Ser Asn Gly Gln Pro Glu Asn Asn Tyr Lys
145                 150                 155                 160
Thr Thr Pro Pro Met Leu Asp Ser Asp Gly Ser Phe Phe Leu Tyr Ser
                165                 170                 175
Lys Leu Thr Val Asp Lys Ser Arg Trp Gln Gln Gly Asn Val Phe Ser
            180                 185                 190
Cys Ser Val Met His Glu Ala Leu His Asn His Tyr Thr Gln Lys Ser
        195                 200                 205
Leu Ser Leu Ser Pro Gly Lys
    210                 215
```

<210> SEQ ID NO 7
<211> LENGTH: 216
<212> TYPE: PRT
<213> ORGANISM: Homo sapiens

<400> SEQUENCE: 7

```
Pro Glu Leu Leu Gly Gly Pro Ser Val Phe Leu Phe Pro Pro Lys Pro
1               5                   10                  15
Lys Asp Thr Leu Met Ile Ser Arg Thr Pro Glu Val Thr Cys Val Val
            20                  25                  30
Val Asp Val Ser His Glu Asp Pro Glu Val Gln Phe Lys Trp Tyr Val
        35                  40                  45
Asp Gly Val Glu Val His Asn Ala Lys Thr Lys Pro Arg Glu Glu Gln
    50                  55                  60
Tyr Asn Ser Thr Phe Arg Val Val Ser Val Leu Thr Val Leu His Gln
65                  70                  75                  80
Asp Trp Leu Asn Gly Lys Glu Tyr Lys Cys Lys Val Ser Asn Lys Ala
                85                  90                  95
Leu Pro Ala Pro Ile Glu Lys Thr Ile Ser Lys Thr Lys Gly Gln Pro
            100                 105                 110
Arg Glu Pro Gln Val Tyr Thr Leu Pro Pro Ser Arg Glu Glu Met Thr
        115                 120                 125
Lys Asn Gln Val Ser Leu Thr Cys Leu Val Lys Gly Phe Tyr Pro Ser
    130                 135                 140
Asp Ile Ala Val Glu Trp Glu Ser Ser Gly Gln Pro Glu Asn Asn Tyr
145                 150                 155                 160
Asn Thr Thr Pro Pro Met Leu Asp Ser Asp Gly Ser Phe Phe Leu Tyr
                165                 170                 175
Ser Lys Leu Thr Val Asp Lys Ser Arg Trp Gln Gln Gly Asn Ile Phe
            180                 185                 190
Ser Cys Ser Val Met His Glu Ala Leu His Asn Arg Phe Thr Gln Lys
        195                 200                 205
Ser Leu Ser Leu Ser Pro Gly Lys
    210                 215
```

<210> SEQ ID NO 8
<211> LENGTH: 216
<212> TYPE: PRT
<213> ORGANISM: Homo sapiens

<400> SEQUENCE: 8

```
Pro Glu Phe Leu Gly Gly Pro Ser Val Phe Leu Phe Pro Pro Lys Pro
1               5                   10                  15
```

Lys Asp Thr Leu Met Ile Ser Arg Thr Pro Glu Val Thr Cys Val Val
            20                  25                  30

Val Asp Val Ser Gln Glu Asp Pro Glu Val Gln Phe Asn Trp Tyr Val
                35                  40                  45

Asp Gly Val Glu Val His Asn Ala Lys Thr Lys Pro Arg Glu Glu Gln
    50                  55                  60

Phe Asn Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Gly
                85                  90                  95

Leu Pro Ser Ser Ile Glu Lys Thr Ile Ser Lys Ala Lys Gly Gln Pro
                100                 105                 110

Arg Glu Pro Gln Val Tyr Thr Leu Pro Pro Ser Gln Glu Glu Met Thr
            115                 120                 125

Lys Asn Gln Val Ser Leu Thr Cys Leu Val Lys Gly Phe Tyr Pro Ser
        130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Arg Leu Thr Val Asp Lys Ser Arg Trp Gln Glu Gly Asn Val Phe
            180                 185                 190

Ser Cys Ser Val Met His Glu Ala Leu His Asn His Tyr Thr Gln Lys
        195                 200                 205

Ser Leu Ser Leu Ser Leu Gly Lys
    210                 215

<210> SEQ ID NO 9
<211> LENGTH: 216
<212> TYPE: PRT
<213> ORGANISM: Artificial sequence
<220> FEATURE:
<223> OTHER INFORMATION: amino acid sequence for antibody IgG1 CH2-CH3
      domain variant V11

<400> SEQUENCE: 9

Pro Glu Leu Leu Gly Asp Asp Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser Asp Glu Asp Gly Glu Val Lys Phe Asn Trp Tyr Val
                35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Ala
                85                  90                  95

Leu Pro Arg Pro Ile Glu Lys Thr Ile Ser Lys Ala Lys Gly Gln Pro
                100                 105                 110

Arg Glu Pro Gln Val Tyr Thr Leu Pro Pro Ser Arg Asp Glu Leu Thr
            115                 120                 125

Lys Asn Gln Val Ser Leu Thr Cys Leu Val Lys Gly Phe Tyr Pro Ser
        130                 135                 140

Asp Ile Ala Val Glu Trp Glu Ser Asn Gly Gln Pro Glu Asn Asn Tyr
145                 150                 155                 160

```
Lys Thr Thr Pro Pro Val Leu Asp Ser Asp Gly Ser Phe Phe Leu Tyr
            165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
            195                 200                 205

Ser Leu Ser Leu Ser Pro Gly Lys
            210             215

<210> SEQ ID NO 10
<211> LENGTH: 216
<212> TYPE: PRT
<213> ORGANISM: Artificial sequence
<220> FEATURE:
<223> OTHER INFORMATION: amino acid sequence for IgG1 antibody CH2-CH3
      domain variant V9

<400> SEQUENCE: 10

Pro Glu Leu Leu Gly Asp Asp Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser His Glu Asp Gly Glu Val Lys Phe Asn Trp Tyr Val
        35                  40                  45

Asp Gly Val Glu Val His Asn Ala Lys Thr Lys Pro Arg Glu Glu Gln
    50                  55                  60

Tyr Asn Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Ala
                85                  90                  95

Leu Pro Arg Pro Ile Glu Lys Thr Ile Ser Lys Ala Lys Gly Gln Pro
            100                 105                 110

Arg Glu Pro Gln Val Tyr Thr Leu Pro Pro Ser Arg Asp Glu Leu Thr
        115                 120                 125

Lys Asn Gln Val Ser Leu Thr Cys Leu Val Lys Gly Phe Tyr Pro Ser
    130                 135                 140

Asp Ile Ala Val Glu Trp Glu Ser Asn Gly Gln Pro Glu Asn Asn Tyr
145                 150                 155                 160

Lys Thr Thr Pro Pro Val Leu Asp Ser Asp Gly Ser Phe Phe Leu Tyr
                165                 170                 175

Ser Lys Leu Thr Val Asp Lys Ser Arg Trp Gln Gln Gly Asn Val Phe
            180                 185                 190

Ser Cys Ser Val Met His Glu Ala Leu His Asn His Tyr Thr Gln Lys
        195                 200                 205

Ser Leu Ser Leu Ser Pro Gly Lys
    210             215

<210> SEQ ID NO 11
<211> LENGTH: 327
<212> TYPE: PRT
<213> ORGANISM: Artificial sequence
<220> FEATURE:
<223> OTHER INFORMATION: amino acid sequence of antibody heavy chain
      constant region variant JAC1

<400> SEQUENCE: 11

Ala Ser Thr Lys Gly Pro Ser Val Phe Pro Leu Ala Pro Cys Ser Arg
1               5                   10                  15
```

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Glu Leu Leu Gly Asp Asp Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Asp Glu Asp Gly Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Arg Pro Ile Glu Lys Thr Ile Ser Lys Ala Lys Gly Gln Pro Arg
    210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 12
<211> LENGTH: 327
<212> TYPE: PRT
<213> ORGANISM: Artificial sequence
<220> FEATURE:
<223> OTHER INFORMATION: amino acid sequence of Antibody heavy chain
      constant region variant JAC2

<400> SEQUENCE: 12

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

```
                35                  40                  45
Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Glu Leu Leu Gly Asp Asp Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser His Glu Asp Gly Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
            195                 200                 205

Pro Arg Pro Ile Glu Lys Thr Ile Ser Lys Ala Lys Gly Gln Pro Arg
            210                 215                 220

Glu Pro Gln Val Tyr Thr Leu Pro Pro Ser Arg Asp Glu Leu Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 13
<211> LENGTH: 326
<212> TYPE: PRT
<213> ORGANISM: Artificial sequence
<220> FEATURE:
<223> OTHER INFORMATION: amino acid sequence of Antibody heavy chain
      constant region variant JAC3

<400> SEQUENCE: 13

Ala Ser Thr Lys Gly Pro Ser Val Phe Pro Leu Ala Pro Cys Ser Arg
 1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60
```

```
Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Glu His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
                180                 185                 190

Leu Asn Gly Lys Glu Tyr Lys Cys Lys Val Ser Asn Lys Gly Phe Pro
            195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 14
<211> LENGTH: 326
<212> TYPE: PRT
<213> ORGANISM: Artificial sequence
<220> FEATURE:
<223> OTHER INFORMATION: amino acid sequence of Antibody heavy chain
      constant region variant JAC4

<400> SEQUENCE: 14

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95
```

Thr Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser Asp Glu Asp Gly Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 15
<211> LENGTH: 465
<212> TYPE: PRT
<213> ORGANISM: Artificial sequence
<220> FEATURE:
<223> OTHER INFORMATION: amino acid sequence for the heavy chain of
      Human anti-murine CD40 antibody Anti-mCD40-hIgG1

<400> SEQUENCE: 15

Met Asp Ile Arg Leu Ser Leu Val Phe Leu Val Leu Phe Ile Lys Gly
1               5                   10                  15

Val Gln Cys Glu Val Gln Leu Val Glu Ser Asp Gly Gly Leu Val Gln
            20                  25                  30

Pro Gly Arg Ser Leu Lys Leu Pro Cys Ala Ala Ser Gly Phe Thr Phe
        35                  40                  45

Ser Asp Tyr Tyr Met Ala Trp Val Arg Gln Ala Pro Thr Lys Gly Leu
    50                  55                  60

Glu Trp Val Ala Ser Ile Ser Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Gly Arg His Ser Ser Tyr Phe Asp Tyr Trp Gly Gln Gly

```
            115                 120                 125
Val Met Val Thr Val Ser Ser Ala Thr Thr Lys Gly Pro Ser Val Phe
        130                 135                 140
Pro Leu Ala Pro Ser Ser Lys Ser Thr Ser Gly Gly Thr Ala Ala Leu
145                 150                 155                 160
Gly Cys Leu Val Lys Asp Tyr Phe Pro Glu Pro Val Thr Val Ser Trp
                165                 170                 175
Asn Ser Gly Ala Leu Thr Ser Gly Val His Thr Phe Pro Ala Val Leu
            180                 185                 190
Gln Ser Ser Gly Leu Tyr Ser Leu Ser Ser Val Val Thr Val Pro Ser
        195                 200                 205
Ser Ser Leu Gly Thr Gln Thr Tyr Ile Cys Asn Val Asn His Lys Pro
    210                 215                 220
Ser Asn Thr Lys Val Asp Lys Arg Val Glu Pro Lys Ser Cys Asp Lys
225                 230                 235                 240
Thr His Thr Cys Pro Pro Cys Pro Ala Pro Glu Leu Leu Gly Gly Pro
                245                 250                 255
Ser Val Phe Leu Phe Pro Pro Lys Pro Lys Asp Thr Leu Met Ile Ser
            260                 265                 270
Arg Thr Pro Glu Val Thr Cys Val Val Val Asp Val Ser His Glu Asp
        275                 280                 285
Pro Glu Val Lys Phe Asn Trp Tyr Val Asp Gly Val Glu Val His Asn
    290                 295                 300
Ala Lys Thr Lys Pro Arg Glu Glu Gln Tyr Asn Ser Thr Tyr Arg Val
305                 310                 315                 320
Val Ser Val Leu Thr Val Leu His Gln Asp Trp Leu Asn Gly Lys Glu
                325                 330                 335
Tyr Lys Cys Lys Val Ser Asn Lys Ala Leu Pro Ala Pro Ile Glu Lys
            340                 345                 350
Thr Ile Ser Lys Ala Lys Gly Gln Pro Arg Glu Pro Gln Val Tyr Thr
        355                 360                 365
Leu Pro Pro Ser Arg Asp Glu Leu Thr Lys Asn Gln Val Ser Leu Thr
    370                 375                 380
Cys Leu Val Lys Gly Phe Tyr Pro Ser Asp Ile Ala Val Glu Trp Glu
385                 390                 395                 400
Ser Asn Gly Gln Pro Glu Asn Asn Tyr Lys Thr Thr Pro Pro Val Leu
                405                 410                 415
Asp Ser Asp Gly Ser Phe Phe Leu Tyr Ser Lys Leu Thr Val Asp Lys
            420                 425                 430
Ser Arg Trp Gln Gln Gly Asn Val Phe Ser Cys Ser Val Met His Glu
        435                 440                 445
Ala Leu His Asn His Tyr Thr Gln Lys Ser Leu Ser Leu Ser Pro Gly
    450                 455                 460
Lys
465

<210> SEQ ID NO 16
<211> LENGTH: 475
<212> TYPE: PRT
<213> ORGANISM: Artificial sequence
<220> FEATURE:
<223> OTHER INFORMATION: amino acid sequence for the heavy chain of
      Human anti-human CD40 antibody Anti-hCD40-hIgG1

<400> SEQUENCE: 16
```

```
Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
            35                  40                  45

Thr Gly Tyr Tyr Met His Trp Val Arg Gln Ala Pro Gly Gln Gly Leu
    50                  55                  60

Glu Trp Met Gly Trp Ile Asn Pro Asp Ser Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
            115                 120                 125

Cys Ser Tyr Phe Asp Tyr Trp Gly Gln Gly Thr Leu Val Thr Val Ser
    130                 135                 140

Ser Ala Thr Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
    195                 200                 205

Ser Leu Ser Ser Val Val Thr Val Pro Ser Ser Ser Leu Gly Thr Gln
210                 215                 220

Thr Tyr Ile Cys Asn Val Asn His Lys Pro Ser Asn Thr Lys Val Asp
225                 230                 235                 240

Lys Arg Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
            260                 265                 270

Pro Lys Pro Lys Asp Thr Leu Met Ile Ser Arg Thr Pro Glu Val Thr
    275                 280                 285

Cys Val Val Val Asp Val Ser His Glu Asp Pro Glu Val Lys Phe Asn
290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
    355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
```

```
                420             425             430
Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 17
<211> LENGTH: 461
<212> TYPE: PRT
<213> ORGANISM: Artificial sequence
<220> FEATURE:
<223> OTHER INFORMATION: amino acid sequence for the heavy chain of
      Human anti-murine CD40 antibody Anti-mCD40-hIgG2

<400> SEQUENCE: 17

Met Asp Ile Arg Leu Ser Leu Val Phe Leu Val Leu Phe Ile Lys Gly
1               5                   10                  15

Val Gln Cys Glu Val Gln Leu Val Glu Ser Asp Gly Gly Leu Val Gln
                20                  25                  30

Pro Gly Arg Ser Leu Lys Leu Pro Cys Ala Ala Ser Gly Phe Thr Phe
            35                  40                  45

Ser Asp Tyr Tyr Met Ala Trp Val Arg Gln Ala Pro Thr Lys Gly Leu
    50                  55                  60

Glu Trp Val Ala Ser Ile Ser Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Gly Arg His Ser Ser Tyr Phe Asp Tyr Trp Gly Gln Gly
        115                 120                 125

Val Met Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Pro Val Ala Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Gln
        275                 280                 285

Phe Asn Trp Tyr Val Asp Gly Val Glu Val His Asn Ala Lys Thr Lys
    290                 295                 300
```

```
Pro Arg Glu Glu Gln Phe Asn Ser Thr Phe Arg Val Val Ser Val Leu
305                 310                 315                 320

Thr Val Val His Gln Asp Trp Leu Asn Gly Lys Glu Tyr Lys Cys Lys
            325                 330                 335

Val Ser Asn Lys Gly Leu Pro Ala Pro Ile Glu Lys Thr Ile Ser Lys
        340                 345                 350

Thr Lys Gly Gln Pro Arg Glu Pro Gln Val Tyr Thr Leu Pro Pro Ser
    355                 360                 365

Arg Glu Glu Met Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Met Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 18
<211> LENGTH: 471
<212> TYPE: PRT
<213> ORGANISM: Artificial sequence
<220> FEATURE:
<223> OTHER INFORMATION: amino acid sequence for the heavy chain of
      Human anti-human CD40 antibody Anti-hCD40-hIgG2

<400> SEQUENCE: 18

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Asp Ser Gly Gly Thr Asn Tyr Ala
65                  70                  75                  80

Gln Lys Phe Gln Gly Arg Val Thr Met Thr Arg Asp Thr Ser Ile Ser
            85                  90                  95

Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
        115                 120                 125

Cys Ser Tyr Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
            165                 170                 175

Tyr Phe Pro Glu Pro Val Thr Val Ser Trp Asn Ser Gly Ala Leu Thr
        180                 185                 190

Ser Gly Val His Thr Phe Pro Ala Val Leu Gln Ser Ser Gly Leu Tyr
    195                 200                 205
```

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
                260                 265                 270

Asp Thr Leu Met Ile Ser Arg Thr Pro Glu Val Thr Cys Val Val Val
        275                 280                 285

Asp Val Ser His Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Asn Ser Thr Phe Arg Val Val Ser Val Leu Thr Val Val His Gln Asp
                325                 330                 335

Trp Leu Asn Gly Lys Glu Tyr Lys Cys Lys Val Ser Asn Lys Gly Leu
            340                 345                 350

Pro Ala Pro Ile Glu Lys Thr Ile Ser Lys Thr Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Met Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 19
<211> LENGTH: 512
<212> TYPE: PRT
<213> ORGANISM: Artificial sequence
<220> FEATURE:
<223> OTHER INFORMATION: amino acid sequence for the heavy chain of
      Human anti-murine CD40 antibody Anti-mCD40-hIgG3

<400> SEQUENCE: 19

Met Asp Ile Arg Leu Ser Leu Val Phe Leu Val Leu Phe Ile Lys Gly
1               5                   10                  15

Val Gln Cys Glu Val Gln Leu Val Glu Ser Asp Gly Gly Leu Val Gln
                20                  25                  30

Pro Gly Arg Ser Leu Lys Leu Pro Cys Ala Ala Ser Gly Phe Thr Phe
            35                  40                  45

Ser Asp Tyr Tyr Met Ala Trp Val Arg Gln Ala Pro Thr Lys Gly Leu
        50                  55                  60

Glu Trp Val Ala Ser Ile Ser Tyr Asp Gly Ser Ser Thr Tyr Tyr Arg
65                  70                  75                  80

Asp Ser Val Lys Gly Arg Phe Thr Ile Ser Arg Asp Asn Ala Lys Ser

```
                 85                  90                  95
Thr Leu Tyr Leu Gln Met Asp Ser Leu Arg Ser Glu Asp Thr Ala Thr
            100                 105                 110
Tyr Tyr Cys Gly Arg His Ser Ser Tyr Phe Asp Tyr Trp Gly Gln Gly
            115                 120                 125
Val Met Val Thr Val Ser Ser Ala Ser Thr Lys Gly Pro Ser Val Phe
130                 135                 140
Pro Leu Ala Pro Cys Ser Arg Ser Thr Ser Gly Gly Thr Ala Ala Leu
145                 150                 155                 160
Gly Cys Leu Val Lys Asp Tyr Phe Pro Glu Pro Val Thr Val Ser Trp
                165                 170                 175
Asn Ser Gly Ala Leu Thr Ser Gly Val His Thr Phe Pro Ala Val Leu
            180                 185                 190
Gln Ser Ser Gly Leu Tyr Ser Leu Ser Ser Val Val Thr Val Pro Ser
            195                 200                 205
Ser Ser Leu Gly Thr Gln Thr Tyr Thr Cys Asn Val Asn His Lys Pro
210                 215                 220
Ser Asn Thr Lys Val Asp Lys Arg Val Glu Leu Lys Thr Pro Leu Gly
225                 230                 235                 240
Asp Thr Thr His Thr Cys Pro Arg Cys Pro Glu Pro Lys Ser Cys Asp
                245                 250                 255
Thr Pro Pro Pro Cys Pro Arg Cys Pro Glu Pro Lys Ser Cys Asp Thr
            260                 265                 270
Pro Pro Pro Cys Pro Arg Cys Pro Glu Pro Lys Ser Cys Asp Thr Pro
            275                 280                 285
Pro Pro Cys Pro Arg Cys Pro Ala Pro Glu Leu Leu Gly Gly Pro Ser
290                 295                 300
Val Phe Leu Phe Pro Pro Lys Pro Lys Asp Thr Leu Met Ile Ser Arg
305                 310                 315                 320
Thr Pro Glu Val Thr Cys Val Val Val Asp Val Ser His Glu Asp Pro
                325                 330                 335
Glu Val Gln Phe Lys Trp Tyr Val Asp Gly Val Glu Val His Asn Ala
            340                 345                 350
Lys Thr Lys Pro Arg Glu Glu Gln Tyr Asn Ser Thr Phe Arg Val Val
            355                 360                 365
Ser Val Leu Thr Val Leu His Gln Asp Trp Leu Asn Gly Lys Glu Tyr
370                 375                 380
Lys Cys Lys Val Ser Asn Lys Ala Leu Pro Ala Pro Ile Glu Lys Thr
385                 390                 395                 400
Ile Ser Lys Thr Lys Gly Gln Pro Arg Glu Pro Gln Val Tyr Thr Leu
                405                 410                 415
Pro Pro Ser Arg Glu Glu Met Thr Lys Asn Gln Val Ser Leu Thr Cys
            420                 425                 430
Leu Val Lys Gly Phe Tyr Pro Ser Asp Ile Ala Val Glu Trp Glu Ser
            435                 440                 445
Ser Gly Gln Pro Glu Asn Asn Tyr Asn Thr Thr Pro Pro Met Leu Asp
450                 455                 460
Ser Asp Gly Ser Phe Phe Leu Tyr Ser Lys Leu Thr Val Asp Lys Ser
465                 470                 475                 480
Arg Trp Gln Gln Gly Asn Ile Phe Ser Cys Ser Val Met His Glu Ala
                485                 490                 495
Leu His Asn Arg Phe Thr Gln Lys Ser Leu Ser Leu Ser Pro Gly Lys
            500                 505                 510
```

<210> SEQ ID NO 20
<211> LENGTH: 522
<212> TYPE: PRT
<213> ORGANISM: Artificial sequence
<220> FEATURE:
<223> OTHER INFORMATION: amino acid sequence for the heavy chain of
    Human anti-human CD40 antibody Anti-hCD40-hIgG3

<400> SEQUENCE: 20

```
Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Asp Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
        115                 120                 125

Cys Ser Tyr Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Thr Cys Asn Val Asn His Lys Pro Ser Asn Thr Lys Val Asp
225                 230                 235                 240

Lys Arg Val Glu Leu Lys Thr Pro Leu Gly Asp Thr Thr His Thr Cys
                245                 250                 255

Pro Arg Cys Pro Glu Pro Lys Ser Cys Asp Thr Pro Pro Pro Cys Pro
            260                 265                 270

Arg Cys Pro Glu Pro Lys Ser Cys Asp Thr Pro Pro Pro Cys Pro Arg
        275                 280                 285

Cys Pro Glu Pro Lys Ser Cys Asp Thr Pro Pro Pro Cys Pro Arg Cys
    290                 295                 300

Pro Ala Pro Glu Leu Leu Gly Gly Pro Ser Val Phe Leu Phe Pro Pro
305                 310                 315                 320

Lys Pro Lys Asp Thr Leu Met Ile Ser Arg Thr Pro Glu Val Thr Cys
                325                 330                 335

Val Val Val Asp Val Ser His Glu Asp Pro Glu Val Gln Phe Lys Trp
            340                 345                 350

Tyr Val Asp Gly Val Glu Val His Asn Ala Lys Thr Lys Pro Arg Glu
```

```
                355                 360                 365
Glu Gln Tyr Asn Ser Thr Phe Arg Val Val Ser Val Leu Thr Val Leu
370                 375                 380

His Gln Asp Trp Leu Asn Gly Lys Glu Tyr Lys Cys Lys Val Ser Asn
385                 390                 395                 400

Lys Ala Leu Pro Ala Pro Ile Glu Lys Thr Ile Ser Lys Thr Lys Gly
                405                 410                 415

Gln Pro Arg Glu Pro Gln Val Tyr Thr Leu Pro Pro Ser Arg Glu Glu
                420                 425                 430

Met Thr Lys Asn Gln Val Ser Leu Thr Cys Leu Val Lys Gly Phe Tyr
                435                 440                 445

Pro Ser Asp Ile Ala Val Glu Trp Glu Ser Ser Gly Gln Pro Glu Asn
                450                 455                 460

Asn Tyr Asn Thr Thr Pro Pro Met Leu Asp Ser Asp Gly Ser Phe Phe
465                 470                 475                 480

Leu Tyr Ser Lys Leu Thr Val Asp Lys Ser Arg Trp Gln Gln Gly Asn
                485                 490                 495

Ile Phe Ser Cys Ser Val Met His Glu Ala Leu His Asn Arg Phe Thr
                500                 505                 510

Gln Lys Ser Leu Ser Leu Ser Pro Gly Lys
                515                 520

<210> SEQ ID NO 21
<211> LENGTH: 462
<212> TYPE: PRT
<213> ORGANISM: Homo sapiens
<220> FEATURE:
<223> OTHER INFORMATION: amino acid sequence for the heavy chain of
      Human anti-murine CD40 antibody Anti-mCD40-hIgG4

<400> SEQUENCE: 21

Met Asp Ile Arg Leu Ser Leu Val Phe Leu Val Leu Phe Ile Lys Gly
1               5                   10                  15

Val Gln Cys Glu Val Gln Leu Val Glu Ser Asp Gly Gly Leu Val Gln
                20                  25                  30

Pro Gly Arg Ser Leu Lys Leu Pro Cys Ala Ala Ser Gly Phe Thr Phe
            35                  40                  45

Ser Asp Tyr Tyr Met Ala Trp Val Arg Gln Ala Pro Thr Lys Gly Leu
        50                  55                  60

Glu Trp Val Ala Ser Ile Ser Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Gly Arg His Ser Ser Tyr Phe Asp Tyr Trp Gly Gln Gly
        115                 120                 125

Val Met Val Thr Val Ser Ser Ala Ser Thr Lys Gly Pro Ser Val Phe
            130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190
```

Gln Ser Ser Gly Leu Tyr Ser Leu Ser Ser Val Val Thr Val Pro Ser
            195                 200                 205

Ser Ser Leu Gly Thr Lys Thr Tyr Thr Cys Asn Val Asp His Lys Pro
    210                 215                 220

Ser Asn Thr Lys Val Asp Lys Arg Val Glu Ser Lys Tyr Gly Pro Pro
225                 230                 235                 240

Cys Pro Ser Cys Pro Ala Pro Glu Phe Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Gly Leu Pro Ser Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Gln Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Glu Gly Asn Val Phe Ser Cys Ser Val Met His Glu Ala Leu His
        435                 440                 445

Asn His Tyr Thr Gln Lys Ser Leu Ser Leu Ser Leu Gly Lys
    450                 455                 460

<210> SEQ ID NO 22
<211> LENGTH: 472
<212> TYPE: PRT
<213> ORGANISM: Artificial sequence
<220> FEATURE:
<223> OTHER INFORMATION: amino acid sequence for the heavy chain of
      Human anti-human CD40 antibody Anti-hCD40-hIgG4

<400> SEQUENCE: 22

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Asp Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

```
Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
        115                 120                 125

Cys Ser Tyr Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
                180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Lys
            210                 215                 220

Thr Tyr Thr Cys Asn Val Asp His Lys Pro Ser Asn Thr Lys Val Asp
225                 230                 235                 240

Lys Arg Val Glu Ser Lys Tyr Gly Pro Pro Cys Pro Ser Cys Pro Ala
                245                 250                 255

Pro Glu Phe Leu Gly Gly Pro Ser Val Phe Leu Phe Pro Pro Lys Pro
                260                 265                 270

Lys Asp Thr Leu Met Ile Ser Arg Thr Pro Glu Val Thr Cys Val Val
            275                 280                 285

Val Asp Val Ser Gln Glu Asp Pro Glu Val Gln Phe Asn Trp Tyr Val
            290                 295                 300

Asp Gly Val Glu Val His Asn Ala Lys Thr Lys Pro Arg Glu Glu Gln
305                 310                 315                 320

Phe Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Gly
                340                 345                 350

Leu Pro Ser Ser Ile Glu Lys Thr Ile Ser Lys Ala Lys Gly Gln Pro
            355                 360                 365

Arg Glu Pro Gln Val Tyr Thr Leu Pro Pro Ser Gln Glu Glu Met Thr
            370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Arg Leu Thr Val Asp Lys Ser Arg Trp Gln Glu Gly Asn Val Phe
            435                 440                 445

Ser Cys Ser Val Met His Glu Ala Leu His Asn His Tyr Thr Gln Lys
            450                 455                 460

Ser Leu Ser Leu Ser Leu Gly Lys
465                 470

<210> SEQ ID NO 23
<211> LENGTH: 475
<212> TYPE: PRT
<213> ORGANISM: Artificial sequence
<220> FEATURE:
```

<223> OTHER INFORMATION: amino acid sequence for the heavy chain of Human anti-human CD40 antibody Anti-hCD40-hIgG1(V9)

<400> SEQUENCE: 23

```
Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
            35                  40                  45

Thr Gly Tyr Tyr Met His Trp Val Arg Gln Ala Pro Gly Gln Gly Leu
        50                  55                  60

Glu Trp Met Gly Trp Ile Asn Pro Asp Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
            115                 120                 125

Cys Ser Tyr Phe Asp Tyr Trp Gly Gln Gly Thr Leu Val Thr Val Ser
        130                 135                 140

Ser Ala Thr Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Gln
        210                 215                 220

Thr Tyr Ile Cys Asn Val Asn His Lys Pro Ser Asn Thr Lys Val Asp
225                 230                 235                 240

Lys Arg Val Glu Pro Lys Ser Cys Asp Lys Thr His Thr Cys Pro Pro
                245                 250                 255

Cys Pro Ala Pro Glu Leu Leu Gly Asp Asp Ser Val Phe Leu Phe Pro
            260                 265                 270

Pro Lys Pro Lys Asp Thr Leu Met Ile Ser Arg Thr Pro Glu Val Thr
            275                 280                 285

Cys Val Val Val Asp Val Ser His Glu Asp Gly Glu Val Lys Phe Asn
        290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Arg Pro Ile Glu Lys Thr Ile Ser Lys Ala Lys
            355                 360                 365

Gly Gln Pro Arg Glu Pro Gln Val Tyr Thr Leu Pro Pro Ser Arg Asp
        370                 375                 380

Glu Leu Thr Lys Asn Gln Val Ser Leu Thr Cys Leu Val Lys Gly Phe
385                 390                 395                 400
```

```
Tyr Pro Ser Asp Ile Ala Val Glu Trp Glu Ser Asn Gly Gln Pro Glu
            405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
            435                 440                 445

Asn Val Phe Ser Cys Ser Val Met His Glu Ala Leu His Asn His Tyr
            450                 455                 460

Thr Gln Lys Ser Leu Ser Leu Ser Pro Gly Lys
465                 470                 475

<210> SEQ ID NO 24
<211> LENGTH: 465
<212> TYPE: PRT
<213> ORGANISM: Artificial sequence
<220> FEATURE:
<223> OTHER INFORMATION: amino acid sequence for the heavy chain of
      Human anti-murine CD40 antibody Anti-mCD40-hIgG1(V11)

<400> SEQUENCE: 24

Met Asp Ile Arg Leu Ser Leu Val Phe Leu Val Leu Phe Ile Lys Gly
1               5                   10                  15

Val Gln Cys Glu Val Gln Leu Val Glu Ser Asp Gly Gly Leu Val Gln
            20                  25                  30

Pro Gly Arg Ser Leu Lys Leu Pro Cys Ala Ala Ser Gly Phe Thr Phe
            35                  40                  45

Ser Asp Tyr Tyr Met Ala Trp Val Arg Gln Ala Pro Thr Lys Gly Leu
50                  55                  60

Glu Trp Val Ala Ser Ile Ser Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
            85                  90                  95

Thr Leu Tyr Leu Gln Met Asp Ser Leu Arg Ser Glu Asp Thr Ala Thr
            100                 105                 110

Tyr Tyr Cys Gly Arg His Ser Ser Tyr Phe Asp Tyr Trp Gly Gln Gly
            115                 120                 125

Val Met Val Thr Val Ser Ser Ala Thr Thr Lys Gly Pro Ser Val Phe
            130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
            195                 200                 205

Ser Ser Leu Gly Thr Gln Thr Tyr Ile Cys Asn Val Asn His Lys Pro
            210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Asp Asp
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser Asp Glu Asp
```

```
                275                 280                 285
Gly Glu Val Lys Phe Asn Trp Tyr Val Asp Gly Val Glu Val His Asn
290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Arg Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
450                 455                 460

Lys
465

<210> SEQ ID NO 25
<211> LENGTH: 475
<212> TYPE: PRT
<213> ORGANISM: Artificial sequence
<220> FEATURE:
<223> OTHER INFORMATION: amino acid sequence for the heavy chain of
      Human anti-human CD40 antibody Anti-hCD40-hIgG1(V11)

<400> SEQUENCE: 25

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Asp Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
        115                 120                 125

Cys Ser Tyr Phe Asp Tyr Trp Gly Gln Gly Thr Leu Val Thr Val Ser
    130                 135                 140

Ser Ala Thr Thr Lys Gly Pro Ser Val Phe Pro Leu Ala Pro Ser Ser
145                 150                 155                 160
```

```
Lys Ser Thr Ser Gly Gly Thr Ala Ala Leu Gly Cys Leu Val Lys Asp
            165                 170                 175

Tyr Phe Pro Glu Pro Val Thr Val Ser Trp Asn Ser Gly Ala Leu Thr
        180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Arg Val Glu Pro Lys Ser Cys Asp Lys Thr His Thr Cys Pro Pro
                245                 250                 255

Cys Pro Ala Pro Glu Leu Leu Gly Asp Asp Ser Val Phe Leu Phe Pro
            260                 265                 270

Pro Lys Pro Lys Asp Thr Leu Met Ile Ser Arg Thr Pro Glu Val Thr
        275                 280                 285

Cys Val Val Val Asp Val Ser Asp Glu Asp Gly Glu Val Lys Phe Asn
        290                 295                 300

Trp Tyr Val Asp Gly Val Glu Val His Asn Ala Lys Thr Lys Pro Arg
305                 310                 315                 320

Glu Glu Gln Tyr Asn Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Arg Pro Ile Glu Lys Thr Ile Ser Lys Ala Lys
        355                 360                 365

Gly Gln Pro Arg Glu Pro Gln Val Tyr Thr Leu Pro Pro Ser Arg Asp
    370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
        435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 26
<211> LENGTH: 462
<212> TYPE: PRT
<213> ORGANISM: Artificial sequence
<220> FEATURE:
<223> OTHER INFORMATION: amino acid sequence for the heavy chain of
      Human anti-murine CD40 antibody Anti-mCD40-hIgG2(V11)

<400> SEQUENCE: 26

Met Asp Ile Arg Leu Ser Leu Val Phe Leu Val Leu Phe Ile Lys Gly
1               5                   10                  15

Val Gln Cys Glu Val Gln Leu Val Glu Ser Asp Gly Gly Leu Val Gln
            20                  25                  30

Pro Gly Arg Ser Leu Lys Leu Pro Cys Ala Ala Ser Gly Phe Thr Phe
        35                  40                  45
```

```
Ser Asp Tyr Tyr Met Ala Trp Val Arg Gln Ala Pro Thr Lys Gly Leu
 50                  55                  60

Glu Trp Val Ala Ser Ile Ser Tyr Asp Gly Ser Ser Thr Tyr Tyr Arg
 65                  70                  75                  80

Asp Ser Val Lys Gly Arg Phe Thr Ile Ser Arg Asp Asn Ala Lys Ser
                 85                  90                  95

Thr Leu Tyr Leu Gln Met Asp Ser Leu Arg Ser Glu Asp Thr Ala Thr
                100                 105                 110

Tyr Tyr Cys Gly Arg His Ser Ser Tyr Phe Asp Tyr Trp Gly Gln Gly
            115                 120                 125

Val Met Val Thr Val Ser Ser Ala Ser Thr Lys Gly Pro Ser Val Phe
        130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
                180                 185                 190

Gln Ser Ser Gly Leu Tyr Ser Leu Ser Ser Val Val Thr Val Pro Ser
            195                 200                 205

Ser Asn Phe Gly Thr Gln Thr Tyr Thr Cys Asn Val Asp His Lys Pro
        210                 215                 220

Ser Asn Thr Lys Val Asp Lys Thr Val Glu Arg Lys Cys Cys Val Glu
225                 230                 235                 240

Cys Pro Pro Cys Pro Ala Pro Glu Leu Leu Gly Asp Asp Ser Val Phe
                245                 250                 255

Leu Phe Pro Pro Lys Pro Lys Asp Thr Leu Met Ile Ser Arg Thr Pro
                260                 265                 270

Glu Val Thr Cys Val Val Val Asp Val Ser Asp Glu Asp Gly Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Arg Pro Ile Glu Lys Thr Ile Ser
                340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
        370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
                420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
        450                 455                 460
```

```
<210> SEQ ID NO 27
<211> LENGTH: 472
<212> TYPE: PRT
<213> ORGANISM: Artificial sequence
<220> FEATURE:
<223> OTHER INFORMATION: amino acid sequence for the heavy chain of
      Human anti-human CD40 antibody Anti-hCD40-hIgG2(V11)

<400> SEQUENCE: 27
```

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Gly Tyr Tyr Met His Trp Val Arg Gln Ala Pro Gly Gln Gly Leu
        50                  55                  60

Glu Trp Met Gly Trp Ile Asn Pro Asp Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
        115                 120                 125

Cys Ser Tyr Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Glu Leu Leu Gly Asp Asp Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser Asp Glu Asp Gly Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Arg Pro Ile Glu Lys Thr Ile Ser Lys Ala Lys Gly Gln Pro
        355                 360                 365

```
Arg Glu Pro Gln Val Tyr Thr Leu Pro Pro Ser Arg Asp Glu Leu Thr
        370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
                420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
        450                 455                 460

Ser Leu Ser Leu Ser Pro Gly Lys
465                 470

<210> SEQ ID NO 28
<211> LENGTH: 512
<212> TYPE: PRT
<213> ORGANISM: Artificial sequence
<220> FEATURE:
<223> OTHER INFORMATION: amino acid sequence for the heavy chain of
      Human anti-murine CD40 antibody Anti-mCD40-hIgG3(V11)

<400> SEQUENCE: 28

Met Asp Ile Arg Leu Ser Leu Val Phe Leu Val Leu Phe Ile Lys Gly
1               5                   10                  15

Val Gln Cys Glu Val Gln Leu Val Glu Ser Asp Gly Gly Leu Val Gln
            20                  25                  30

Pro Gly Arg Ser Leu Lys Leu Pro Cys Ala Ala Ser Gly Phe Thr Phe
        35                  40                  45

Ser Asp Tyr Tyr Met Ala Trp Val Arg Gln Ala Pro Thr Lys Gly Leu
    50                  55                  60

Glu Trp Val Ala Ser Ile Ser Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Gly Arg His Ser Ser Tyr Phe Asp Tyr Trp Gly Gln Gly
        115                 120                 125

Val Met Val Thr Val Ser Ser Ala Ser Thr Lys Gly Pro Ser Val Phe
130                 135                 140

Pro Leu Ala Pro Cys Ser Arg Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Thr Cys Asn Val Asn His Lys Pro
    210                 215                 220

Ser Asn Thr Lys Val Asp Lys Arg Val Glu Leu Lys Thr Pro Leu Gly
225                 230                 235                 240

Asp Thr Thr His Thr Cys Pro Arg Cys Pro Glu Pro Lys Ser Cys Asp
```

```
                245                 250                 255
Thr Pro Pro Pro Cys Pro Arg Cys Pro Glu Pro Lys Ser Cys Asp Thr
            260                 265                 270

Pro Pro Pro Cys Pro Arg Cys Pro Glu Pro Lys Ser Cys Asp Thr Pro
            275                 280                 285

Pro Pro Cys Pro Arg Cys Pro Ala Pro Glu Leu Leu Gly Asp Asp Ser
        290                 295                 300

Val Phe Leu Phe Pro Pro Lys Pro Lys Asp Thr Leu Met Ile Ser Arg
305                 310                 315                 320

Thr Pro Glu Val Thr Cys Val Val Val Asp Val Ser Asp Glu Asp Gly
                325                 330                 335

Glu Val Lys Phe Asn Trp Tyr Val Asp Gly Val Glu Val His Asn Ala
                340                 345                 350

Lys Thr Lys Pro Arg Glu Glu Gln Tyr Asn Ser Thr Tyr Arg Val Val
                355                 360                 365

Ser Val Leu Thr Val Leu His Gln Asp Trp Leu Asn Gly Lys Glu Tyr
        370                 375                 380

Lys Cys Lys Val Ser Asn Lys Ala Leu Pro Arg Pro Ile Glu Lys Thr
385                 390                 395                 400

Ile Ser Lys Ala Lys Gly Gln Pro Arg Glu Pro Gln Val Tyr Thr Leu
                405                 410                 415

Pro Pro Ser Arg Asp Glu Leu Thr Lys Asn Gln Val Ser Leu Thr Cys
            420                 425                 430

Leu Val Lys Gly Phe Tyr Pro Ser Asp Ile Ala Val Glu Trp Glu Ser
        435                 440                 445

Asn Gly Gln Pro Glu Asn Asn Tyr Lys Thr Thr Pro Pro Val Leu Asp
    450                 455                 460

Ser Asp Gly Ser Phe Phe Leu Tyr Ser Lys Leu Thr Val Asp Lys Ser
465                 470                 475                 480

Arg Trp Gln Gln Gly Asn Val Phe Ser Cys Ser Val Met His Glu Ala
                485                 490                 495

Leu His Asn His Tyr Thr Gln Lys Ser Leu Ser Leu Ser Pro Gly Lys
                500                 505                 510

<210> SEQ ID NO 29
<211> LENGTH: 522
<212> TYPE: PRT
<213> ORGANISM: Artificial sequence
<220> FEATURE:
<223> OTHER INFORMATION: amino acid sequence for the heavy chain of
      Human anti-human CD40 antibody Anti-hCD40-hIgG3(V11)

<400> SEQUENCE: 29

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Gly Tyr Tyr Met His Trp Val Arg Gln Ala Pro Gly Gln Gly Leu
        50                  55                  60

Glu Trp Met Gly Trp Ile Asn Pro Asp Ser Gly Gly Thr Asn Tyr Ala
65              70                  75                  80

Gln Lys Phe Gln Gly Arg Val Thr Met Thr Arg Asp Thr Ser Ile Ser
                85                  90                  95
```

```
Thr Ala Tyr Met Glu Leu Asn Arg Leu Arg Ser Asp Asp Thr Ala Val
            100                 105                 110
Tyr Tyr Cys Ala Arg Asp Gln Pro Leu Gly Tyr Cys Thr Asn Gly Val
        115                 120                 125
Cys Ser Tyr Phe Asp Tyr Trp Gly Gln Gly Thr Leu Val Thr Val Ser
    130                 135                 140
Ser Ala Ser Thr Lys Gly Pro Ser Val Phe Pro Leu Ala Pro Cys Ser
145                 150                 155                 160
Arg Ser Thr Ser Gly Gly Thr Ala Ala Leu Gly Cys Leu Val Lys Asp
                165                 170                 175
Tyr Phe Pro Glu Pro Val Thr Val Ser Trp Asn Ser Gly Ala Leu Thr
                180                 185                 190
Ser Gly Val His Thr Phe Pro Ala Val Leu Gln Ser Ser Gly Leu Tyr
            195                 200                 205
Ser Leu Ser Ser Val Val Thr Val Pro Ser Ser Ser Leu Gly Thr Gln
        210                 215                 220
Thr Tyr Thr Cys Asn Val Asn His Lys Pro Ser Asn Thr Lys Val Asp
225                 230                 235                 240
Lys Arg Val Glu Leu Lys Thr Pro Leu Gly Asp Thr Thr His Thr Cys
                245                 250                 255
Pro Arg Cys Pro Glu Pro Lys Ser Cys Asp Thr Pro Pro Pro Cys Pro
                260                 265                 270
Arg Cys Pro Glu Pro Lys Ser Cys Asp Thr Pro Pro Pro Cys Pro Arg
            275                 280                 285
Cys Pro Glu Pro Lys Ser Cys Asp Thr Pro Pro Pro Cys Pro Arg Cys
        290                 295                 300
Pro Ala Pro Glu Leu Leu Gly Asp Ser Val Phe Leu Phe Pro Pro
305                 310                 315                 320
Lys Pro Lys Asp Thr Leu Met Ile Ser Arg Thr Pro Glu Val Thr Cys
                325                 330                 335
Val Val Val Asp Val Ser Asp Glu Asp Gly Glu Val Lys Phe Asn Trp
            340                 345                 350
Tyr Val Asp Gly Val Glu Val His Asn Ala Lys Thr Lys Pro Arg Glu
        355                 360                 365
Glu Gln Tyr Asn Ser Thr Tyr Arg Val Val Ser Val Leu Thr Val Leu
    370                 375                 380
His Gln Asp Trp Leu Asn Gly Lys Glu Tyr Lys Cys Lys Val Ser Asn
385                 390                 395                 400
Lys Ala Leu Pro Arg Pro Ile Glu Lys Thr Ile Ser Lys Ala Lys Gly
                405                 410                 415
Gln Pro Arg Glu Pro Gln Val Tyr Thr Leu Pro Pro Ser Arg Asp Glu
            420                 425                 430
Leu Thr Lys Asn Gln Val Ser Leu Thr Cys Leu Val Lys Gly Phe Tyr
        435                 440                 445
Pro Ser Asp Ile Ala Val Glu Trp Glu Ser Asn Gly Gln Pro Glu Asn
    450                 455                 460
Asn Tyr Lys Thr Thr Pro Pro Val Leu Asp Ser Asp Gly Ser Phe Phe
465                 470                 475                 480
Leu Tyr Ser Lys Leu Thr Val Asp Lys Ser Arg Trp Gln Gln Gly Asn
                485                 490                 495
Val Phe Ser Cys Ser Val Met His Glu Ala Leu His Asn His Tyr Thr
            500                 505                 510
Gln Lys Ser Leu Ser Leu Ser Pro Gly Lys
```

<210> SEQ ID NO 30
<211> LENGTH: 511
<212> TYPE: PRT
<213> ORGANISM: Artificial sequence
<220> FEATURE:
<223> OTHER INFORMATION: amino acid sequence for the heavy chain of
      Human anti-murine CD40 antibody Anti-mCD40-hIgG2(H3)

<400> SEQUENCE: 30

Met Asp Ile Arg Leu Ser Leu Val Phe Leu Val Leu Phe Ile Lys Gly
1               5                   10                  15

Val Gln Cys Glu Val Gln Leu Val Glu Ser Asp Gly Gly Leu Val Gln
            20                  25                  30

Pro Gly Arg Ser Leu Lys Leu Pro Cys Ala Ala Ser Gly Phe Thr Phe
        35                  40                  45

Ser Asp Tyr Tyr Met Ala Trp Val Arg Gln Ala Pro Thr Lys Gly Leu
    50                  55                  60

Glu Trp Val Ala Ser Ile Ser Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Gly Arg His Ser Ser Tyr Phe Asp Tyr Trp Gly Gln Gly
        115                 120                 125

Val Met Val Thr Val Ser Ser Ala Ser Thr Lys Gly Pro Ser Val Phe
    130                 135                 140

Pro Leu Ala Pro Cys Ser Arg Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Thr Cys Asn Val Asn His Lys Pro
    210                 215                 220

Ser Asn Thr Lys Val Asp Lys Arg Val Glu Leu Lys Thr Pro Leu Gly
225                 230                 235                 240

Asp Thr Thr His Thr Cys Pro Arg Cys Pro Glu Pro Lys Ser Cys Asp
                245                 250                 255

Thr Pro Pro Pro Cys Pro Arg Cys Pro Glu Pro Lys Ser Cys Asp Thr
            260                 265                 270

Pro Pro Pro Cys Pro Arg Cys Pro Glu Pro Lys Ser Cys Asp Thr Pro
        275                 280                 285

Pro Pro Cys Pro Arg Cys Pro Ala Pro Val Ala Gly Pro Ser Val
    290                 295                 300

Phe Leu Phe Pro Pro Lys Pro Lys Asp Thr Leu Met Ile Ser Arg Thr
305                 310                 315                 320

Pro Glu Val Thr Cys Val Val Asp Val Ser His Glu Asp Pro Glu
                325                 330                 335

Val Gln Phe Asn Trp Tyr Val Asp Gly Val Glu Val His Asn Ala Lys
            340                 345                 350

```
Thr Lys Pro Arg Glu Glu Gln Phe Asn Ser Thr Phe Arg Val Val Ser
        355                 360                 365

Val Leu Thr Val Val His Gln Asp Trp Leu Asn Gly Lys Glu Tyr Lys
    370                 375                 380

Cys Lys Val Ser Asn Lys Gly Leu Pro Ala Pro Ile Glu Lys Thr Ile
385                 390                 395                 400

Ser Lys Thr Lys Gly Gln Pro Arg Glu Pro Gln Val Tyr Thr Leu Pro
                405                 410                 415

Pro Ser Arg Glu Glu Met Thr Lys Asn Gln Val Ser Leu Thr Cys Leu
            420                 425                 430

Val Lys Gly Phe Tyr Pro Ser Asp Ile Ala Val Glu Trp Glu Ser Asn
        435                 440                 445

Gly Gln Pro Glu Asn Asn Tyr Lys Thr Thr Pro Pro Met Leu Asp Ser
    450                 455                 460

Asp Gly Ser Phe Phe Leu Tyr Ser Lys Leu Thr Val Asp Lys Ser Arg
465                 470                 475                 480

Trp Gln Gln Gly Asn Val Phe Ser Cys Ser Val Met His Glu Ala Leu
                485                 490                 495

His Asn His Tyr Thr Gln Lys Ser Leu Ser Leu Ser Pro Gly Lys
            500                 505                 510

<210> SEQ ID NO 31
<211> LENGTH: 521
<212> TYPE: PRT
<213> ORGANISM: Artificial sequence
<220> FEATURE:
<223> OTHER INFORMATION: amino acid sequence for the heavy chain of
      Human anti-human CD40 antibody Anti-hCD40-hIgG2(H3)

<400> SEQUENCE: 31

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Asp Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
        115                 120                 125

Cys Ser Tyr Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Gly Gly Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205
```

Ser Leu Ser Ser Val Val Thr Val Pro Ser Ser Ser Leu Gly Thr Gln
        210                 215                 220

Thr Tyr Thr Cys Asn Val Asn His Lys Pro Ser Asn Thr Lys Val Asp
225                 230                 235                 240

Lys Arg Val Glu Leu Lys Thr Pro Leu Gly Asp Thr Thr His Thr Cys
                245                 250                 255

Pro Arg Cys Pro Glu Pro Lys Ser Cys Asp Thr Pro Pro Cys Pro
            260                 265                 270

Arg Cys Pro Glu Pro Lys Ser Cys Asp Thr Pro Pro Cys Pro Arg
        275                 280                 285

Cys Pro Glu Pro Lys Ser Cys Asp Thr Pro Pro Cys Pro Arg Cys
    290                 295                 300

Pro Ala Pro Pro Val Ala Gly Pro Ser Val Phe Leu Phe Pro Pro Lys
305                 310                 315                 320

Pro Lys Asp Thr Leu Met Ile Ser Arg Thr Pro Glu Val Thr Cys Val
                325                 330                 335

Val Val Asp Val Ser His Glu Asp Pro Glu Val Gln Phe Asn Trp Tyr
            340                 345                 350

Val Asp Gly Val Glu Val His Asn Ala Lys Thr Lys Pro Arg Glu Glu
        355                 360                 365

Gln Phe Asn Ser Thr Phe Arg Val Val Ser Val Leu Thr Val Val His
    370                 375                 380

Gln Asp Trp Leu Asn Gly Lys Glu Tyr Lys Cys Lys Val Ser Asn Lys
385                 390                 395                 400

Gly Leu Pro Ala Pro Ile Glu Lys Thr Ile Ser Lys Thr Lys Gly Gln
                405                 410                 415

Pro Arg Glu Pro Gln Val Tyr Thr Leu Pro Pro Ser Arg Glu Glu Met
            420                 425                 430

Thr Lys Asn Gln Val Ser Leu Thr Cys Leu Val Lys Gly Phe Tyr Pro
        435                 440                 445

Ser Asp Ile Ala Val Glu Trp Glu Ser Asn Gly Gln Pro Glu Asn Asn
    450                 455                 460

Tyr Lys Thr Thr Pro Pro Met Leu Asp Ser Asp Gly Ser Phe Phe Leu
465                 470                 475                 480

Tyr Ser Lys Leu Thr Val Asp Lys Ser Arg Trp Gln Gln Gly Asn Val
                485                 490                 495

Phe Ser Cys Ser Val Met His Glu Ala Leu His Asn His Tyr Thr Gln
            500                 505                 510

Lys Ser Leu Ser Leu Ser Pro Gly Lys
        515                 520

<210> SEQ ID NO 32
<211> LENGTH: 462
<212> TYPE: PRT
<213> ORGANISM: Artificial sequence
<220> FEATURE:
<223> OTHER INFORMATION: amino acid sequence for the heavy chain of
      Human anti-murine CD40 antibody Anti-mCD40-hIgG3(H2)

<400> SEQUENCE: 32

Met Asp Ile Arg Leu Ser Leu Val Phe Leu Val Leu Phe Ile Lys Gly
1               5                   10                  15

Val Gln Cys Glu Val Gln Leu Val Glu Ser Asp Gly Gly Leu Val Gln
            20                  25                  30

Pro Gly Arg Ser Leu Lys Leu Pro Cys Ala Ala Ser Gly Phe Thr Phe

```
            35                  40                  45
Ser Asp Tyr Tyr Met Ala Trp Val Arg Gln Ala Pro Thr Lys Gly Leu
 50                  55                  60
Glu Trp Val Ala Ser Ile Ser Tyr Asp Gly Ser Ser Thr Tyr Tyr Arg
 65                  70                  75                  80
Asp Ser Val Lys Gly Arg Phe Thr Ile Ser Arg Asp Asn Ala Lys Ser
                 85                  90                  95
Thr Leu Tyr Leu Gln Met Asp Ser Leu Arg Ser Glu Asp Thr Ala Thr
            100                 105                 110
Tyr Tyr Cys Gly Arg His Ser Ser Tyr Phe Asp Tyr Trp Gly Gln Gly
            115                 120                 125
Val Met Val Thr Val Ser Ser Ala Ser Thr Lys Gly Pro Ser Val Phe
130                 135                 140
Pro Leu Ala Pro Cys Ser Arg Ser Thr Ser Glu Ser Thr Ala Ala Leu
145                 150                 155                 160
Gly Cys Leu Val Lys Asp Tyr Phe Pro Glu Pro Val Thr Val Ser Trp
                165                 170                 175
Asn Ser Gly Ala Leu Thr Ser Gly Val His Thr Phe Pro Ala Val Leu
            180                 185                 190
Gln Ser Ser Gly Leu Tyr Ser Leu Ser Ser Val Val Thr Val Pro Ser
            195                 200                 205
Ser Asn Phe Gly Thr Gln Thr Tyr Thr Cys Asn Val Asp His Lys Pro
210                 215                 220
Ser Asn Thr Lys Val Asp Lys Thr Val Glu Arg Lys Cys Cys Val Glu
225                 230                 235                 240
Cys Pro Pro Cys Pro Ala Pro Glu Leu Leu Gly Gly Pro Ser Val Phe
                245                 250                 255
Leu Phe Pro Pro Lys Pro Lys Asp Thr Leu Met Ile Ser Arg Thr Pro
            260                 265                 270
Glu Val Thr Cys Val Val Val Asp Val Ser His Glu Asp Pro Glu Val
            275                 280                 285
Gln Phe Lys Trp Tyr Val Asp Gly Val Glu Val His Asn Ala Lys Thr
290                 295                 300
Lys Pro Arg Glu Glu Gln Tyr Asn Ser Thr Phe Arg Val Val Ser Val
305                 310                 315                 320
Leu Thr Val Leu His Gln Asp Trp Leu Asn Gly Lys Glu Tyr Lys Cys
                325                 330                 335
Lys Val Ser Asn Lys Ala Leu Pro Ala Pro Ile Glu Lys Thr Ile Ser
            340                 345                 350
Lys Thr Lys Gly Gln Pro Arg Glu Pro Gln Val Tyr Thr Leu Pro Pro
            355                 360                 365
Ser Arg Glu Glu Met Thr Lys Asn Gln Val Ser Leu Thr Cys Leu Val
            370                 375                 380
Lys Gly Phe Tyr Pro Ser Asp Ile Ala Val Glu Trp Glu Ser Ser Gly
385                 390                 395                 400
Gln Pro Glu Asn Asn Tyr Asn Thr Thr Pro Pro Met Leu Asp Ser Asp
                405                 410                 415
Gly Ser Phe Phe Leu Tyr Ser Lys Leu Thr Val Asp Lys Ser Arg Trp
            420                 425                 430
Gln Gln Gly Asn Ile Phe Ser Cys Ser Val Met His Glu Ala Leu His
            435                 440                 445
Asn Arg Phe Thr Gln Lys Ser Leu Ser Leu Ser Pro Gly Lys
450                 455                 460
```

-continued

<210> SEQ ID NO 33
<211> LENGTH: 472
<212> TYPE: PRT
<213> ORGANISM: Artificial sequence
<220> FEATURE:
<223> OTHER INFORMATION: amino acid sequence for the heavy chain of
      Human anti-human CD40 antibody Anti-hCD40-hIgG3(H2)

<400> SEQUENCE: 33

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Asp Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
        115                 120                 125

Cys Ser Tyr Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Gln Phe Lys Trp Tyr Val
    290                 295                 300

Asp Gly Val Glu Val His Asn Ala Lys Thr Lys Pro Arg Glu Glu Gln
305                 310                 315                 320

Tyr Asn Ser Thr Phe Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Thr Lys Gly Gln Pro

```
                    355                 360                 365
Arg Glu Pro Gln Val Tyr Thr Leu Pro Pro Ser Arg Glu Glu Met Thr
370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Ser Gly Gln Pro Glu Asn Asn Tyr
                405                 410                 415

Asn Thr Thr Pro Pro Met Leu Asp Ser Asp Gly Ser Phe Phe Leu Tyr
                420                 425                 430

Ser Lys Leu Thr Val Asp Lys Ser Arg Trp Gln Gln Gly Asn Ile Phe
                435                 440                 445

Ser Cys Ser Val Met His Glu Ala Leu His Asn Arg Phe Thr Gln Lys
                450                 455                 460

Ser Leu Ser Leu Ser Pro Gly Lys
465                 470

<210> SEQ ID NO 34
<211> LENGTH: 465
<212> TYPE: PRT
<213> ORGANISM: Artificial sequence
<220> FEATURE:
<223> OTHER INFORMATION: amino acid sequence for the heavy chain of
      Human anti-murine CD40 antibody Anti-mCD40-hIgG1-NA

<400> SEQUENCE: 34

Met Asp Ile Arg Leu Ser Leu Val Phe Leu Val Leu Phe Ile Lys Gly
1               5                   10                  15

Val Gln Cys Glu Val Gln Leu Val Glu Ser Asp Gly Gly Leu Val Gln
                20                  25                  30

Pro Gly Arg Ser Leu Lys Leu Pro Cys Ala Ala Ser Gly Phe Thr Phe
            35                  40                  45

Ser Asp Tyr Tyr Met Ala Trp Val Arg Gln Ala Pro Thr Lys Gly Leu
        50                  55                  60

Glu Trp Val Ala Ser Ile Ser Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Gly Arg His Ser Ser Tyr Phe Asp Tyr Trp Gly Gln Gly
        115                 120                 125

Val Met Val Thr Val Ser Ser Ala Thr Thr Lys Gly Pro Ser Val Phe
130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240
```

```
Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
        260                 265                 270

Arg Thr Pro Glu Val Thr Cys Val Val Val Asp Val Ser His Glu Asp
    275                 280                 285

Pro Glu Val Lys Phe Asn Trp Tyr Val Asp Gly Val Glu Val His Asn
290                 295                 300

Ala Lys Thr Lys Pro Arg Glu Glu Gln Tyr Ala Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 35
<211> LENGTH: 475
<212> TYPE: PRT
<213> ORGANISM: Artificial sequence
<220> FEATURE:
<223> OTHER INFORMATION: amino acid sequence for the heavy chain of
      Human anti-human CD40 antibody Anti-hCD40-hIgG1-NA

<400> SEQUENCE: 35

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Asp Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
        115                 120                 125
```

```
Cys Ser Tyr Phe Asp Tyr Trp Gly Gln Gly Thr Leu Val Thr Val Ser
    130                 135                 140

Ser Ala Thr Thr Lys Gly Pro Ser Val Phe Pro Leu Ala Pro Ser Ser
145                 150                 155                 160

Lys Ser Thr Ser Gly Gly Thr Ala Ala Leu Gly Cys Leu Val Lys Asp
            165                 170                 175

Tyr Phe Pro Glu Pro Val Thr Val Ser Trp Asn Ser Gly Ala Leu Thr
                180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Ser Leu Gly Thr Gln
    210                 215                 220

Thr Tyr Ile Cys Asn Val Asn His Lys Pro Ser Asn Thr Lys Val Asp
225                 230                 235                 240

Lys Arg Val Glu Pro Lys Ser Cys Asp Lys Thr His Thr Cys Pro Pro
                245                 250                 255

Cys Pro Ala Pro Glu Leu Leu Gly Gly Pro Ser Val Phe Leu Phe Pro
                260                 265                 270

Pro Lys Pro Lys Asp Thr Leu Met Ile Ser Arg Thr Pro Glu Val Thr
            275                 280                 285

Cys Val Val Val Asp Val Ser His Glu Asp Pro Glu Val Lys Phe Asn
    290                 295                 300

Trp Tyr Val Asp Gly Val Glu Val His Asn Ala Lys Thr Lys Pro Arg
305                 310                 315                 320

Glu Glu Gln Tyr Ala Ser Thr Tyr Arg Val Val Ser Val Leu Thr Val
                325                 330                 335

Leu His Gln Asp Trp Leu Asn Gly Lys Glu Tyr Lys Cys Lys Val Ser
            340                 345                 350

Asn Lys Ala Leu Pro Ala Pro Ile Glu Lys Thr Ile Ser Lys Ala Lys
            355                 360                 365

Gly Gln Pro Arg Glu Pro Gln Val Tyr Thr Leu Pro Pro Ser Arg Asp
370                 375                 380

Glu Leu Thr Lys Asn Gln Val Ser Leu Thr Cys Leu Val Lys Gly Phe
385                 390                 395                 400

Tyr Pro Ser Asp Ile Ala Val Glu Trp Glu Ser Asn Gly Gln Pro Glu
                405                 410                 415

Asn Asn Tyr Lys Thr Thr Pro Pro Val Leu Asp Ser Asp Gly Ser Phe
            420                 425                 430

Phe Leu Tyr Ser Lys Leu Thr Val Asp Lys Ser Arg Trp Gln Gln Gly
    435                 440                 445

Asn Val Phe Ser Cys Ser Val Met His Glu Ala Leu His Asn His Tyr
    450                 455                 460

Thr Gln Lys Ser Leu Ser Leu Ser Pro Gly Lys
465                 470                 475

<210> SEQ ID NO 36
<211> LENGTH: 461
<212> TYPE: PRT
<213> ORGANISM: Artificial sequence
<220> FEATURE:
<223> OTHER INFORMATION: amino acid sequence for the heavy chain of
      Human anti-murine CD40 antibody Anti-mCD40-hIgG2-NA

<400> SEQUENCE: 36

Met Asp Ile Arg Leu Ser Leu Val Phe Leu Val Leu Phe Ile Lys Gly
```

-continued

```
1               5                   10                  15
Val Gln Cys Glu Val Gln Leu Val Glu Ser Asp Gly Gly Leu Val Gln
                20                  25                  30
Pro Gly Arg Ser Leu Lys Leu Pro Cys Ala Ala Ser Gly Phe Thr Phe
            35                  40                  45
Ser Asp Tyr Tyr Met Ala Trp Val Arg Gln Ala Pro Thr Lys Gly Leu
    50                  55                  60
Glu Trp Val Ala Ser Ile Ser Tyr Asp Gly Ser Ser Thr Tyr Tyr Arg
65                  70                  75                  80
Asp Ser Val Lys Gly Arg Phe Thr Ile Ser Arg Asp Asn Ala Lys Ser
                85                  90                  95
Thr Leu Tyr Leu Gln Met Asp Ser Leu Arg Ser Glu Asp Thr Ala Thr
            100                 105                 110
Tyr Tyr Cys Gly Arg His Ser Ser Tyr Phe Asp Tyr Trp Gly Gln Gly
                115                 120                 125
Val Met Val Thr Val Ser Ser Ala Ser Thr Lys Gly Pro Ser Val Phe
        130                 135                 140
Pro Leu Ala Pro Cys Ser Arg Ser Thr Ser Glu Ser Thr Ala Ala Leu
145                 150                 155                 160
Gly Cys Leu Val Lys Asp Tyr Phe Pro Glu Pro Val Thr Val Ser Trp
                165                 170                 175
Asn Ser Gly Ala Leu Thr Ser Gly Val His Thr Phe Pro Ala Val Leu
            180                 185                 190
Gln Ser Ser Gly Leu Tyr Ser Leu Ser Ser Val Val Thr Val Pro Ser
        195                 200                 205
Ser Asn Phe Gly Thr Gln Thr Tyr Thr Cys Asn Val Asp His Lys Pro
    210                 215                 220
Ser Asn Thr Lys Val Asp Lys Thr Val Glu Arg Lys Cys Cys Val Glu
225                 230                 235                 240
Cys Pro Pro Cys Pro Ala Pro Pro Val Ala Gly Pro Ser Val Phe Leu
                245                 250                 255
Phe Pro Pro Lys Pro Lys Asp Thr Leu Met Ile Ser Arg Thr Pro Glu
            260                 265                 270
Val Thr Cys Val Val Asp Val Ser His Glu Asp Pro Glu Val Gln
        275                 280                 285
Phe Asn Trp Tyr Val Asp Gly Val Glu Val His Asn Ala Lys Thr Lys
    290                 295                 300
Pro Arg Glu Glu Gln Phe Ala Ser Thr Phe Arg Val Val Ser Val Leu
305                 310                 315                 320
Thr Val Val His Gln Asp Trp Leu Asn Gly Lys Glu Tyr Lys Cys Lys
                325                 330                 335
Val Ser Asn Lys Gly Leu Pro Ala Pro Ile Glu Lys Thr Ile Ser Lys
            340                 345                 350
Thr Lys Gly Gln Pro Arg Glu Pro Gln Val Tyr Thr Leu Pro Pro Ser
        355                 360                 365
Arg Glu Glu Met Thr Lys Asn Gln Val Ser Leu Thr Cys Leu Val Lys
    370                 375                 380
Gly Phe Tyr Pro Ser Asp Ile Ala Val Glu Trp Glu Ser Asn Gly Gln
385                 390                 395                 400
Pro Glu Asn Asn Tyr Lys Thr Thr Pro Pro Met Leu Asp Ser Asp Gly
            405                 410                 415
Ser Phe Phe Leu Tyr Ser Lys Leu Thr Val Asp Lys Ser Arg Trp Gln
        420                 425                 430
```

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460

<210> SEQ ID NO 37
<211> LENGTH: 471
<212> TYPE: PRT
<213> ORGANISM: Artificial sequence
<220> FEATURE:
<223> OTHER INFORMATION: amino acid sequence for the heavy chain of
      Human anti-human CD40 antibody Anti-hCD40-hIgG2-NA

<400> SEQUENCE: 37

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Asp Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
        115                 120                 125

Cys Ser Tyr Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Ala Ser Thr Phe Arg Val Val Ser Val Leu Thr Val Val His Gln Asp

-continued

```
                    325                 330                 335
Trp Leu Asn Gly Lys Glu Tyr Lys Cys Lys Val Ser Asn Lys Gly Leu
                340                 345                 350

Pro Ala Pro Ile Glu Lys Thr Ile Ser Lys Thr Lys Gly Gln Pro Arg
            355                 360                 365

Glu Pro Gln Val Tyr Thr Leu Pro Pro Ser Arg Glu Glu Met Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Met Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 38
<211> LENGTH: 471
<212> TYPE: PRT
<213> ORGANISM: Artificial sequence
<220> FEATURE:
<223> OTHER INFORMATION: amino acid sequence for the heavy chain of
      Human anti-human CD40 antibody Anti-hCD40-hIgG2-SE

<400> SEQUENCE: 38

Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
                20                  25                  30

Pro Gly Ala Ser Val Lys Val Ser Cys Lys Ala Ser Gly Tyr Thr Phe
            35                  40                  45

Thr Gly Tyr Tyr Met His Trp Val Arg Gln Ala Pro Gly Gln Gly Leu
        50                  55                  60

Glu Trp Met Gly Trp Ile Asn Pro Asp Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
        115                 120                 125

Cys Ser Tyr Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205
```

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Glu His Glu Asp Pro Glu Val Gln Phe Asn Trp Tyr Val Asp
290                 295                 300

Gly Val Glu Val His Asn Ala Lys Thr Lys Pro Arg Glu Glu Gln Phe
305                 310                 315                 320

Asn Ser Thr Phe Arg Val Val Ser Val Leu Thr Val Val His Gln Asp
                325                 330                 335

Trp Leu Asn Gly Lys Glu Tyr Lys Cys Lys Val Ser Asn Lys Gly Leu
            340                 345                 350

Pro Ala Pro Ile Glu Lys Thr Ile Ser Lys Thr Lys Gly Gln Pro Arg
        355                 360                 365

Glu Pro Gln Val Tyr Thr Leu Pro Pro Ser Arg Glu Glu Met Thr Lys
370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Met Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 39
<211> LENGTH: 471
<212> TYPE: PRT
<213> ORGANISM: Artificial sequence
<220> FEATURE:
<223> OTHER INFORMATION: amino acid sequence for the heavy chain of
      Human anti-human CD40 antibody Anti-hCD40-hIgG2-LF

<400> SEQUENCE: 39

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Asp Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
            115                 120                 125

Cys Ser Tyr Phe Asp Tyr Trp Gly Gln Gly Thr Leu Val Thr Val Ser
            130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
            165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Asn Phe Gly Thr Gln
            210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
            245                 250                 255

Pro Pro Val Ala Gly Pro Ser Val Phe Leu Phe Pro Pro Lys Pro Lys
            260                 265                 270

Asp Thr Leu Met Ile Ser Arg Thr Pro Glu Val Thr Cys Val Val Val
            275                 280                 285

Asp Val Ser His Glu Asp Pro Glu Val Gln Phe Asn Trp Tyr Val Asp
            290                 295                 300

Gly Val Glu Val His Asn Ala Lys Thr Lys Pro Arg Glu Glu Gln Phe
305                 310                 315                 320

Asn Ser Thr Phe Arg Val Val Ser Val Leu Thr Val Val His Gln Asp
            325                 330                 335

Trp Leu Asn Gly Lys Glu Tyr Lys Cys Lys Val Ser Asn Lys Gly Phe
            340                 345                 350

Pro Ala Pro Ile Glu Lys Thr Ile Ser Lys Thr Lys Gly Gln Pro Arg
            355                 360                 365

Glu Pro Gln Val Tyr Thr Leu Pro Pro Ser Arg Glu Glu Met Thr Lys
            370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
            405                 410                 415

Thr Thr Pro Pro Met Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465                 470

<210> SEQ ID NO 40
<211> LENGTH: 471
<212> TYPE: PRT
<213> ORGANISM: Artificial sequence
<220> FEATURE:

<223> OTHER INFORMATION: amino acid sequence for the heavy chain of
Human anti-human CD40 antibody Anti-hCD40-hIgG2-SELF

<400> SEQUENCE: 40

```
Met Asp Trp Thr Trp Arg Ile Leu Phe Leu Val Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Gly Tyr Tyr Met His Trp Val Arg Gln Ala Pro Gly Gln Gly Leu
    50                  55                  60

Glu Trp Met Gly Trp Ile Asn Pro Asp Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
        115                 120                 125

Cys Ser Tyr Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Lys Pro Lys
            260                 265                 270

Asp Thr Leu Met Ile Ser Arg Thr Pro Glu Val Thr Cys Val Val Val
        275                 280                 285

Asp Val Glu His Glu Asp Pro Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Asn Ser Thr Phe Arg Val Val Ser Val Leu Thr Val Val His Gln Asp
                325                 330                 335

Trp Leu Asn Gly Lys Glu Tyr Lys Cys Lys Val Ser Asn Lys Gly Phe
            340                 345                 350

Pro Ala Pro Ile Glu Lys Thr Ile Ser Lys Thr Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400
```

Ile Ala Val Glu Trp Glu Ser Asn Gly Gln Pro Glu Asn Asn Tyr Lys
            405                 410                 415

Thr Thr Pro Pro Met Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
            450                 455                 460

Leu Ser Leu Ser Pro Gly Lys
465             470

<210> SEQ ID NO 41
<211> LENGTH: 471
<212> TYPE: PRT
<213> ORGANISM: Artificial sequence
<220> FEATURE:
<223> OTHER INFORMATION: amino acid sequence for the heavy chain of
      Human anti-human CD40 antibody Anti-hCD40-hIgG2-HD

<400> SEQUENCE: 41

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
            35                  40                  45

Thr Gly Tyr Tyr Met His Trp Val Arg Gln Ala Pro Gly Gln Gly Leu
    50                  55                  60

Glu Trp Met Gly Trp Ile Asn Pro Asp Ser Gly Gly Thr Asn Tyr Ala
65                  70                  75                  80

Gln Lys Phe Gln Gly Arg Val Thr Met Thr Arg Asp Thr Ser Ile Ser
                85                  90                  95

Thr Ala Tyr Met Glu Leu Asn Arg Leu Arg Ser Asp Asp Thr Ala Val
            100                 105                 110

Tyr Tyr Cys Ala Arg Asp Gln Pro Leu Gly Tyr Cys Thr Asn Gly Val
            115                 120                 125

Cys Ser Tyr Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
            195                 200                 205

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ser Arg Thr Pro Glu Val Thr Cys Val Val Val

```
            275                 280                 285
Asp Val Ser Asp Glu Asp Pro Glu Val Gln Phe Asn Trp Tyr Val Asp
        290                 295                 300
Gly Val Glu Val His Asn Ala Lys Thr Lys Pro Arg Glu Glu Gln Phe
305                 310                 315                 320
Asn Ser Thr Phe Arg Val Val Ser Val Leu Thr Val Val His Gln Asp
                325                 330                 335
Trp Leu Asn Gly Lys Glu Tyr Lys Cys Lys Val Ser Asn Lys Gly Leu
            340                 345                 350
Pro Ala Pro Ile Glu Lys Thr Ile Ser Lys Thr Lys Gly Gln Pro Arg
        355                 360                 365
Glu Pro Gln Val Tyr Thr Leu Pro Pro Ser Arg Glu Glu Met Thr Lys
    370                 375                 380
Asn Gln Val Ser Leu Thr Cys Leu Val Lys Gly Phe Tyr Pro Ser Asp
385                 390                 395                 400
Ile Ala Val Glu Trp Glu Ser Asn Gly Gln Pro Glu Asn Asn Tyr Lys
                405                 410                 415
Thr Thr Pro Pro Met Leu Asp Ser Asp Gly Ser Phe Phe Leu Tyr Ser
            420                 425                 430
Lys Leu Thr Val Asp Lys Ser Arg Trp Gln Gln Gly Asn Val Phe Ser
        435                 440                 445
Cys Ser Val Met His Glu Ala Leu His Asn His Tyr Thr Gln Lys Ser
    450                 455                 460
Leu Ser Leu Ser Pro Gly Lys
465                 470

<210> SEQ ID NO 42
<211> LENGTH: 471
<212> TYPE: PRT
<213> ORGANISM: Artificial sequence
<220> FEATURE:
<223> OTHER INFORMATION: amino acid sequence for the heavy chain of
      Human anti-human CD40 antibody Anti-hCD40-hIgG2-PG

<400> SEQUENCE: 42

Met Asp Trp Thr Trp Arg Ile Leu Phe Leu Val Ala Ala Ala Thr Gly
1               5                   10                  15
Ala His Ser Gln Val Gln Leu Val Gln Ser Gly Ala Glu Val Lys Lys
                20                  25                  30
Pro Gly Ala Ser Val Lys Val Ser Cys Lys Ala Ser Gly Tyr Thr Phe
            35                  40                  45
Thr Gly Tyr Tyr Met His Trp Val Arg Gln Ala Pro Gly Gln Gly Leu
        50                  55                  60
Glu Trp Met Gly Trp Ile Asn Pro Asp Ser Gly Gly Thr Asn Tyr Ala
65                  70                  75                  80
Gln Lys Phe Gln Gly Arg Val Thr Met Thr Arg Asp Thr Ser Ile Ser
                85                  90                  95
Thr Ala Tyr Met Glu Leu Asn Arg Leu Arg Ser Asp Asp Thr Ala Val
            100                 105                 110
Tyr Tyr Cys Ala Arg Asp Gln Pro Leu Gly Tyr Cys Thr Asn Gly Val
        115                 120                 125
Cys Ser Tyr Phe Asp Tyr Trp Gly Gln Gly Thr Leu Val Thr Val Ser
    130                 135                 140
Ser Ala Ser Thr Lys Gly Pro Ser Val Phe Pro Leu Ala Pro Cys Ser
145                 150                 155                 160
```

-continued

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
            180                 185                 190

Ser Gly Val His Thr Phe Pro Ala Val Leu Gln Ser Ser Gly Leu Tyr
        195                 200                 205

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Gly Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Asn Ser Thr Phe Arg Val Val Ser Val Leu Thr Val Val His Gln Asp
                325                 330                 335

Trp Leu Asn Gly Lys Glu Tyr Lys Cys Lys Val Ser Asn Lys Gly Leu
            340                 345                 350

Pro Ala Pro Ile Glu Lys Thr Ile Ser Lys Thr Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Met Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 43
<211> LENGTH: 471
<212> TYPE: PRT
<213> ORGANISM: Artificial sequence
<220> FEATURE:
<223> OTHER INFORMATION: amino acid sequence for the heavy chain of
      Human anti-human CD40 antibody Anti-hCD40-hIgG2-HDPG

<400> SEQUENCE: 43

Met Asp Trp Thr Trp Arg Ile Leu Phe Leu Val Ala Ala Ala Thr Gly
1               5                   10                  15

Ala His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

```
Thr Gly Tyr Tyr Met His Trp Val Arg Gln Ala Pro Gly Gln Gly Leu
    50                  55                  60

Glu Trp Met Gly Trp Ile Asn Pro Asp Ser Gly Thr Asn Tyr Ala
65                  70                  75                  80

Gln Lys Phe Gln Gly Arg Val Thr Met Thr Arg Asp Thr Ser Ile Ser
                    85                  90                  95

Thr Ala Tyr Met Glu Leu Asn Arg Leu Arg Ser Asp Asp Thr Ala Val
                100                 105                 110

Tyr Tyr Cys Ala Arg Asp Gln Pro Leu Gly Tyr Cys Thr Asn Gly Val
        115                 120                 125

Cys Ser Tyr Phe Asp Tyr Trp Gly Gln Gly Thr Leu Val Thr Val Ser
    130                 135                 140

Ser Ala Ser Thr Lys Gly Pro Ser Val Phe Pro Leu Ala Pro Cys Ser
145                 150                 155                 160

Arg Ser Thr Ser Glu Ser Thr Ala Ala Leu Gly Cys Leu Val Lys Asp
                165                 170                 175

Tyr Phe Pro Glu Pro Val Thr Val Ser Trp Asn Ser Gly Ala Leu Thr
                180                 185                 190

Ser Gly Val His Thr Phe Pro Ala Val Leu Gln Ser Ser Gly Leu Tyr
    195                 200                 205

Ser Leu Ser Ser Val Val Thr Val Pro Ser Ser Asn Phe Gly Thr Gln
    210                 215                 220

Thr Tyr Thr Cys Asn Val Asp His Lys Pro Ser Asn Thr Lys Val Asp
225                 230                 235                 240

Lys Thr Val Glu Arg Lys Cys Cys Val Glu Cys Pro Pro Cys Pro Ala
                245                 250                 255

Pro Pro Val Ala Gly Pro Ser Val Phe Leu Phe Pro Pro Lys Pro Lys
                260                 265                 270

Asp Thr Leu Met Ile Ser Arg Thr Pro Glu Val Thr Cys Val Val Val
    275                 280                 285

Asp Val Ser Asp Glu Asp Gly Glu Val Gln Phe Asn Trp Tyr Val Asp
    290                 295                 300

Gly Val Glu Val His Asn Ala Lys Thr Lys Pro Arg Glu Glu Gln Phe
305                 310                 315                 320

Asn Ser Thr Phe Arg Val Val Ser Val Leu Thr Val Val His Gln Asp
                325                 330                 335

Trp Leu Asn Gly Lys Glu Tyr Lys Cys Lys Val Ser Asn Lys Gly Leu
                340                 345                 350

Pro Ala Pro Ile Glu Lys Thr Ile Ser Lys Thr Lys Gly Gln Pro Arg
    355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Met Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
450                 455                 460
```

Leu Ser Leu Ser Pro Gly Lys
465                 470

<210> SEQ ID NO 44
<211> LENGTH: 466
<212> TYPE: PRT
<213> ORGANISM: Artificial sequence
<220> FEATURE:
<223> OTHER INFORMATION: amino acid sequence for the heavy chain of
      Human anti-murine DR5 antibody Anti-mDR5-hIgG2

<400> SEQUENCE: 44

Met Arg Leu Leu Gly Leu Leu Tyr Leu Val Thr Thr Leu Pro Gly Val
1               5                   10                  15

Leu Ser Gln Ile Gln Leu Gln Glu Ser Gly Pro Gly Leu Val Lys Pro
            20                  25                  30

Ala Gln Ser Leu Ser Leu Thr Cys Ser Ile Thr Gly Phe Pro Ile Thr
        35                  40                  45

Ala Gly Gly Tyr Trp Trp Thr Trp Ile Arg Gln Phe Pro Gly Gln Lys
    50                  55                  60

Leu Glu Trp Met Gly Tyr Ile Tyr Ser Gly Ser Thr Asn Tyr Asn
65                  70                  75                  80

Pro Ser Ile Lys Ser Arg Ile Ser Ile Thr Arg Asp Thr Ala Lys Asn
                85                  90                  95

Gln Phe Phe Leu Gln Leu Asn Ser Val Thr Thr Glu Glu Asp Thr Ala
            100                 105                 110

Ile Tyr Tyr Cys Ala Arg Ala Gly Thr Ser Tyr Ser Gly Phe Phe Asp
        115                 120                 125

Ser Trp Gly Gln Gly Thr Leu Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
    210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

```
Lys Thr Ile Ser Lys Thr Lys Gly Gln Pro Arg Glu Pro Gln Val Tyr
            355                 360                 365

Thr Leu Pro Pro Ser Arg Glu Glu Met Thr Lys Asn Gln Val Ser Leu
        370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
            435                 440                 445

Glu Ala Leu His Asn His Tyr Thr Gln Lys Ser Leu Ser Leu Ser Pro
450                 455                 460

Gly Lys
465

<210> SEQ ID NO 45
<211> LENGTH: 470
<212> TYPE: PRT
<213> ORGANISM: Artificial sequence
<220> FEATURE:
<223> OTHER INFORMATION: amino acid sequence for the heavy chain of
      Human anti-murine DR5 antibody Anti-mDR5-hIgG1(V11)

<400> SEQUENCE: 45

Met Arg Leu Leu Gly Leu Leu Tyr Leu Val Thr Thr Leu Pro Gly Val
1               5                   10                  15

Leu Ser Gln Ile Gln Leu Gln Glu Ser Gly Pro Gly Leu Val Lys Pro
            20                  25                  30

Ala Gln Ser Leu Ser Leu Thr Cys Ser Ile Thr Gly Phe Pro Ile Thr
        35                  40                  45

Ala Gly Gly Tyr Trp Trp Thr Trp Ile Arg Gln Phe Pro Gly Gln Lys
    50                  55                  60

Leu Glu Trp Met Gly Tyr Ile Tyr Ser Ser Gly Ser Thr Asn Tyr Asn
65                  70                  75                  80

Pro Ser Ile Lys Ser Arg Ile Ser Ile Thr Arg Asp Thr Ala Lys Asn
                85                  90                  95

Gln Phe Phe Leu Gln Leu Asn Ser Val Thr Thr Glu Glu Asp Thr Ala
            100                 105                 110

Ile Tyr Tyr Cys Ala Arg Ala Gly Thr Ser Tyr Ser Gly Phe Phe Asp
        115                 120                 125

Ser Trp Gly Gln Gly Thr Leu Val Thr Val Ser Ser Ala Thr Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
```

```
                  225                 230                 235                 240

Lys Ser Cys Asp Lys Thr His Thr Cys Pro Pro Cys Pro Ala Pro Glu
                245                 250                 255

Leu Leu Gly Asp Asp Ser Val Phe Leu Phe Pro Pro Lys Pro Lys Asp
                260                 265                 270

Thr Leu Met Ile Ser Arg Thr Pro Glu Val Thr Cys Val Val Val Asp
                275                 280                 285

Val Ser Asp Glu Asp Gly Glu Val Lys Phe Asn Trp Tyr Val Asp Gly
                290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Arg Pro Ile Glu Lys Thr Ile Ser Lys Ala Lys Gly Gln Pro Arg Glu
                355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
                450                 455                 460

Ser Leu Ser Pro Gly Lys
465                 470

<210> SEQ ID NO 46
<211> LENGTH: 467
<212> TYPE: PRT
<213> ORGANISM: Artificial sequence
<220> FEATURE:
<223> OTHER INFORMATION: amino acid sequence for the heavy chain of
      Human anti-murine DR5 antibody Anti-mDR5-IgG2(V11)

<400> SEQUENCE: 46

Met Arg Leu Leu Gly Leu Leu Tyr Leu Val Thr Thr Leu Pro Gly Val
1               5                   10                  15

Leu Ser Gln Ile Gln Leu Gln Glu Ser Gly Pro Gly Leu Val Lys Pro
                20                  25                  30

Ala Gln Ser Leu Ser Leu Thr Cys Ser Ile Thr Gly Phe Pro Ile Thr
            35                  40                  45

Ala Gly Gly Tyr Trp Trp Thr Trp Ile Arg Gln Phe Pro Gly Gln Lys
        50                  55                  60

Leu Glu Trp Met Gly Tyr Ile Tyr Ser Ser Gly Ser Thr Asn Tyr Asn
65                  70                  75                  80

Pro Ser Ile Lys Ser Arg Ile Ser Ile Thr Arg Asp Thr Ala Lys Asn
                85                  90                  95

Gln Phe Phe Leu Gln Leu Asn Ser Val Thr Thr Glu Glu Asp Thr Ala
                100                 105                 110
```

```
Ile Tyr Tyr Cys Ala Arg Ala Gly Thr Ser Tyr Ser Gly Phe Phe Asp
            115                 120                 125

Ser Trp Gly Gln Gly Thr Leu Val Thr Val Ser Ser Ala Ser Thr Lys
130                 135                 140

Gly Pro Ser Val Phe Pro Leu Ala Pro Cys Ser Arg Ser Thr Ser Glu
145                 150                 155                 160

Ser Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Asn Phe Gly Thr Gln Thr Tyr Thr Cys Asn
210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Glu Leu Leu Gly
                245                 250                 255

Asp Asp Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser Asp
        275                 280                 285

Glu Asp Gly Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Arg Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly Lys
465

<210> SEQ ID NO 47
<211> LENGTH: 234
<212> TYPE: PRT
<213> ORGANISM: Artificial sequence
<220> FEATURE:
<223> OTHER INFORMATION: amino acid sequence for the light chain of
      Human anti-human CD40 antibody

<400> SEQUENCE: 47
```

Met Arg Leu Pro Ala Gln Leu Gly Leu Leu Leu Trp Phe Pro
1               5                   10                  15

Gly Ser Arg Cys Asp Ile Gln Met Thr Gln Ser Pro Ser Ser Val Ser
                20                  25                  30

Ala Ser Val Gly Asp Arg Val Thr Ile Thr Cys Arg Ala Ser Gln Gly
            35                  40                  45

Ile Tyr Ser Trp Leu Ala Trp Tyr Gln Gln Lys Pro Gly Lys Ala Pro
        50                  55                  60

Asn Leu Leu Ile Tyr Thr Ala Ser Thr Leu Gln Ser Gly Val Pro Ser
65              70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Ala Asn
            100                 105                 110

Ile Phe Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145             150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
210             215                 220

Val Thr Lys Ser Phe Asn Arg Gly Glu Cys
225                 230

<210> SEQ ID NO 48
<211> LENGTH: 233
<212> TYPE: PRT
<213> ORGANISM: Artificial sequence
<220> FEATURE:
<223> OTHER INFORMATION: amino acid sequence for the light chain of
      Human anti-murine CD40 antibody

<400> SEQUENCE: 48

Met Glu Thr Asp Arg Leu Leu Leu Trp Val Leu Leu Leu Trp Val Pro
1               5                   10                  15

Gly Ser Thr Gly Asp Thr Val Leu Thr Gln Ser Pro Ala Leu Ala Val
                20                  25                  30

Ser Pro Gly Glu Arg Val Thr Ile Ser Cys Arg Ala Ser Asp Ser Val
            35                  40                  45

Ser Thr Leu Met His Trp Tyr Gln Gln Lys Pro Gly Gln Gln Pro Lys
        50                  55                  60

Leu Leu Ile Tyr Leu Ala Ser His Leu Glu Ser Gly Val Pro Ala Arg
65              70                  75                  80

Phe Ser Gly Ser Gly Ser Gly Thr Asp Phe Thr Leu Thr Ile Asp Pro
                85                  90                  95

Val Glu Ala Asp Asp Thr Ala Thr Tyr Tyr Cys Gln Gln Ser Trp Asn
            100                 105                 110

Asp Pro Trp Thr Phe Gly Gly Gly Thr Lys Leu Glu Leu Lys Arg Thr

```
            115                 120                 125
Val Ala Ala Pro Ser Val Phe Ile Phe Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
                180                 185                 190

Ser Leu Ser Ser Thr Leu Thr Leu Ser Lys Ala Asp Tyr Glu Lys His
                195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 49
<211> LENGTH: 236
<212> TYPE: PRT
<213> ORGANISM: Artificial sequence
<220> FEATURE:
<223> OTHER INFORMATION: amino acid sequence for the light chain of Human anti-murine DR5

<400> SEQUENCE: 49

```
Met Ala Met Lys Val Pro Ala Gln Ala Leu Val Ile Leu Leu Leu Trp
1               5                   10                  15

Val Ser Gly Ala Thr Cys Asp Ile Gln Val Thr Gln Ser Pro Ser Leu
                20                  25                  30

Leu Ser Ala Ser Phe Gly Asp Lys Val Thr Ile Asn Cys Leu Val Thr
            35                  40                  45

Gln Asp Ile Thr Tyr Tyr Leu Ser Trp Tyr Gln Gln Lys Ser Gly Gln
    50                  55                  60

Pro Pro Thr Leu Leu Ile Tyr Asn Gly Asn Ser Leu Gln Ser Gly Val
65                  70                  75                  80

Pro Ser Arg Phe Ser Gly Gln Tyr Ser Gly Arg Thr Phe Thr Leu Ser
                85                  90                  95

Leu Ser Ser Leu Glu Pro Glu Asp Ala Gly Thr Tyr Tyr Cys Leu Gln
            100                 105                 110

His Tyr Ser Val Pro Phe Thr Phe Gly Gly Gly Thr Arg Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235
```

<210> SEQ ID NO 50
<211> LENGTH: 464
<212> TYPE: PRT
<213> ORGANISM: Artificial sequence
<220> FEATURE:
<223> OTHER INFORMATION: amino acid sequence for the heavy chain of
      Human anti-murine CD40 antibody Anti-mCD40-hIgG1-SDIE

<400> SEQUENCE: 50

```
Met Asp Ile Arg Leu Ser Leu Val Phe Leu Val Leu Phe Ile Lys Gly
1               5                   10                  15

Val Gln Cys Glu Val Gln Leu Val Glu Ser Asp Gly Gly Leu Val Gln
            20                  25                  30

Pro Gly Arg Ser Leu Lys Leu Pro Cys Ala Ala Ser Gly Phe Thr Phe
        35                  40                  45

Ser Asp Tyr Tyr Met Ala Trp Val Arg Gln Ala Pro Thr Lys Gly Leu
    50                  55                  60

Glu Trp Val Ala Ser Ile Ser Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Gly Arg His Ser Ser Tyr Phe Asp Tyr Trp Gly Gln Gly
        115                 120                 125

Val Met Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Asp Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Glu Glu Lys
            340                 345                 350

Thr Ile Ser Lys Ala Lys Gly Gln Pro Arg Glu Pro Gln Val Tyr Thr
        355                 360                 365
```

-continued

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Leu Pro Val Ser Gly
    450                 455                 460

<210> SEQ ID NO 51
<211> LENGTH: 461
<212> TYPE: PRT
<213> ORGANISM: Artificial sequence
<220> FEATURE:
<223> OTHER INFORMATION: amino acid sequence for the heavy chain of
      Human anti-murine CD40 antibody Anti-mCD40-hIgG2-SDIE

<400> SEQUENCE: 51

Met Asp Ile Arg Leu Ser Leu Val Phe Leu Val Leu Phe Ile Lys Gly
1               5                   10                  15

Val Gln Cys Glu Val Gln Leu Val Glu Ser Asp Gly Gly Leu Val Gln
            20                  25                  30

Pro Gly Arg Ser Leu Lys Leu Pro Cys Ala Ala Ser Gly Phe Thr Phe
        35                  40                  45

Ser Asp Tyr Tyr Met Ala Trp Val Arg Gln Ala Pro Thr Lys Gly Leu
    50                  55                  60

Glu Trp Val Ala Ser Ile Ser Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Gly Arg His Ser Ser Tyr Phe Asp Tyr Trp Gly Gln Gly
        115                 120                 125

Val Met Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Glu Leu Leu Gly Gly Pro Asp Val Phe
                245                 250                 255

Leu Phe Pro Pro Lys Pro Lys Asp Thr Leu Met Ile Ser Arg Thr Pro

```
                260                 265                 270
Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
        290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Ala Pro Glu Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Leu Pro Val Ser Gly
    450                 455                 460

<210> SEQ ID NO 52
<211> LENGTH: 462
<212> TYPE: PRT
<213> ORGANISM: Artificial sequence
<220> FEATURE:
<223> OTHER INFORMATION: amino acid sequence for the heavy chain of
      Human anti-murine CD40 antibody Anti-mCD40-hIgG2-GASDALIE

<400> SEQUENCE: 52

Met Asp Ile Arg Leu Ser Leu Val Phe Leu Val Leu Phe Ile Lys Gly
1               5                   10                  15

Val Gln Cys Glu Val Gln Leu Val Glu Ser Asp Gly Gly Leu Val Gln
            20                  25                  30

Pro Gly Arg Ser Leu Lys Leu Pro Cys Ala Ala Ser Gly Phe Thr Phe
        35                  40                  45

Ser Asp Tyr Tyr Met Ala Trp Val Arg Gln Ala Pro Thr Lys Gly Leu
    50                  55                  60

Glu Trp Val Ala Ser Ile Ser Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
                85                  90                  95

Thr Leu Tyr Leu Gln Met Asp Ser Leu Arg Ser Glu Asp Thr Ala Thr
            100                 105                 110

Tyr Tyr Cys Gly Arg His Ser Ser Tyr Phe Asp Tyr Trp Gly Gln Gly
        115                 120                 125

Val Met Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160
```

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Asn Phe Gly Thr Gln Thr Tyr Thr Cys Asn Val Asp His Lys Pro
    210                 215                 220

Ser Asn Thr Lys Val Asp Lys Thr Val Glu Arg Lys Cys Cys Val Glu
225                 230                 235                 240

Cys Pro Pro Cys Pro Ala Pro Glu Leu Leu Ala Gly Pro Asp Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
        275                 280                 285

Lys Phe Asn Trp Tyr Val Asp Gly Val Glu Val His Asn Ala Lys Thr
    290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Ala Leu Pro Leu Pro Glu Glu Lys Thr Ile Ser
            340                 345                 350

Lys Ala Lys Gly Gln Pro Arg Glu Pro Gln Val Tyr Thr Leu Pro Pro
        355                 360                 365

Ser Arg Asp Glu Leu Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
        435                 440                 445

Asn His Tyr Thr Gln Lys Ser Leu Ser Leu Ser Pro Gly Lys
    450                 455                 460

<210> SEQ ID NO 53
<211> LENGTH: 462
<212> TYPE: PRT
<213> ORGANISM: Artificial sequence
<220> FEATURE:
<223> OTHER INFORMATION: amino acid sequence for the heavy chain of
      Human anti-murine CD40 antibody Anti-mCD40-hIgG1-H1

<400> SEQUENCE: 53

Met Asp Ile Arg Leu Ser Leu Val Phe Leu Val Leu Phe Ile Lys Gly
1               5                   10                  15

Val Gln Cys Glu Val Gln Leu Val Glu Ser Asp Gly Gly Leu Val Gln
            20                  25                  30

Pro Gly Arg Ser Leu Lys Leu Pro Cys Ala Ala Ser Gly Phe Thr Phe
        35                  40                  45

Ser Asp Tyr Tyr Met Ala Trp Val Arg Gln Ala Pro Thr Lys Gly Leu
    50                  55                  60

Glu Trp Val Ala Ser Ile Ser Tyr Asp Gly Ser Ser Thr Tyr Tyr Arg
65                  70                  75                  80

Asp Ser Val Lys Gly Arg Phe Thr Ile Ser Arg Asp Asn Ala Lys Ser
            85                  90                  95

Thr Leu Tyr Leu Gln Met Asp Ser Leu Arg Ser Glu Asp Thr Ala Thr
            100                 105                 110

Tyr Tyr Cys Gly Arg His Ser Ser Tyr Phe Asp Tyr Trp Gly Gln Gly
            115                 120                 125

Val Met Val Thr Val Ser Ser Ala Ser Thr Lys Gly Pro Ser Val Phe
            130                 135                 140

Pro Leu Ala Pro Cys Ser Arg Ser Thr Ser Glu Ser Thr Ala Ala Leu
145                 150                 155                 160

Gly Cys Leu Val Lys Asp Tyr Phe Pro Glu Pro Val Thr Val Ser Trp
            165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
            195                 200                 205

Ser Asn Phe Gly Thr Gln Thr Tyr Thr Cys Asn Val Asp His Lys Pro
210                 215                 220

Ser Asn Thr Lys Val Asp Lys Thr Val Glu Arg Lys Cys Cys Val Glu
225                 230                 235                 240

Cys Pro Pro Cys Pro Ala Pro Glu Leu Leu Gly Gly Pro Ser Val Phe
            245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser His Glu Asp Pro Glu Val
            275                 280                 285

Lys Phe Asn Trp Tyr Val Asp Gly Val Glu Val His Asn Ala Lys Thr
            290                 295                 300

Lys Pro Arg Glu Glu Gln Tyr Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Ala Leu Pro Ala Pro Ile Glu Lys Thr Ile Ser
            340                 345                 350

Lys Ala Lys Gly Gln Pro Arg Glu Pro Gln Val Tyr Thr Leu Pro Pro
            355                 360                 365

Ser Arg Asp Glu Leu Thr Lys Asn Gln Val Ser Leu Thr Cys Leu Val
            370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
            405                 410                 415

Gly Ser Phe Phe Leu Tyr Ser Lys Leu Thr Val Asp Lys Ser Arg Trp
            420                 425                 430

Gln Gln Gly Asn Val Phe Ser Cys Ser Val Met His Glu Ala Leu His
            435                 440                 445

Asn His Tyr Thr Gln Lys Ser Leu Ser Leu Ser Pro Gly Lys
            450                 455                 460

<210> SEQ ID NO 54
<211> LENGTH: 470

<212> TYPE: PRT
<213> ORGANISM: Artificial sequence
<220> FEATURE:
<223> OTHER INFORMATION: amino acid sequence for the heavy chain of
    Human anti-murine DR5 antibody Anti-mDR5-hIgG1-GASDALIE

<400> SEQUENCE: 54

```
Met Arg Leu Leu Gly Leu Leu Tyr Leu Val Thr Thr Leu Pro Gly Val
1               5                   10                  15

Leu Ser Gln Ile Gln Leu Gln Glu Ser Gly Pro Gly Leu Val Lys Pro
            20                  25                  30

Ala Gln Ser Leu Ser Leu Thr Cys Ser Ile Thr Gly Phe Pro Ile Thr
        35                  40                  45

Ala Gly Gly Tyr Trp Trp Thr Trp Ile Arg Gln Phe Pro Gly Gln Lys
    50                  55                  60

Leu Glu Trp Met Gly Tyr Ile Tyr Ser Ser Gly Ser Thr Asn Tyr Asn
65                  70                  75                  80

Pro Ser Ile Lys Ser Arg Ile Ser Ile Thr Arg Asp Thr Ala Lys Asn
                85                  90                  95

Gln Phe Phe Leu Gln Leu Asn Ser Val Thr Thr Glu Glu Asp Thr Ala
            100                 105                 110

Ile Tyr Tyr Cys Ala Arg Ala Gly Thr Ser Tyr Ser Gly Phe Phe Asp
        115                 120                 125

Ser Trp Gly Gln Gly Thr Leu Val Thr Val Ser Ser Ala Thr Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Ala Gly Pro Asp Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Leu Pro Glu Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380
```

-continued

```
Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
        450                 455                 460

Ser Leu Ser Pro Gly Lys
465                 470
```